United States Patent
Kadereit et al.

(10) Patent No.: US 8,748,436 B2
(45) Date of Patent: Jun. 10, 2014

(54) CARBOXYLIC ACID DERIVATIVES HAVING A 2,5,7-SUBSTITUTED OXAZOLOPYRIMIDINE RING

(75) Inventors: Dieter Kadereit, Frankfurt am Main (DE); Matthias Schaefer, Frankfurt am Main (DE); Stephanie Hachtel, Frankfurt am Main (DE); Axel Dietrich, Frankfurt am Main (DE); Thomas Huebschle, Frankfurt am Main (DE); Andreas Gille, Frankfurt am Main (DE); Katrin Hiss, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/521,827

(22) PCT Filed: Jan. 12, 2011

(86) PCT No.: PCT/EP2011/050298
§ 371 (c)(1),
(2), (4) Date: Dec. 12, 2012

(87) PCT Pub. No.: WO2011/086077
PCT Pub. Date: Jul. 21, 2011

(65) Prior Publication Data
US 2013/0079357 A1    Mar. 28, 2013

(30) Foreign Application Priority Data
Jan. 13, 2010 (EP) .................................. 10305036

(51) Int. Cl.
*A61K 31/519* (2006.01)
(52) U.S. Cl.
USPC ..................................................... 514/260.1
(58) Field of Classification Search
None
See application file for complete search history.

(56) References Cited

U.S. PATENT DOCUMENTS

| | | | |
|---|---|---|---|
| 2013/0072501 A1 | 3/2013 | Kadereit et al. | |
| 2013/0072502 A1 | 3/2013 | Kadereit et al. | |
| 2013/0079358 A1 | 3/2013 | Kadereit et al. | |

FOREIGN PATENT DOCUMENTS

| WO | WO 2004/096813 | 11/2004 |
|---|---|---|
| WO | WO 2005/000833 | 1/2005 |
| WO | WO 2007/061458 | 5/2007 |
| WO | WO 2007/109334 | 9/2007 |
| WO | WO 2009/154775 | 12/2009 |
| WO | WO 2010/006704 | 1/2010 |

OTHER PUBLICATIONS

Anderson (Chem and Biol 10:787-797, 2003).*
Thiel (Nature Biotechnol 2:513-519, 2004).*
U.S. Appl. No. 13/521,823, filed Dec. 10, 2012, Kadereit, et al.
U.S. Appl. No. 13/521,829, filed Dec. 7, 2012, Kadereit, et al.
Mitsunobu, The Use of Diethyl Azodicarboxylate and Triphenylphosphine in Synthesis and Transformation of Natural Products, Synthesis, (1981), pp. 1-28.
Holschbach, et al., Synthesis and Evaluation of 7-Amino-2-(2(3)-Furyl)-5-Phenylethylamino-Oxazolo[5,4-d] Pyrimidines as Potential A2A Adenosine Receptor Antagonists for Positron Emission Tomogrphy (PET), European Journal of Medicinal Chemistry, vol. 41, (2006), pp. 7-15.
Johnson, et al., Researches on Pyrimidines. LXXXVII. Alkylation of 5-Amino-Uracil, J. Am. Chem. Soc., vol. 41, (1919), pp. 782-789.
Whittaker, A New Synthesis and the Chemical Properties of 5-Aminopyrimidine, J. Chem. Soc., (1951), pp. 1565-1570.
International Search Report for WO2011/086077 dated Jul. 21, 2011.
Johnson, et al., 5-Ethylsulfanyl-2-Phenyl-Oxazolo[5,4-a]Pyrimidine and its Hydrochloride Salt, American Chemical Journal, vol. 34, p. 202, (1905), Database Beilstein, Beilstein Instituted for Organic Chemistry, Database Accession No. BRN37636139 and BRN213378, (abstract).
Boarland, et al., Pyrimidines. V. Synthesis of 5-Amino-4-Hydroxypyrimidine, A New Isomer of Cystosine, Journal of the Chemical Society, (1952), pp. 4942-4945, Database Beilstein, Beilstein Instituted for Organic Chemistry, Database Accession No. BRN203399, (abstract).

\* cited by examiner

*Primary Examiner* — Craig Ricci

(57) ABSTRACT

The invention relates to oxazolopyrimidine compounds of formula (I), where A, $R^1$, $R^2$, $R^3$, $R^4$ and X are defined as stated in the claims. The compounds of formula I are suitable, for example, for wound healing.

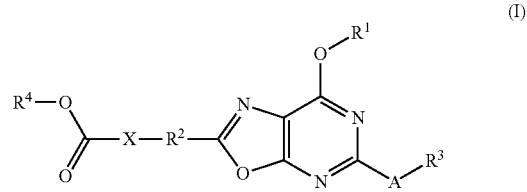

(I)

12 Claims, No Drawings

CARBOXYLIC ACID DERIVATIVES HAVING A 2,5,7-SUBSTITUTED OXAZOLOPYRIMIDINE RING

The present invention relates to carboxylic acid derivatives comprising a 2,5,7-substituted oxazolopyrimidine ring, and to physiologically compatible salts thereof.

Structurally similar compounds are already described in the prior art (see WO 2009/154775), which are suitable for treating multiple sclerosis. The mode of action of these compounds consists in causing a desensitization of the EDG-1 signal pathway by activating the EDG-1 receptor (so-called superagonism), which is then equivalent to a functional antagonism of the EDG-1 signal pathway. Systemically means that especially on lymphocytes, the EDG-1 signal pathway is permanently suppressed, as a result of which these cells can no longer chemotactically follow the S1P gradient between blood and lymph fluid. This means that the affected lymphocytes can no longer leave the secondary lymphatic tissue (increased homing) and the number of freely circulating lymphocytes in the plasma is greatly reduced. This deficiency of lymphocytes in the plasma (lymphopenia) brings about immunosuppression which is obligatorily required for the mechanism of action of the EDG-1 receptor modulators described in WO 2009/154775.

The object of the present invention was to provide compounds which are suitable specifically for wound healing and in particular for the treatment of wound healing disorders in patients with diabetes. In addition, it was desirable to provide compounds which are suitable for the treatment of diabetic foot syndrome (DFS). Furthermore, it was desirable to achieve a reproducible activation of the EDG-1 receptor signal pathway which thereby permits, in pharmacological terms, a persistent activation of the EDG-1 signal pathway.

The present invention relates to oxazolopyrimidine compounds of the formula I,

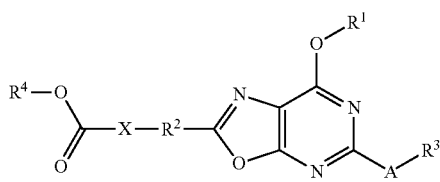

in which A, $R^1$, $R^2$, $R^3$, $R^4$ and X are defined as indicated below. The mechanism of action of the compounds of the formula I is not therefore based on desensitization of the EDG-1 signal pathway and is thus in diametral opposition to the mechanism of action described in WO 2009/154775. The invention furthermore relates to processes for the preparation of compounds of the formula I, their use, in particular as active ingredients in pharmaceuticals, and pharmaceutical compositions comprising them.

Compared with healthy people, patients with diabetes have delayed wound healing and an increased rate of infection, especially in the case of long-term hyperglycemia, caused for example by poor blood sugar regulation. The causes include circulation disorders, especially in the area of the small vessels, which lead to impaired oxygen and nutrient supply of the tissue. Moreover, the cell division and cell migration rate of keratinocytes, fibroblasts and dermal endothelial cells is reduced. Additionally, the activity of various defense cells (granulocytes) with reduced phagocytosis (engulfing and destruction of bacteria) is restricted. The function of the antibodies (immuno-globulins) against bacteria is also restricted in the event of high blood sugar values. Accordingly, wounds and infections in patients with diabetes have to be cared for in a particular way.

The Edg-1 receptor is a member of the endothelial differentiation gene (Edg) receptor family of currently eight identified class A GPCRs (G-protein coupled receptors). This family can be divided into subfamilies of sphingosine-1-phosphate (S1P)-activated receptors (five members) and receptors activated by lysophosphatidic acid (LPA; three members). The endogenous ligand S1P is a pluripotent lysophospholipid acting on different cell types by activating GPCRs from the Edg receptor family, namely Edg-1 (=S1P1), Edg-3 (=S1P3), Edg-5 (=S1P2), Edg-6 (=S1P4) and Edg-8 (S1P5). Although S1P is also described as an intracellular messenger, many cellular responses of S1P are mediated via the activation of Edg receptors. S1P is generated by the enzyme family of sphingosine kinases (SPHK) and degraded by different phosphatases or lyases.

A subject of the present invention is an oxazolopyrimidine compound of the formula I, in any of its stereoisomeric forms, or a mixture of stereoisomeric forms in any ratio, or a physiologically acceptable salt thereof, or a physiologically acceptable solvate of any of them,

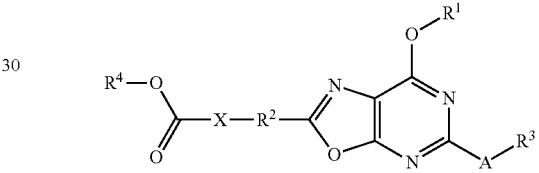

wherein

A is chosen from NH, O and S;

X is chosen from $(C_1\text{-}C_6)$-alkanediyl, $(C_2\text{-}C_6)$-alkenediyl, $(C_2\text{-}C_6)$-alkynediyl, $(C_3\text{-}C_7)$-cycloalkanediyl and $(C_1\text{-}C_6)$-alkanediyl-oxy, which all are optionally substituted by one or more identical or different substituents chosen from fluorine and hydroxy, wherein the oxygen atom of the $(C_1\text{-}C_6)$-alkanediyl-oxy group is bonded to the group $R^2$;

$R^1$ is chosen from $(C_1\text{-}C_6)$-alkyl, $(C_2\text{-}C_6)$-alkenyl, $(C_2\text{-}C_6)$-alkynyl, $(C_3\text{-}C_7)$-cycloalkyl-$C_tH_{2t}$— and Het-$C_tH_{2t}$—, wherein t is chosen from 0, 1, 2 and 3;

$R^2$ is chosen from phenylene and a divalent residue of an aromatic, 5-membered to 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenylene and divalent residue of an aromatic heterocycle are optionally substituted on one or more ring carbon atoms by identical or different substituents $R^{22}$;

$R^3$ is chosen from $(C_1\text{-}C_6)$-alkyl, $(C_2\text{-}C_6)$-alkenyl, $(C_2\text{-}C_6)$-alkynyl, $(C_3\text{-}C_7)$-cycloalkyl-$C_uH_{2u}$— and Het-$C^vH_{2v}$—, wherein u and v are chosen from 1 and 2, or $R^3$ is a residue of a saturated or unsaturated, 3-membered to 10-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a $(C_1\text{-}C_4)$-alkyl substituent and one or two of the ring sulfur atoms can carry one or two oxo groups, and wherein the residue of a ring is optionally substituted on one or more ring carbon atoms by identical or different substituents $R^{31}$, provided that $R^3$ cannot be $(C_1\text{-}C_6)$-alkyl if A is S;

$R^4$ is chosen from hydrogen, $(C_1-C_4)$-alkyl and $(C_3-C_7)$-cycloalkyl-$C_zH_{2z}$—, wherein z is chosen from 0, 1 and 2;

$R^{21}$ is chosen from $(C_1-C_4)$-alkyl, $(C_3-C_7)$-cycloalkyl-$C_wH_{2w}$— and oxy, wherein w is chosen from 0, 1 and 2;

$R^{22}$ is chosen from halogen, hydroxy, $(C_1-C_4)$-alkyl-, $(C_1-C_4)$-alkyloxy, $(C_1-C_4)$-alkyl-$S(O)_m$—, amino, nitro, cyano, hydroxycarbonyl, $(C_1-C_4)$-alkyloxycarbonyl, aminocarbonyl and aminosulfonyl;

$R^{31}$ is chosen from halogen, $(C_1-C_4)$-alkyl, $(C_3-C_7)$-cycloalkyl, hydroxy, $(C_1-C_4)$-alkyloxy, oxo, $(C_1-C_4)$-alkyl-$S(O)_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, aminosulfonyl, $(C_1-C_4)$-alkylaminosulfonyl and di$((C_1-C_4)$-alkyl)aminosulfonyl;

Het is a residue of a saturated, 4-membered to 7-membered, monocyclic heterocycle which comprises 1 or 2 identical or different ring heteroatoms chosen from N, O and S and which is bonded via a ring carbon atom, wherein the residue of a heterocycle is optionally substituted by one or more identical or different substituents chosen from fluorine and $(C_1-C_4)$-alkyl;

m is chosen from 0, 1 and 2, wherein all numbers m are independent of each other;

wherein all cycloalkyl and cycloalkanediyl groups, independently of each other and independently of any other substituents, are optionally substituted by one or more identical or different substituents chosen from fluorine and $(C_1-C_4)$-alkyl;

wherein all alkyl, alkanediyl, $C_tH_{2t}$, $C_uH_{2u}$, $C_vH_{2v}$, $C_wH_{2w}$, $C_zH_{2z}$, alkenyl, alkenediyl, alkynyl and alkynediyl groups, independently of each other and independently of any other substituents, are optionally substituted by one or more fluorine substituents.

Structural elements such as groups, substituents, hetero ring members, numbers or other features, for example alkyl groups, groups like $R^{22}$ or $R^{31}$, numbers like m, u and v, which can occur several times in the compounds of the formula I, can all independently of one another have any of the indicated meanings and can in each case be identical to or different from one another. For example, the alkyl groups in a dialkylamino group can be identical or different.

Alkyl, alkenyl and alkynyl groups can be linear, i.e. straight-chain, or branched. This also applies when they are part of other groups, for example alkyloxy groups (=alkoxy groups, alkyl-O-groups), alkyloxycarbonyl groups or alkyl-substituted amino groups, or when they are substituted. Depending on the respective definition, the number of carbon atoms in an alkyl group can be 1, 2, 3, 4, 5 or 6, or 1, 2, 3 or 4, or 1, 2 or 3. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, and hexyl including n-hexyl, 3,3-dimethylbutyl and isohexyl. Double bonds and triple bonds in alkenyl groups and alkynyl groups can be present in any positions. In one embodiment of the invention, alkenyl groups contain one double bond and alkynyl groups contain one triple bond. In one embodiment of the invention, an alkenyl group or alkynyl group contains at least three carbon atoms and is bonded to the remainder of the molecule via a carbon atom which is not part of a double bond or triple bond. Examples of alkenyl and alkynyl are ethenyl, prop-1-enyl, prop-2-enyl (=allyl), but-2-enyl, 2-methylprop-2-enyl, 3-methylbut-2-enyl, hex-3-enyl, hex-4-enyl, prop-2-ynyl (=propargyl), but-2-ynyl, but-3-ynyl, hex-4-ynyl or hex-5-ynyl. Substituted alkyl groups, alkenyl groups and alkynyl groups can be substituted in any positions, provided that the respective compound is sufficiently stable and is suitable for the desired purpose such as use as a drug substance. The prerequisite that a specific group and a compound of the formula I is sufficiently stable and suitable for the desired purpose such as use as a drug substance, applies in general with respect to the definitions of all groups in the compounds of the formula I.

As far as applicable, the preceding explanations regarding alkyl, alkenyl and alkynyl groups apply correspondingly to divalent alkyl groups such as the groups alkanediyl, $C_tH_{2t}$, $C_uH_{2u}$, $C_vH_{2v}$, $C_wH_{w2}$ and $C_zH_{2z}$ and divalent alkenyl groups and alkynyl groups such as the groups alkenediyl and alkynediyl, which thus can likewise be linear and branched. The double bonds and triple bonds in alkenediyl and alkynediyl groups can be present in any positions. In one embodiment of the invention, alkenediyl groups contain one double bond and alkynediyl groups contain one triple bond. Examples of divalent alkyl groups are —$CH_2$— (=methylene), —$CH_2$—$CH_2$—, —$CH_2$—$CH_2$—$CH_2$—, —$CH_2$—$CH_2$—$CH_2$—$CH_2$—, —$CH(CH_3)$—, —$C(CH_3)_2$—, —$CH(CH_3)$—$CH_2$—, —$CH_2$—$CH(CH_3)$—, —$C(CH_3)_2$—$CH_2$—, —$CH_2$—$C(CH_3)_2$—, examples of divalent alkenyl groups are —$CH=CH$—, —$CH_2$—$CH=CH$—, —$CH=CH$—$CH_2$—, —$CH_2$—$CH=CH$—$CH_2$—, —$CH_2$—$CH_2$—$CH=CH$—, —$C(CH_3)=C(CH_3)$—, and examples of divalent alkynyl groups are —$C\equiv C$—, —$CH_2$—$C\equiv C$—, —$C\equiv C$—$CH_2$—, —$C(CH_3)_2$—$C\equiv C$—, —$C\equiv C$—$C(CH_3)_2$—, —$CH_2$—$C\equiv C$—$CH_2$—, —$CH_2$—$CH_2$—$C\equiv C$—. If a number in a divalent group such as the number t in the group $C_tH_{2t}$, for example, is 0 (=zero), the two groups which are attached to the contemplated group, such as $C_tH_{2t}$, are directly connected to one another via a single bond.

The number of ring carbon atoms in a cycloalkyl group can be 3, 4, 5, 6 or 7. In one embodiment of the invention, the number of ring carbon atoms in a cycloalkyl group, independently of the number of ring carbon atoms in any other cycloalkyl group, is 3, 4, 5 or 6, in another embodiment 3, 4 or 5, in another embodiment 3 or 4, in another embodiment 3, in another embodiment 5, 6 or 7, in another embodiment 5 or 6, in another embodiment 6 or 7, in another embodiment 6. This applies accordingly to divalent cycloalkyl groups, i.e. cycloalkanediyl groups, which can be bonded to the adjacent groups via any one or two ring carbon atoms. Examples of cycloalkyl groups are cyclopropyl, cyclobutyl, cyclopentyl, cyclohexyl and cycloheptyl. Examples of divalent cycloalkyl groups are cyclopropane-1,1-diyl, cyclopropane-1,2-diyl, cyclobutane-1,3-diyl, cyclopentane-1,1-diyl, cyclopentane-1,2-diyl, cyclopentane-1,3-diyl, cyclohexane-1,1-diyl, cyclohexane-1,2-diyl, cyclohexane-1,3-diyl, cyclohexane-1,4-diyl, cycloheptane-1,4-diyl. Independently of one another and independently of any other substituents, cycloalkyl groups and cycloalkanediyl groups are optionally substituted by one or more identical or different $(C_1-C_4)$-alkyl substituents which can be located in any positions, i.e., cycloalkyl groups can be unsubstituted by alkyl substituents or substituted by alkyl substituents, for example by 1, 2, 3 or 4, or by 1 or 2, $(C_1-C_4)$-alkyl substituents, for example by methyl groups. Examples of alkyl-substituted cycloalkyl groups and cycloalkanediyl groups are 4-methylcyclohexyl, 4-tert-butylcyclohexyl or 2,3-dimethylcyclopentyl, 2,2-dimethylcyclopropane-1,1-diyl, 2,2-dimethylcyclopropane-1,2-diyl, 2,2-dimethylcyclopentane-1,3-diyl, 6,6-dimethylcycloheptane-1,4-diyl. Examples of cycloalkylalkyl groups, which can represent groups such as $(C_3-C_7)$-cycloalkyl-$C_tH_{2t}$—, for example, are cyclopropylmethyl, cyclobutylmethyl, cyclopentylmethyl, cyclohexylmethyl, cycloheptylmethyl, 1-cyclopropylethyl, 2-cyclopropylethyl, 1-cyclobutylethyl, 2-cyclobutylethyl, 2-cyclopentylethyl, 2-cyclohexylethyl, 2-cycloheptylethyl.

Independently of one another and independently of any other substituents, alkyl groups, divalent alkyl groups, alkenyl groups, divalent alkenyl groups, alkynyl groups, divalent alkynyl groups, cycloalkyl groups and divalent cycloalkyl groups are optionally substituted by one or more fluorine substituents which can be located in any positions, i.e., the said groups can be unsubstituted by fluorine substituents or substituted by fluorine substituents, for example by 1, 2, 3, 4, 5, 6, 7, 8, 9, 10, 11, 12 or 13, or by 1, 2, 3, 4, 5, 6, 7, 8 or 9, or by 1, 2, 3, 4, 5, 6 or 7, or by 1, 2, 3, 4 or 5, or by 1, 2 or 3, or by 1 or 2, fluorine substituents. Examples of fluorine-substituted groups of this type are trifluoromethyl, 2-fluoroethyl, 2,2,2-trifluoroethyl, pentafluoroethyl, 3,3,3-trifluoropropyl, 2,2,3,3,3-pentafluoropropyl, 4,4,4-trifluorobutyl, heptafluoroisopropyl, —CHF—, —CF$_2$—, —CF$_2$—CH$_2$—, —CH$_2$—CF$_2$—, —CF$_2$—CF$_2$—, —CF(CH$_3$)—, —C(CF$_3$)$_2$—, 1-fluorocyclopropyl, 2,2-difluorocyclopropyl, 3,3-difluorocyclobutyl, 1-fluorocyclohexyl, 4,4-difluorocyclohexyl, 3,3, 4,4,5,5-hexafluorocyclohexyl, 2,2-difluorocyclopropane-1, 2-diyl. Examples of alkyloxy groups in which the alkyl moiety is fluorine-substituted, are trifluoromethoxy, 2,2,2-trifluoroethoxy, pentafluoroethoxy and 3,3,3-trifluoropropoxy. In one embodiment of the invention, the total number of fluorine substituents and (C$_1$-C$_4$)-alkyl substituents, which independently of any other substituents are optionally present on cycloalkyl groups and cycloalkanediyl groups in the compounds of the formula I, is 1, 2, 3, 4, 5, 6, 7, 8, 9, 10 or 11, in another embodiment 1, 2, 3, 4, 5, 6, 7, 8 or 9, in another embodiment 1, 2, 3, 4 or 5, in another embodiment 1, 2, 3 or 4.

Groups like phenyl, naphthyl (=naphthalenyl) and residues of aromatic heterocycles which are optionally substituted by one or more substituents, can be unsubstituted or substituted, for example by 1, 2, 3, 4 or 5, or by 1, 2, 3 or 4, or by 1, 2 or 3, or by 1 or 2, or by 1, identical or different substituents which can be located in any positions. In one embodiment of the invention the total number of nitro substituents in a compound of the formula I is not greater than two. Aromatic nitrogen heterocycles which in the parent ring system carry a hydrogen atom on a ring nitrogen atom in a 5-membered ring, such as a pyrrole, imidazole, indole or benzoimidazole ring, for example, can be substituted on the carbon atoms and/or on such ring nitrogen atoms. In one embodiment of the invention, substituents on such ring nitrogen atoms are chosen from (C$_1$-C$_4$)-alkyl groups, i.e. such ring nitrogen atoms in aromatic heterocycles carry a hydrogen atom or a (C$_1$-C$_4$)-alkyl substituent. When it is stated with respect to ring nitrogen atoms in aromatic heterocycles and any other heterocycles that they can carry a hydrogen atom or a substituent, such ring nitrogen atoms either carry a hydrogen atom or a substituent, or they do not carry a hydrogen atom or substituent. Ring nitrogen atoms which carry a hydrogen atom or a substituent, occur in a nitrogen-containing aromatic 5-membered ring as is present in pyrrole, imidazole, indole or benzoimidazole, for example, and in a non-aromatic ring including a saturated ring. Ring nitrogen atoms which do not carry a hydrogen atom or a substituent unless they are present in positively charged form, including any further ring nitrogen atoms in addition to ring nitrogen atoms which carry a hydrogen atom or a substituent, occur in an aromatic ring as is present in thiazole, imidazole, pyridine or benzoimidazole, for example, and in a non-aromatic ring in which they are bridgehead atoms or are part of a double bond, and they occur as ring nitrogen atoms via which a ring is bonded. Suitable ring nitrogen atoms in aromatic heterocycles in the compounds of the formula I, such as the ring nitrogen atom in a pyridine ring, specifically a ring nitrogen atom in an aromatic heterocycle representing R$^2$, can also carry an oxy substituent —O$^-$ and be present as an N-oxide, and such ring nitrogen atoms can also be present as quaternary salt, for example as N—(C$_1$-C$_4$)-alkyl salt such as N-methyl salt, wherein in one embodiment of the invention the counter anion in such a quaternary salt is a physiologically acceptable anion which is derived from an acid that forms a physiologically acceptable salt. In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. Naphthyl can be 1-naphthyl (=naphthalen-1-yl) or 2-naphthyl (=naphthalen-2-yl). In monosubstituted 1-naphthyl groups, the substituent can be located in the 2-, 3-, 4-, 5-, 6-, 7- or 8-position. In monosubstituted 2-naphthyl groups, the substituent can be located in the 1-, 3-, 4-, 5-, 6-, 7- or 8-position. In disubstituted naphthyl groups, the substituents can likewise be located in any positions both in the ring via which the naphthyl group is bonded and/or in the other ring. This statement relating to the monovalent residues applies accordingly to the respective divalent residues, such as phenylene groups representing R$^2$, for example, which thus can likewise be unsubstituted or substituted, for example by 1, 2, 3 or 4, or by 1, 2 or 3, or by 1 or 2, or by 1, identical or different substituents which can be located in any positions.

In residues of aromatic heterocycles representing R$^2$ or R$^3$, which may be designated as heteroaryl and heteroarylene groups, as well as in all other heterocyclic rings in the compounds of the formula I including the group Het and non-aromatic heterocyclic groups representing R$^3$, the ring heteroatoms are generally chosen from N, O and S, wherein N includes ring nitrogen atoms which carry a hydrogen atom or a substituent as well as ring nitrogen atoms which do not carry a hydrogen atom or a substituent. Ring heteroatoms can be located in any positions, provided that the heterocyclic system is known in the art and is stable and suitable as a subgroup for the desired purpose of the compound of the formula I such as use as a drug substance. In one embodiment of the invention, two ring oxygen atoms cannot be present in adjacent ring positions of a heterocycle, in another embodiment two ring heteroatoms chosen from oxygen and sulfur cannot be present in adjacent ring positions of any heterocycle. Saturated rings do not contain a double bond within the ring. Unsaturated ring systems can be aromatic or partially unsaturated including partially aromatic, in which latter case one ring in a bicyclic ring system is aromatic and the ring system is bonded via an atom in the non-aromatic ring. Depending on the respective group, unsaturated rings can contain one, two, three, four or five double bonds within the ring. Aromatic groups contain a cyclic system of six or ten delocalized pi electrons in the ring. Depending on the respective group, saturated and non-aromatically unsaturated heterocyclic rings, including Het and non-aromatic groups representing R$^3$, can be 3-membered, 4-membered, 5-membered, 6-membered, 7-membered, 8-membered, 9-membered or 10-membered. In one embodiment of the invention, aromatic heterocyclic rings are 5-membered or 6-membered monocyclic rings or 8-membered, 9-membered or 10-membered bicyclic rings, in another embodiment 5-membered or 6-membered monocyclic rings or 9-membered or 10-membered bicyclic rings, in another embodiment 5-membered or 6-membered monocyclic rings, wherein the 8-membered, 9-membered or 10-membered bicyclic rings are composed of two fused 5-membered rings, a 5-membered ring and a 6-membered ring which are fused to one another, and two fused 6-membered rings, respectively. In bicyclic aromatic heterocyclic groups, one or both rings can contain hetero ring members, and one or both rings can be aromatic. In general, bicyclic ring systems containing an aromatic ring and a non-aromatic ring are regarded as aromatic when they are bonded via a carbon atom in the aromatic ring, and as non-aromatic when they are bonded via a carbon atom in the non-aromatic ring. Unless stated otherwise, heterocyclic groups including aromatic heterocyclic groups can be bonded via any suitable ring carbon atom and, in the case of nitrogen heterocycles, via any suitable ring nitrogen atom. In one embodiment of the invention, an aromatic heterocyclic group in a compound of the formula I, independently of any other aromatic heterocyclic group, is bonded via a ring carbon atom, in another embodiment via a ring nitrogen atom. Depending on the definition of the respective heterocyclic group, in one embodiment of the invention the number of ring heteroatoms which can be present in a heterocyclic group, independently of the number of ring heteroatoms in another heterocyclic group, is 1, 2, 3 or 4, in another embodiment 1, 2 or 3, in another embodiment 1 or 2, in another embodiment 1, wherein the ring heteroatoms can be identical or different. Heterocyclic groups which are optionally substituted, can independently of any other heterocyclic group be unsubstituted or substituted by one or more identical or different substituents, for example by 1, 2, 3, 4 or 5, or by 1, 2, 3 or 4, or by 1, 2 or 3, or by 1 or 2, or by 1 substituents, which are indicated in the definition of the respective group. Substituents on heterocyclic groups can be located in any positions. For example, in a pyridin-2-yl group substituents can be located in the 3-position and/or 4-position and/or 5-position and/or 6-position, in a pyridin-3-yl group substituents can be located in the 2-position and/or 4-position and/or 5-position and/or 6-position, and in a pyridin-4-yl group substituents can be located in the 2-position and/or 3-position and/or 5-position and/or 6-position.

Examples of parent heterocycles, from which heterocyclic groups including aromatic heterocyclic groups, saturated heterocyclic groups and non-aromatic unsaturated heterocyclic groups can be derived, are azete, oxete, pyrrole, furan, thiophene, imidazole, pyrazole, [1,3]dioxole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, tetrazole, pyridine, pyran, thiopyran, pyridazine, pyrimidine, pyrazine, [1,3]oxazine, [1,4]oxazine, [1,3]thiazine, [1,4]thiazine, [1,2,3]triazine, [1,3]dithiine, [1,4]dithiine, [1,2,4]triazine, [1,3,5]triazine, [1,2,4,5]tetrazine, azepine, [1,3]diazepine, [1,4]diazepine, [1,3]oxazepine, [1,4]oxazepine, [1,3]thiazepine, [1,4]thiazepine, azocine, azecine, cyclopenta[b]pyrrole, 2-azabicyclo[3.1.0]hexane, 3-azabicyclo[3.1.0]hexane, 2-oxa-5-azabicyclo[2.2.1]heptane, indole, isoindole, benzothiophene, benzofuran, [1,3]benzodioxole (=1,2-methylenedioxybenzene), [1,3]benzoxazole, [1,3]benzothiazole, benzoimidazole, thieno[3,2-c]pyridine, chromene, isochromene, [1,4]benzodioxine, [1,4]benzoxazine, [1,4]benzothiazine, quinoline, isoquinoline, cinnoline, quinazoline, quinoxaline, phthalazine, thienothiophene, [1,8]naphthyridine and other naphthyridines, pteridine, and, the respective saturated and partially unsaturated heterocycles in which one or more, for example one, two, three, four or all double bonds within the ring system including double bonds in the aromatic ring are replaced with single bonds, such as azetidine, oxetane, pyrrolidine, tetrahydrofuran, tetrahydrothiophene, imidazolidine, oxazolidine, thiazolidine, dihydropyridine, piperidine, tetrahydropyran, piperazine, morpholine, thiomorpholine, azepane, chroman, isochroman, [1,4]benzodioxane (=1,2-ethylenedioxybenzene), 2,3-dihydrobenzofuran, 1,2,3,4-tetrahydroquinoline, 1,2,3,4-tetrahydroisoquinoline, for example.

Examples of residues of aromatic heterocycles, which can occur in the compounds of the formula I, are thiophenyl (=thienyl) including thiophen-2-yl and thiophen-3-yl, pyridinyl (=pyridyl) including pyridin-2-yl (=2-pyridyl), pyridin-3-yl(=3-pyridyl) and pyridin-4-yl(=4-pyridyl), imidazolyl including, for example, 1H-imidazol-1-yl, 1H-imidazol-2-yl, 1H-imidazol-4-yl and 1H-imidazol-5-yl, [1,2,4]triazolyl including 1H-[1,2,4]-triazol-1-yl and 4H-[1,2,4]-triazol-3-yl, tetrazolyl including 1H-tetrazol-1-yland 1H-tetrazol-5-yl, quinolinyl (=quinolyl) including quinolin-2-yl, quinolin-3-yl, quinolin-4-yl, quinolin-5-yl, quinolin-6-yl, quinolin-7-yl and quinolin-8-yl, which all are optionally substituted as indicated in the definition of the respective group. Examples of residues of saturated and partially unsaturated heterocycles, which can occur in the compounds of the formula I, are azetidinyl, pyrrolidinyl including pyrrolidin-1-yl, pyrrolidin-2-yl and pyrrolidin-3-yl, 2,5-dihydro-1H-pyrrolyl, piperidinyl including piperidin-1-yl, piperidin-2-yl, piperidin-3-yl and piperidin-4-yl, 1,2,3,4-tetrahydropyridinyl, 1,2,5,6-tetrahydropyridinyl, 1,2-dihydropyridinyl, azepanyl, azocanyl, azecanyl, octahydrocyclopenta[b]pyrrolyl, 2,3-dihydrobenzofuranyl including 2,3-dihydrobenzofuran-7-yl, 2,3-dihydro-1H-indolyl, octahydro-1H-indolyl, 2,3-dihydro-1H-isoindolyl, octahydro-1H-isoindolyl, 1,2-dihydroquinolinyl, 1,2,3,4-tetrahydroquinolinyl, decahydroquinolinyl, 1,2-dihydroisoquinolinyl, 1,2,3,4-tetrahydroisoquinolinyl, 1,2,3,4-tetrahydroisoquinolinyl, decahydroisoquinolinyl, decahydroisoquinolinyl, 4,5,6,7-tetrahydrothieno[3,2-c]pyridinyl, pyrazolidinyl, imidazolidinyl, hexahydropyrimidinyl, 1,2-dihydropyrimidinyl, piperazinyl, [1,3]diazepanyl, [1,4]diazepanyl, oxazolidinyl, [1,3]oxazinanyl, [1,3]oxazepanyl, morpholinyl including morpholin-2-yl, morpholin-3-yl and morpholin-4-yl, [1,4]oxazepanyl, thiazolidinyl, [1,3]thiazinanyl, thiomorpholinyl including thiomorpholin-2-yl, thiomorpholin-3-yl and thiomorpholin-4-yl, 3,4-dihydro-2H-[1,4]thiazinyl, [1,3]thiazepanyl, [1,4]thiazepanyl, [1,4]thiazepanyl, oxetanyl, tetrahydrofuranyl, tetrahydrothienyl, isoxazolidinyl, isothiazolidinyl, oxazolidinyl, [1,2,4]-oxadiazolidinyl, [1,2,4]-thiadiazolidinyl, [1,2,4]triazolidinyl, [1,3,4]oxadiazolidinyl, [1,3,4]thiadiazolidinyl, [1,3,4]triazolidinyl, 2,3-dihydrofuranyl, 2,5-dihydrofuranyl, 2,3-dihydrothienyl, 2,5-dihydrothienyl, 2,3-dihydropyrrolyl, 2,3-dihydroisoxazolyl, 4,5-dihydroisoxazolyl, 2,5-dihydroisoxazolyl, 2,3-dihydroisothiazolyl, 4,5-dihydroisothiazolyl, 2,5-dihydroisothiazolyl, 2,3-dihydropyrazolyl, 4,5-dihydropyrazolyl, 2,5-dihydropyrazolyl, 2,3-dihydrooxazolyl, 4,5-dihydrooxazolyl, 2,5-dihydrooxazolyl, 2,3-dihydrothiazolyl, 4,5-dihydrothiazolyl, 2,5-dihydrothiazolyl, 2,3-dihydroimidazolyl, 4,5-dihydroimidazolyl, 2,5-dihydroimidazolyl, tetrahydropyridazinyl, tetrahydropyrimidinyl, tetrahydropyrazinyl, tetrahydro[1,3,5]triazinyl, [1,3]dithianyl, tetrahydropyranyl, tetrahydrothiopyranyl, [1,3]dioxolanyl, 3,4,5,6-tetrahydropyridinyl, 4H-[1,3]thiazinyl, 1,1-dioxo-2,3,4,5-tetrahydrothienyl, 2-azabicyclo[3.1.0]hexyl including 2-azabicyclo[3.1.0]hex-2-yl, 3-azabicyclo[3.1.0]hexyl including 3-azabicyclo[3.1.0]hex-3-yl, 2-oxa-5-azabicyclo[2.2.1]-heptyl including 2-oxa-5-azabicyclo[2.2.1]-hept-5-yl, which all are bonded via a suitable ring carbon atom or ring nitrogen atom and are optionally substituted as indicated in the definition of the respective group.

Halogen is fluorine, chlorine, bromine or iodine. In one embodiment of the invention, any halogen in a compound of the formula I is independently of any other halogen chosen from fluorine, chlorine and bromine, in another embodiment from fluorine and chlorine.

When an oxo group is bonded to a carbon atom, it replaces two hydrogen atoms on a carbon atom of the parent system. Thus, if a $CH_2$ group in a chain or a ring is substituted by oxo, i.e. by a doubly bonded oxygen atom, it becomes a C(O) (=C(=O)) group. Evidently, an oxo group cannot occur as a substituent on a carbon atom in an aromatic ring such as in a phenyl group, for example. When a ring sulfur atom in a heterocyclic group can carry one or two oxo groups, it is a non-oxidized sulfur atom S if it does not carry any oxo group, or it is an S(O) group (=sulfoxide group, S-oxide group) if it carries one oxo group, or it is an $S(O)_2$ group (=sulfone group, S,S-dioxide group) if it carries two oxo groups.

The present invention includes all stereoisomeric forms of the compounds of the formula I and their salts and solvates. With respect to each chiral center, independently of any other chiral center, the compounds of the formula I can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings such as cycloalkyl rings, the invention includes both the E form and Z form, or the cis form and the trans form, as well as mixtures of these forms in all ratios. In one embodiment of the invention, a compound which can occur in two or more stereoisomeric forms is a pure, or substantially pure, individual stereoisomer. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally, a derivatization can be carried out before a separation of stereoisomers. The separation of a mixture of stereoisomers can be carried out at the stage of the compound of the formula I or at the stage of a starting material or an intermediate during the synthesis. The present invention also includes all tautomeric forms of the compounds of the formula I and their salts and solvates.

If the compounds of the formula I contain one or more acidic and/or basic groups, i.e. salt-forming groups, the invention also includes their corresponding physiologically or toxicologically acceptable salts, i.e. non-toxic salts, in particular their pharmaceutically acceptable salts. Thus, the compounds of the formula I which contain an acidic group, such as a hydroxycarbonyl group (=carboxy group=C(O)— OH group), can be present on such groups, and can be used according to the invention, as alkali metal salts, alkaline earth metal salts or as ammonium salts, for example. More specific examples of such salts are sodium salts, potassium salts, calcium salts, magnesium salts, quaternary ammonium salts such as tetraalkylammonium salts, or acid addition salts with ammonia or organic amines such as, for example, ethylamine, ethanolamine, triethanolamine or amino acids. Compounds of the formula I which contain a basic group, i.e. a group which can be protonated such as an amino group or a nitrogen heterocycle, can be present on such groups, and can be used according to the invention, in the form of their addition salts with inorganic and organic acids. Examples of suitable acids are hydrogen chloride, hydrogen bromide, phosphoric acid, sulfuric acid, methanesulfonic acid, oxalic acid, acetic acid, trifluoroacetic acid, tartaric acid, lactic acid, benzoic acid, malonic acid, fumaric acid, maleic acid, citric acid, and other acids known to the person skilled in the art. If a compound of the formula I simultaneously contains an acidic group and a basic group in the molecule, the invention also includes, in addition to the salt forms mentioned, inner salts (=betaines, zwitterions). The salts of the compounds of the formula I can be obtained by customary methods which are known to the person skilled in the art, for example by contacting the compound of the formula I with an organic or inorganic acid or base in a solvent or diluent, or by anion exchange or cation exchange from another salt. The invention also includes all salts of the compounds of the formula I which, owing to low physiological compatibility of the salt-forming acid or base, are not directly suitable for use in pharmaceuticals but which can be used, for example, as intermediates for chemical reactions or for the preparation of physiologically acceptable salts.

The present invention includes all solvates of compounds of the formula I, for example hydrates or adducts with alcohols such as ($C_1$-$C_4$)-alkanols, active metabolites of the compounds of the formula I, and also prodrugs and derivatives of the compounds of the formula I which in vitro do not necessarily exhibit pharmacological activity but which in vivo are converted into pharmacologically active compounds, for example esters or amides of carboxylic acid groups.

In one embodiment of the invention, A is chosen from NH and O, in another embodiment, A is chosen from NH and S, in another embodiment A is chosen from O and S, in another embodiment A is NH, in another embodiment A is O, in another embodiment A is S.

The alkanediyl, alkenediyl and alkynediyl groups occurring in the group X can be linear or branched, as already indicated with respect to such groups in general, and these groups as well as cycloalkanediyl groups representing X can be bonded to the adjacent groups, i.e. to the group $R^4$O—C (O) and to the group $R^2$ or, in the case of the group alkanediyl-oxy, to the oxygen atom of the alkanediyl-oxy group via any positions. The adjacent groups can be bonded to the same carbon atom or to different carbon atoms in the group X. In one embodiment, the chain of carbon atoms in an alkanediyl, alkenediyl and alkynediyl groups occurring in the group X which directly connects the group $R^4$O—C(O) to the group $R^2$ or, in the case of the group alkanediyl-oxy, to the oxygen atom of the alkanediyl-oxy group, consists of 1, 2, 3 or 4 carbon atoms, in another embodiment of 1, 2 or 3 carbon atoms, in another embodiment of 1 or 2 carbon atoms, in another embodiment of 1 carbon atom. In the case of a cycloalkanediyl group representing X, in one embodiment the groups $R^4$O—C(O) and $R^2$ are bonded to two ring carbon atoms which are in 1,2-position, 1,3-position or 1,4-position with respect to each other, in another embodiment in 1,2-position or 1,3-position with respect to each other, in another embodiment in 1,2-position with respect to each other, in another embodiment in 1,4-position with respect to each other. In one embodiment, X is chosen from ($C_1$-$C_6$)-alkanediyl, ($C_2$-$C_6$)-alkenediyl, ($C_3$-$C_7$)-cycloalkanediyl and ($C_1$-$C_6$)-alkanediyl-oxy, in another embodiment from ($C_1$-$C_6$)-alkanediyl, ($C_2$-$C_6$)-alkenediyl and ($C_1$-$C_6$)-alkanediyl-oxy, in another embodiment from ($C_1$-$C_6$)-alkanediyl, ($C_3$-$C_7$)-cycloalkanediyl and ($C_1$-$C_6$)-alkanediyl-oxy, in one embodiment from ($C_1$-$C_6$)-alkanediyl and ($C_1$-$C_6$)-alkanediyl-oxy, in another embodiment from $(C_1-C_6)$-alkanediyl, $(C_2-C_6)$-alkenediyl, $(C_2-C_6)$-alkynediyl and $(C_3-C_7)$-cycloalkanediyl, in another embodiment from $(C_1-C_6)$-alkanediyl, $(C_2-C_6)$-alkenediyl and $(C_3-C_7)$-cycloalkanediyl, in another embodiment from $(C_1-C_6)$-alkanediyl and $(C_2-C_6)$-alkenediyl, in another embodiment X is $(C_1-C_6)$-alkanediyl, in another embodiment X is $(C_2-C_6)$-alkenediyl, in another embodiment X is $(C_3-C_7)$-cycloalkanediyl, and in another embodiment X is $(C_1-C_6)$-alkanediyl-oxy, which all are optionally substituted as indicated. In one embodiment a $(C_1-C_6)$-alkanediylgroup occurring in X is a $(C_1-C_4)$-alkanediyl group, in another embodiment a $(C_1-C_3)$-alkanediyl group, in another embodiment a $(C_1-C_2)$-alkanediyl group. In one embodiment, the $(C_2-C_6)$-alkenediyl and $(C_2-C_6)$-alkynediyl groups representing X are $(C_2-C_4)$-alkenediyl and $(C_2-C_4)$-alkynediyl groups, in another embodiment $(C_2-C_3)$-alkenediyl and $(C_2-C_3)$-alkynediyl groups. In one embodiment, a $(C_3-C_7)$-cycloalkanediylgroup representing X is a $(C_3-C_6)$-cycloalkanediyl group, in another embodiment a $(C_3-C_4)$-cycloalkanediyl group, in another embodiment a cyclopropanediyl group, in another embodiment a cyclohexanediyl group. Examples of groups X from which the respective group representing X can be chosen in the afore-mentioned embodiments, or from which X can be chosen in another embodiment of the invention, are methylene, —CH(CH₃)— (ethane-1,1-diyl), —CH₂—CH₂— (ethane-1,2-diyl, 1,2-ethylene), —C(CH₃)₂— (1-methyl-ethane-1,1-diyl), —CH₂—CH₂—CH₂— (propane-1,3-diyl, 1,3-propylene), —CH₂—CH(CH₃)— and —CH(CH₃)—CH₂— (propane-1,2-diyl, 1,2-propylene), which exemplify the group $(C_1-C_6)$-alkanediyl, —CH=CH— (ethene-1,2-diyl), —CH=CH—CH₂— and —CH₂—CH=CH— (prop-1-ene-1,3-diyl and prop-2-ene-1,3-diyl) and —CH=C(CH₃)— and —C(CH₃)=CH— (prop-1-ene-1,2-diyl) which exemplify the group $(C_2-C_6)$-alkenediyl, —C≡C— (ethynediyl) and —CH₂—C≡C— and —C≡C—CH₂— (prop-1-yne-1,3-diyl and prop-2-yne-1,3-diyl) which exemplify the group $(C_2-C_6)$-alkynediyl, cyclopropane-1,1-diyl, cyclopropane-1,2-diyl and cyclohexane-1,4-diyl which exemplify the group $(C_3-C_7)$-cycloalkanediyl, —CH₂—O— (methylene-oxy), —CH₂—CH₂—O— (ethane-1,2-diyl-oxy), —CH(CH₃)—O— (ethane-1,1-diyl-oxy), —C(CH₃)₂—O— (1-methyl-ethane-1,1-diyl-oxy), —CH₂—CH₂—CH₂—O— (propane-1,3-diyl-oxy) and —CH₂—CH₂—CH₂—CH₂—O— (butane-1,4-diyl-oxy) which exemplify the group $(C_1-C_6)$-alkanediyl-oxy, all of which groups are optionally substituted as indicated. Thus, in one embodiment X is chosen from —CH₂—O—, —CH₂—CH₂—O—, —CH(CH₃)—O— and —C(CH₃)₂—O—, in another embodiment from —CH₂—O—, —CH₂—CH₂—O— and —CH(CH₃)—O—, in another embodiment from —CH₂—O— and —CH(CH₃)—O—, and in another embodiment X is —CH₂—O—, all of which groups are optionally substituted as indicated, and in which the oxygen atom is bonded to the group $R^2$. In one embodiment, the number of substituents which are optionally present in X, is 1, 2, 3 or 4, in another embodiment 1, 2 or 3, in another embodiment 1 or 2, in another embodiment 1, and in another embodiment the group X is not substituted by substituents chosen from fluorine and hydroxy. In one embodiment, the number of hydroxy substituents in X is not greater than 2, in another embodiment not greater than 1. In one embodiment, no more than one hydroxy substituent is present on an individual carbon atom in X. In one embodiment, hydroxy substituents are not present on carbon atoms which are part of a double bond in the group $(C_2-C_6)$-alkenediyl. In one embodiment, hydroxy substituents are not present on the carbon atom in the group $(C_1-C_6)$-alkanediyl-oxy which is bonded to the oxygen atom, in another embodiment no substituents are present on the carbon atom in the group $(C_1-C_6)$-alkanediyl-oxy which is bonded to the oxygen atom, i.e. in this last-mentioned embodiment all carbon atoms which are not linked to the said oxygen atom are optionally substituted by one or more identical or different substituents chosen from fluorine and hydroxy. The double bond in the group $(C_2-C_6)$-alkenediyl can have E configuration or Z configuration. In one embodiment it has E configuration, in another embodiment it has Z configuration.

In another embodiment of the invention, the number t is chosen from 0, 1 or 2, in another embodiment from 0 or 1, in another embodiment from 1, 2 or 3, in another embodiment from 1 or 2, in another embodiment t is 0, in another embodiment t is 1. In one embodiment, $R^1$ is chosen from $(C_1-C_6)$-alkyl, $(C_3-C_7)$-cycloalkyl-$C_tH_{2t}$— and Het-$C_tH_{2t}$—, in another embodiment from $(C_1-C_6)$-alkyl and $(C_3-C_7)$-cycloalkyl-$C_tH_{2t}$—, in another embodiment $R^1$ is $(C_1-C_6)$-alkyl, in another embodiment $R^1$ is $(C_3-C_7)$-cycloalkyl-$C_tH_{2t}$—, and in another embodiment $R^1$ is Het-$C_tH_{2t}$. In one embodiment $R^1$ is $(C_3-C_7)$-cycloalkyl-$C_tH_{2t}$— wherein t is chosen from 0, 1 and 2, in another embodiment $R^1$ is $(C_3-C_7)$-cycloalkyl-$C_tH_{2t}$— wherein t is chosen from 0 and 1, in another embodiment. $R^1$ is $(C_3-C_7)$-cycloalkyl-CH₂—, in another embodiment $R^1$ is $(C_3-C_7)$-cycloalkyl, in another embodiment $R^1$ is Het-$C_tH_{2t}$— wherein t is chosen from 0, 1 and 2, in another embodiment $R^1$ is Het-$C_tH_{2t}$— wherein t is chosen from 0 and 1, in another embodiment $R^1$ is Het—CH₂—, in another embodiment $R^1$ is Het. In one embodiment, a $(C_1-C_6)$-alkyl group representing $R^1$ is $(C_2-C_6)$-alkyl, in another embodiment $(C_2-C_5)$-alkyl, in another embodiment $(C_3-C_5)$-alkyl. In one embodiment, a $(C_2-C_6)$-alkenyl group and a $(C_2-C_6)$-alkynyl group representing $R^1$ are $(C_3-C_6)$-alkenyl and $(C_3-C_6)$-alkynyl, in another embodiment $(C_3-C_4)$-alkenyl and $(C_3-C_4)$-alkynyl, respectively. In one embodiment, a $(C_3-C_7)$-cycloalkyl group present in $R^1$ is $(C_3-C_6)$-cycloalkyl, in another embodiment $(C_3-C_5)$-cycloalkyl, in another embodiment $(C_3-C_4)$-cycloalkyl, in another embodiment cyclopropyl. In one embodiment, a group Het representing $R^1$ is a 4-membered to 6-membered, in another embodiment a 4-membered to 5-membered, in another embodiment a 4-membered, saturated monocyclic heterocycle bonded via a ring carbon atom, which comprises 1 or 2 identical or different ring heteroatoms, in another embodiment 1 ring heteroatom, which are chosen from N, O and S, in another embodiment from O and S, and in another embodiment are O atoms. In one embodiment, a group Het representing $R^1$ is an oxetanyl group, for example an oxetan-3-yl group. In one embodiment, the number of substituents which are optionally present on a group Het representing $R^1$ is one, two or three, in another embodiment one or two, in another embodiment one, and in another embodiment such a group Het is unsubstituted. In one embodiment, a $(C_1-C_4)$-alkyl substituent occurring on a group Het representing $R^1$ is a methyl group.

In one embodiment of the invention, the number of ring heteroatoms in an aromatic heterocycle representing $R^2$ is 1 or 2, in another embodiment it is 1. In one embodiment of the invention, $R^2$ is chosen from phenylene and a divalent residue of an aromatic, 6-membered monocyclic heterocycle which comprises 1, 2 or 3 ring nitrogen atoms, in another embodiment 1 or 2 ring nitrogen atoms, in another embodiment 1 ring nitrogen atom, wherein one of the ring nitrogen atoms can carry a substituent $R^{21}$ which is oxy, i.e. wherein one of the ring nitrogen atoms can be oxidized to the N-oxide, and wherein the phenylene and the divalent residue of an aromatic heterocycle are optionally substituted on one or more ring carbon atoms by identical or different substituents $R^{22}$. In another embodiment, $R^2$ is phenylene, wherein the phenylene is optionally substituted on one or more ring atoms by identical or different substituents $R^{22}$, and in another embodiment $R^2$ is pyridinediyl, wherein the ring nitrogen atom can carry a substituent $R^{21}$ which is oxy, i.e. wherein the ring nitrogen atom can be oxidized to the N-oxide, and wherein the pyridinediyl is optionally substituted on one or more ring carbon atoms by identical or different substituents $R^{22}$. In another embodiment, $R^2$ is a divalent residue of an aromatic 5-membered heterocycle which comprises 1, 2 or 3 identical or different ring heteroatoms chosen from N, O and S, wherein one of the ring nitrogen atoms can carry a hydrogen atom or a substituent $R^{21}$, and wherein the divalent residue of an aromatic heterocycle is optionally substituted on one or more ring carbon atoms by identical or different substituents $R^{22}$. In one embodiment, a divalent residue of an aromatic heterocyclic group representing $R^2$ is chosen from furandiyl, thiophenediyl, oxazolediyl, thiazolediyl, pyridinediyl, pyridazinediyl, pyrimidinediyl and pyrazinediyl, in another embodiment from furandiyl, thiophenediyl, thiazolediyl, pyridinediyl, pyridazinediyl, pyrimidinediyl and pyrazinediyl, in another embodiment from furandiyl, thiophenediyl, pyridinediyl, pyridazinediyl, pyrimidinediyl and pyrazinediyl, in another embodiment from furandiyl, thiophenediyl, pyridinediyl and pyrimidinediyl, in another embodiment from furandiyl, thiophenediyl and pyridinediyl, which are all optionally substituted as indicated with respect to $R^2$.

The ring carbon atoms via which the phenylene group and the divalent residue of an aromatic heterocycle which group or residue represents $R^2$ are bonded to the oxazolopyrimidine ring and to the group X, can be in any positions. A phenylene group representing $R^2$ can be 1,2-phenylene, i.e. the oxazolopyrimidine ring and the group X can be bonded in 1,2-position, or ortho position, with respect to each another, it can be 1,3-phenylene, i.e. the oxazolopyrimidine ring and the group X can be bonded in 1,3-position, or meta position, with respect to each another, and it can be 1,4-phenylene, i.e. the oxazolopyrimidine ring and the group X can be bonded in 1,4-position, or para position, with respect to each another. In one embodiment, a phenylene group representing $R^2$ is chosen from 1,3-phenylene and 1,4-phenylene, in another embodiment it is 1,3-phenylene, and in another embodiment it is 1,4-phenylene, all of these groups being optionally substituted as indicated with respect to $R^2$. In one embodiment, $R^2$ is chosen from one or more of the groups phenylene, furan-2,5-diyl, thiophene-2,4-diyl, thiophene-2,5-diyl, pyridine-2,4-diyl, pyridine-2,5-diyl, pyridine-3,5-diyl, pyridine-2,6-diyl and pyrimidine-2,5-diyl, in another embodiment from the groups furan-2,5-diyl, thiophene-2,4-diyl, thiophene-2,5-diyl, pyridine-2,4-diyl, pyridine-2,5-diyl, pyridine-3,5-diyl, pyridine-2,6-diyl and pyrimidine-2,5-diyl, in another embodiment from pyridine-2,4-diyl, pyridine-2,5-diyl, pyridine-3,5-diyl and pyridine-2,6-diyl, in another embodiment from phenylene, pyridine-2,4-diyl, pyridine-2,5-diyl, pyridine-3,5-diyl and pyridine-2,6-diyl, which all are optionally substituted as indicated with respect to $R^2$. In one embodiment, the number of substituents $R^{22}$ which can optionally be present on ring carbon atoms in $R^2$, is 1, 2, 3, 4 or 5, in another embodiment 1, 2, 3 or 4, in another embodiment 1, 2 or 3, in another embodiment 1 or 2, in another embodiment 1. Ring carbon atoms in $R^2$ which do not carry a substituent $R^{22}$, carry a hydrogen atom.

In one embodiment of the invention, $R^3$ is chosen from $(C_1-C_6)$-alkyl, $(C_2-C_6)$-alkenyl and $(C_2-C_6)$-alkynyl, in another embodiment $R^3$ is $(C_1-C_6)$-alkyl, in another embodiment $R^3$ is $(C_2-C_5)$-alkyl, and in another embodiment $R^3$ is $(C_1-C_4)$-alkyl, provided that $R^3$ cannot be an alkyl group if A is S. In another embodiment $R^3$ is chosen from $(C_3-C_7)$-cycloalkyl-$C_uH_{2u}$— and Het-$C_vH_{2v}$—, in another embodiment $R^3$ is $(C_3-C_7)$-cycloalkyl-$C_uH_{2u}$—, and in another embodiment $R^3$ is Het-$C_vH_{2v}$—, wherein in this embodiment u and v independently of each other are chosen from 1 and 2. In one embodiment u is 1, in another embodiment u is 2. In one embodiments is 1, in another embodiment v is 2. In one embodiment, the group $(C_3-C_7)$-cycloalkyl-$C_uH_{2u}$— representing $R^3$ is chosen from cyclopropyl-$C_uH_{2u}$—, cyclobutyl-$C_uH_{2u}$— and cyclopentyl-$C_uH_{2u}$— and the group Het-$C_vH_{2v}$— representing $R^3$ is tetrahydrofuranyl-$C_vH_{2v}$—. In one embodiment, $R^3$ is chosen from cyclopropyl-$C_uH_{2u}$—, cyclobutyl-$C_uH_{2u}$— and cyclopentyl-$C_uH_{2u}$—.

In one embodiment, $R^3$ is chosen from $(C_3-C_7)$-cycloalkyl-$C_uH_{2u}$— and Het-$C_vH_{2v}$—, or $R^3$ is a residue of a saturated or unsaturated, 3-membered to 10-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a $(C_1-C_4)$-alkyl substituent and one or two of the ring sulfur atoms can carry one or two oxo groups, and wherein the residue of a ring is optionally substituted on one or more ring carbon atoms by identical or different substituents $R^{31}$, and in another embodiment $R^3$ is a residue of a saturated or unsaturated, 3-membered to 10-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a $(C_1-C_4)$-alkyl substituent and one or two of the ring sulfur atoms can carry one or two oxo groups, and wherein the residue of a ring is optionally substituted on one or more ring carbon atoms by identical or different substituents $R^{31}$. In one embodiment, the number of ring heteroatoms in the ring representing $R^3$ is 0, 1, 2 or 3, in another embodiment it is 0, 1 or 2, in another embodiment it is 0 or 1, in another embodiment it is 0, in another embodiment it is 1, 2, 3 or 4, in another embodiment it is 1, 2 or 3, in another embodiment it is 1 or 2, in another embodiment it is 1. The residue of the ring representing $R^3$ can thus be carbocyclic or heterocyclic. In one embodiment, the ring heteroatoms in $R^3$ are chosen from N and O, in another embodiment from N and S, in another embodiment from O and S, in another embodiment they are N, wherein ring nitrogen atoms can carry a hydrogen atom or a $(C_1-C_4)$-alkyl substituent as occurs in saturated or partially unsaturated heterocycles or in 5-membered aromatic rings in heterocycles such as pyrrole or benzoimidazole, for example, or not carry a hydrogen atom or a $(C_1-C_4)$-alkyl substituent as occurs in aromatic heterocycles such as imidazole or pyridine, for example. In a residue of a heterocycle representing $R^3$ which comprises one or more ring sulfur atoms, in one embodiment one of the ring sulfur atoms is non-oxidized or carries one or two oxo groups, and all other ring sulfur atoms are non-oxidized. The residue of a monocyclic or bicyclic ring representing $R^3$ can be bonded to the group A via any suitable ring carbon atom or ring nitrogen atom. In one embodiment it is bonded via a ring carbon atom, in another embodiment it is bonded via a ring carbon atom or, if A is NH, via a ring nitrogen atom, and in another embodiment it is bonded via a ring nitrogen atom. The residue of a monocyclic or bicyclic ring representing $R^3$ can be unsaturated and in this case contain 1, 2, 3, 4 or 5, or 1, 2, 3 or 4, or 1, 2 or 3, or 1 or 2, or 1, double bonds within the ring and can in any of the two rings be aromatic or non-aromatic, or it can be saturated and in this latter case contain no double bonds within the ring. In one embodiment, the residue of the ring representing $R^3$ is saturated or aromatic, in another embodiment it is saturated, and in another embodiment it is aromatic. In one embodiment, the residue of the 3-membered or 4-membered ring representing $R^3$ is saturated. If $R^3$ comprises ring nitrogen atoms which can carry a hydrogen atom or a $(C_1-C_4)$-alkyl substituent, one such ring nitrogen atom or two such ring nitrogen atoms can be present. In one embodiment, the number of optional substituents $R^{31}$ on ring carbon atoms in the ring representing $R^3$ is 1, 2, 3, 4, 5 or 6, in another embodiment 1, 2, 3, 4 or 5, in another embodiment 1, 2, 3 or 4, in another embodiment 1, 2 or 3, in another embodiment 1 or 2, in another embodiment 1.

The ring which can represent $R^3$ can be 3-membered, 4-membered, 5-membered, 6-membered, 7-membered, 8-membered, 9-membered or 10-membered. In one embodiment, $R^3$ is 4-membered to 10-membered, in another embodiment 4-membered to 9-membered, in another embodiment 4-membered to 8-membered, in another embodiment 4-membered to 7-membered, in another embodiment 5-membered to 7-membered, in another embodiment 5-membered or 6-membered, in another embodiment 6-membered, in another embodiment 8-membered to 10-membered, in another embodiment 9-membered to 10-membered. In one embodiment, a 3-membered ring representing $R^3$ does not comprise any ring heteroatoms. In one embodiment, $R^3$ is monocyclic, in another embodiment bicyclic. In one embodiment, a bicyclic group representing $R^3$ is at least 7-membered. Among others, the residue of a ring representing $R^3$ can be a cycloalkyl group, a phenyl group, a naphthyl group, a residue of an unsaturated, aromatic or non-aromatic heterocyclic group or a residue of a saturated heterocyclic group, which all are optionally substituted on ring carbon atoms and ring nitrogen atoms as specified with respect to $R^3$. As far as applicable, all explanations given above with respect to such groups apply correspondingly to $R^3$. Another example of groups which can represent $R^3$, are cycloalkenyl groups such as $(C_5-C_7)$-cycloalkenyl groups which can be bonded via any ring carbon atom and are optionally substituted as specified with respect to $R^3$. In one embodiment, optional substituents $R^{31}$ on a cycloalkenyl group representing $R^3$ are chosen from fluorine and $(C_1-C_4)$-alkyl. In one embodiment, cycloalkenyl groups contain one double bond within the ring which can be present in any position. Examples of cycloalkenyl are cyclopentenyl including cyclopent-1-enyl, cyclopent-2-enyl and cyclopent-3-enyl, cyclohexenyl including cyclohex-1-enyl, cyclohex-2-enyl and cyclohex-3-enyl, and cycloheptenyl including cyclohept-1-enyl, cyclohept-2-enyl, cyclopent-3-enyl and cyclohept-4-enyl. Examples of residues of rings, from which $R^3$ is chosen in one embodiment of the invention, are cyclopropyl, cyclobutyl, cyclopentyl, cyclohexyl, phenyl, oxetanyl including oxetan-3-yl, tetrahydrofuranyl including tetrahydrofuran-3-yl, tetrahydrothiophenyl including tetrahydrothiophen-3-yl, tetrahydropyranyl including tetrahydropyran-4-yl, azetidinyl including azetidin-1-yl, pyrrolidinyl, piperidinyl, imidazolidinyl, piperazinyl, morpholinyl including morpholin-1-yl, thiomorpholinyl, furanyl including furan-3-yl, thiophenyl including thiophen-3-yl, pyrazolyl including pyrazol-3-yl, imidazolyl, thiazolyl including thiazol-2-yl, pyridinyl including pyridin-2-yl, pyridin-3-yl and pyridin-4-yl, pyridazinyl including pyridazin-3-yl, wherein in all of them, insofar as applicable, one or two of the ring nitrogen atoms can carry a hydrogen atom or $(C_1-C_4)$-alkyl, and wherein all of them are optionally substituted on one or more ring carbon atoms by identical or different substituents $R^{31}$, and wherein in all of them, insofar as applicable, a ring sulfur atom can be non-oxidized, i.e. can be present as a sulfur atom, or can carry one or two oxo groups, i.e. can be present in the form of a sulfoxide or sulfone.

In one embodiment, $R^3$ is chosen from phenyl and a residue of a saturated or unsaturated 3-membered to 7-membered, monocyclic ring, in another embodiment from phenyl and a residue of a saturated or unsaturated 5-membered to 7-membered, monocyclic ring, in another embodiment from phenyl, pyridinyl and a residue of a saturated 3-membered to 7-membered, monocyclic ring, in another embodiment from phenyl, pyridinyl and a residue of a saturated 5-membered to 7-membered, monocyclic ring, in another embodiment from phenyl and a residue of a saturated 3-membered to 7-membered, monocyclic ring, in another embodiment from phenyl and a residue of a saturated 5-membered to 7-membered, monocyclic ring, wherein in all these embodiments the monocyclic ring comprises 1 or 2 identical or different ring heteroatoms chosen from N, O and S, wherein one or two of the ring nitrogen atoms can carry a hydrogen atom or a $(C_1-C_4)$-alkyl substituent and one or two of the ring sulfur atoms can carry one or two oxo groups, and wherein the phenyl, pyridinyl and residue of a ring are optionally substituted on one or more ring carbon atoms by identical or different substituents $R^{31}$, and wherein pyridinyl includes pyridin-2-yl, pyridin-3-yl and pyridin-4-yl. In one embodiment, $R^3$ is phenyl which is optionally substituted by one or more identical or different substituents $R^{31}$.

In one embodiment of the invention, the number z is chosen from 0 and 1, in another embodiment it is 0, in another embodiment it is 1. In one embodiment of the invention, the group $R^4$ is chosen from hydrogen and $(C_1-C_4)$-alkyl, in another embodiment $R^4$ is chosen from hydrogen, methyl, ethyl, n-propyl, n-butyl and isopropyl, in another embodiment from hydrogen, methyl and ethyl, in another embodiment $R^4$ is hydrogen, in another embodiment $R^4$ is $(C_1-C_4)$-alkyl, in another embodiment $R^4$ is methyl, and in another embodiment $R^4$ is ethyl. In one embodiment, a $(C_3-C_7)$-cycloalkyl group present in $R^4$ is $(C_3-C_6)$-cycloalkyl, in another embodiment it is cyclopropyl.

In one embodiment of the invention, the number w is chosen from 0 and 1, in another embodiment it is 0, in another embodiment it is 1. In one embodiment, a $(C_3-C_7)$-cycloalkyl group present in $R^{21}$ is $(C_3-C_6)$-cycloalkyl, in another embodiment $(C_3-C_6)$-cycloalkyl, in another embodiment cyclopropyl. In one embodiment, $R^{21}$ is chosen from $(C_1-C_4)$-alkyl and oxy, in another embodiment $R^{21}$ is $(C_1-C_4)$-alkyl, in another embodiment it is $(C_1-C_3)$-alkyl, in another embodiment it is methyl, and in another embodiment it is oxy.

In one embodiment of the invention, the substituents $R^{22}$ which are optionally present on the group $R^2$, are chosen from halogen, hydroxy, $(C_1-C_4)$-alkyloxy-, $(C_1-C_4)$-alkyl-$S(O)_m$—, amino, nitro and cyano, in another embodiment from halogen, hydroxy, $(C_1-C_4)$-alkyl-, $(C_1-C_4)$-alkyloxy-, amino and cyano, in another embodiment from halogen, hydroxy, $(C_1-C_4)$-alkyl- and $(C_1-C_4)$-alkyloxy-, in another embodiment from fluorine, chlorine, hydroxy, $(C_1-C_4)$-alkyl- and $(C_1-C_4)$-alkyloxy-, in another embodiment from fluorine, chlorine and $(C_1-C_4)$-alkyl-, and in another embodiment they are $(C_1-C_4)$-alkyl substituents.

In one embodiment, 1, 2 or 3 of the substituents $R^{22}$, in another embodiment 1 or 2 of the substituents $R^{22}$, and in another embodiment 1 of the substituents $R^{22}$, which are optionally present on the group $R^2$, are defined as in the general definition of $R^{22}$ and thus are chosen from halogen, hydroxy, $(C_1-C_4)$-alkyl-, $(C_1-C_4)$-alkyloxy-, $(C_1-C_4)$-alkyl-$S(O)_m$—, amino, nitro, cyano, hydroxycarbonyl, $(C_1-C_4)$-alkyloxycarbonyl, aminocarbonyl and aminosulfonyl, and any further substituents $R^{22}$ which are optionally present on the group $R^2$, for example 1, 2 or 3 further substituents $R^{22}$, or 1 or 2 further substituents $R^{22}$, or 1 further substituent $R^{22}$, are chosen from halogen, hydroxy, $(C_1$-$C_4)$-alkyloxy-, $(C_1$-$C_4)$-alkyl-$S(O)_m$—, amino, nitro and cyano, wherein all alkyl groups independently of each other are optionally substituted by one or more fluorine substituents as generally applies to alkyl groups. In one embodiment, the substituents $R^{22}$ which are optionally present on the group $R^2$ and which in the afore-mentioned embodiment are defined as in the general definition of $R^{22}$, for example 1 or 2 such substituents $R^{22}$, or 1 such substituent $R^{22}$, are chosen from halogen, hydroxy, $(C_1$-$C_4)$-alkyl-, $(C_1$-$C_4)$-alkyloxy-, $(C_1$-$C_4)$-alkyl-$S(O)_m$—, amino and cyano. In one embodiment, the substituents $R^{22}$ which are optionally present on the group $R^2$ and which in the afore-mentioned embodiment are defined as in the general definition of $R^{22}$, for example 1 or 2 such substituents $R^{22}$, or 1 such substituent $R^{22}$, are not located on ring carbon atoms within the group $R^2$ which is adjacent to the atom via which the group $R^2$ is bonded to the oxazolopyrimidine ring depicted in formula I. In one embodiment, the further substituents $R^{22}$ which are optionally present on the group $R^2$, for example 1, 2 or 3 further substituents $R^{22}$, or 1 or 2 further substituents $R^{22}$, or 1 further substituent $R^{22}$, are chosen from halogen, hydroxy, $(C_1$-$C_4)$-alkyloxy-, amino, cyano, in another embodiment from halogen, hydroxy, $(C_1$-$C_4)$-alkyl- and $(C_1$-$C_4)$-alkyloxy-, in another embodiment from halogen, $(C_1$-$C_4)$-alkyl- and $(C_1$-$C_4)$-alkyloxy-, in another embodiment from halogen and $(C_1$-$C_4)$-alkyl-, wherein in all these embodiments all alkyl groups independently of each other are optionally substituted by one or more fluorine substituents.

In one embodiment of the invention, $R^{31}$ is chosen from halogen, $(C_1$-$C_4)$-alkyl, $(C_3$-$C_7)$-cycloalkyl, hydroxy, $(C_1$-$C_4)$-alkyloxy, oxo, $(C_1$-$C_4)$-alkyl-$S(O)_m$—, amino, $(C_1$-$C_4)$-alkylamino, di$((C_1$-$C_4)$-alkyl)amino, $(C_1$-$C_4)$-alkylcarbonylamino, $(C_1$-$C_4)$-alkylsulfonylamino, cyano, $(C_1$-$C_4)$-alkylcarbonyl, aminosulfonyl, $(C_1$-$C_4)$-alkylaminosulfonyl and di$((C_1$-$C_4)$-alkyl)aminosulfonyl, in another embodiment from halogen, $(C_1$-$C_4)$-alkyl, $(C_3$-$C_7)$-cycloalkyl, hydroxy, $(C_1$-$C_4)$-alkyloxy, oxo, $(C_1$-$C_4)$-alkyl-$S(O)_m$—, amino, $(C_1$-$C_4)$-alkylamino, di$((C_1$-$C_4)$-alkyl)amino, cyano, aminosulfonyl, $(C_1$-$C_4)$-alkylaminosulfonyl and di$((C_1$-$C_4)$-alkyl)aminosulfonyl, in another embodiment from halogen, $(C_1$-$C_4)$-alkyl, $(C_3$-$C_7)$-cycloalkyl, hydroxy, $(C_1$-$C_4)$-alkyloxy, oxo, $(C_1$-$C_4)$-alkyl-$S(O)_m$—, amino, $(C_1$-$C_4)$-alkylamino, di$((C_1$-$C_4)$-alkyl)amino, cyano and aminosulfonyl, in another embodiment from halogen, $(C_1$-$C_4)$-alkyl, $(C_3$-$C_7)$-cycloalkyl, hydroxy, $(C_1$-$C_4)$-alkyloxy, oxo, amino, $(C_1$-$C_4)$-alkylamino, di$((C_1$-$C_4)$-alkyl)amino, cyano and aminosulfonyl, in another embodiment from halogen, $(C_1$-$C_4)$-alkyl, $(C_3$-$C_7)$-cycloalkyl, hydroxy, $(C_1$-$C_4)$-alkyloxy, amino, $(C_1$-$C_4)$-alkylamino, di$((C_1$-$C_4)$-alkyl)amino, cyano and aminosulfonyl, in another embodiment from halogen, $(C_1$-$C_4)$-alkyl, $(C_3$-$C_7)$-cycloalkyl, hydroxy, $(C_1$-$C_4)$-alkyloxy, amino, $(C_1$-$C_4)$-alkylamino and di$((C_1$-$C_4)$-alkyl)amino, in another embodiment from halogen, $(C_1$-$C_4)$-alkyl, $(C_3$-$C_7)$-cycloalkyl, $(C_1$-$C_4)$-alkyloxy and di$((C_1$-$C_4)$-alkyl)amino, in another embodiment from halogen, $(C_1$-$C_4)$-alkyl, $(C_3$-$C_7)$-cycloalkyl, hydroxy and $(C_1$-$C_4)$-alkyloxy, in another embodiment from halogen, $(C_1$-$C_4)$-alkyl and $(C_1$-$C_4)$-alkyloxy, in another embodiment from fluorine, chlorine, $(C_1$-$C_4)$-alkyl, $(C_3$-$C_7)$-cycloalkyl, hydroxy and $(C_1$-$C_4)$-alkyloxy, wherein in all these embodiments all alkyl groups independently of each other are optionally substituted by one or more fluorine substituents.

In one embodiment, the optional substituents $R^{31}$ on the residue of an aromatic ring representing $R^3$, for example on a phenyl group or pyridinyl group representing $R^3$, are chosen from halogen, $(C_1$-$C_4)$-alkyl, $(C_3$-$C_7)$-cycloalkyl, hydroxy, $(C_1$-$C_4)$-alkyloxy, $(C_1$-$C_4)$-alkyl-$S(O)_m$—, amino, $(C_1$-$C_4)$-alkylamino, di$((C_1$-$C_4)$-alkyl)amino, $(C_1$-$C_4)$-alkylcarbonylamino, $(C_1$-$C_4)$-alkylsulfonylamino, cyano, $(C_1$-$C_4)$-alkylcarbonyl, aminosulfonyl, $(C_1$-$C_4)$-alkylaminosulfonyl and di$((C_1$-$C_4)$-alkyl)aminosulfonyl, in another embodiment from halogen, $(C_1$-$C_4)$-alkyl, $(C_3$-$C_7)$-cycloalkyl, hydroxy, $(C_1$-$C_4)$-alkyloxy, $(C_1$-$C_4)$-alkyl-$S(O)_m$—, amino, $(C_1$-$C_4)$-alkylamino, di$((C_1$-$C_4)$-alkyl)amino, cyano, aminosulfonyl, $(C_1$-$C_4)$-alkylaminosulfonyl and di$((C_1$-$C_4)$-alkyl)aminosulfonyl, in another embodiment from halogen, $(C_1$-$C_4)$-alkyl, $(C_3$-$C_7)$-cycloalkyl, hydroxy, $(C_1$-$C_4)$-alkyloxy, $(C_1$-$C_4)$-alkyl-$S(O)_m$—, amino, $(C_1$-$C_4)$-alkylamino, di$((C_1$-$C_4)$-alkyl)amino, cyano and aminosulfonyl, in another embodiment from halogen, $(C_1$-$C_4)$-alkyl, $(C_3$-$C_7)$-cycloalkyl, hydroxy, $(C_1$-$C_4)$-alkyloxy, amino, $(C_1$-$C_4)$-alkylamino, di$((C_1$-$C_4)$-alkyl)amino, cyano and aminosulfonyl, in another embodiment from halogen, $(C_1$-$C_4)$-alkyl, $(C_3$-$C_7)$-cycloalkyl, hydroxy, $(C_1$-$C_4)$-alkyloxy, amino, $(C_1$-$C_4)$-alkylamino and di$((C_1$-$C_4)$-alkyl)amino, in another embodiment from halogen, $(C_1$-$C_4)$-alkyl, $(C_3$-$C_7)$-cycloalkyl, $(C_1$-$C_4)$-alkyloxy and di$((C_1$-$C_4)$-alkyl)amino, in another embodiment from halogen, $(C_1$-$C_4)$-alkyl, $(C_3$-$C_7)$-cycloalkyl, hydroxy and $(C_1$-$C_4)$-alkyloxy, in another embodiment from halogen, $(C_1$-$C_4)$-alkyl and $(C_1$-$C_4)$-alkyloxy, in another embodiment from fluorine, chlorine, $(C_1$-$C_4)$-alkyl, $(C_3$-$C_7)$-cycloalkyl, hydroxy and $(C_1$-$C_4)$-alkyloxy, wherein in all these embodiments all alkyl groups independently of each other are optionally substituted by one or more fluorine substituents.

In one embodiment, the optional substituents $R^{31}$ on the residue of a saturated or non-aromatic unsaturated ring representing $R^3$ are chosen from halogen, $(C_1$-$C_4)$-alkyl, $(C_3$-$C_7)$-cycloalkyl, hydroxy, $(C_1$-$C_4)$-alkyloxy, oxo, $(C_1$-$C_4)$-alkyl-$S(O)_m$—, amino, $(C_1$-$C_4)$-alkylamino, di$((C_1$-$C_4)$-alkyl)amino, $(C_1$-$C_4)$-alkylcarbonylamino, $(C_1$-$C_4)$-alkylsulfonylamino and cyano, in another embodiment from halogen, $(C_1$-$C_4)$-alkyl, $(C_3$-$C_7)$-cycloalkyl, hydroxy, $(C_1$-$C_4)$-alkyloxy, oxo, amino, $(C_1$-$C_4)$-alkylamino, di$((C_1$-$C_4)$-alkyl)amino and cyano, in another embodiment from halogen, $(C_1$-$C_4)$-alkyl, $(C_3$-$C_7)$-cycloalkyl, hydroxy, $(C_1$-$C_4)$-alkyloxy and oxo, in another embodiment from halogen, $(C_1$-$C_4)$-alkyl, hydroxy, $(C_1$-$C_4)$-alkyloxy and oxo, in another embodiment from fluorine, chlorine, $(C_1$-$C_4)$-alkyl, hydroxy, $(C_1$-$C_4)$-alkyloxy and oxo, in another embodiment from $(C_1$-$C_4)$-alkyl, hydroxy and oxo, in another embodiment from alkyl and hydroxy, and in another embodiment they are $(C_1$-$C_4)$-alkyl, wherein in all these embodiments all alkyl groups independently of each other are optionally substituted by one or more fluorine substituents. If the residue of a ring representing $R^3$ contains any oxo groups as substituents $R^{31}$, in one embodiment not more than two such oxo substituents are present, and in another embodiment not more than one such oxo substituent is present.

In one embodiment of the invention, the ring heteroatoms in Het are chosen from N and O, in another embodiment from O and S, in another embodiment they are O atoms. In another embodiment, the number of ring heteroatoms in Het is 1. In one embodiment, two ring oxygen atoms in Het are not present in adjacent ring positions, in another embodiment two ring heteroatoms chosen from O and S are not present in adjacent ring positions, in another embodiment two ring heteroatoms are not present in adjacent ring positions. Ring nitrogen atoms in Het carry a hydrogen atom or a substituent as specified. In one embodiment, optional substituents on ring nitrogen atoms in Het are $(C_1$-$C_4)$-alkyl substituents. In one embodiment, optional substituents on ring nitrogen atoms and ring carbon atoms in Het are $(C_1$-$C_4)$-alkyl substituents. In one embodiment, the number of optional substituents on Het is 1, 2, 3, 4 or 5, in another embodiment 1, 2, 3 or 4, in another embodiment 1, 2 or 3, in another embodiment 1 or 2, in another embodiment 1. Het can be bonded via any suitable ring carbon atom. In one embodiment, Het is bonded via a ring carbon atom which is not adjacent to a ring heteroatom. Het can be 4-membered, 5-membered, 6-membered or 7-membered. In one embodiment, Het is 4-membered or 5-membered, in another embodiment 5-membered to 7-membered, in another embodiment 5-membered or 6-membered, in another embodiment 4-membered. Examples of Het, from which Het is chosen in one embodiment, are oxetanyl including oxetan-2-yl and oxetan-3-yl, tetrahydrofuranyl including tetrahydrofuran-2-yl and tetrahydrofuran-3-yl, tetrahydropyranyl including tetrahydropyran-2-yl, tetrahydropyran-3-yl and tetrahydropyran-4-yl, oxepanyl including oxepan-2-yl, oxepan-3-yl and oxepan-4-yl, [1,3]dioxolanyl including [1,3]dioxolan-2-yl and [1,3]dioxolan-4-yl, [1,4]dioxanyl including [1,4]dioxan-2-yl, thietanyl including thietan-2-yl and thietan-3-yl, tetrahydrothiophenyl including tetrahydrothiophen-2-yl and tetrahydrothiophen-3-yl, tetrahydrothiopyranyl including tetrahydrothiopyran-2-yl, tetrahydrothiopyran-3-yl and tetrahydrothiopyran-4-yl, [1,4]dithianyl including [1,4]dithian-2-yl, azetidinyl including azetidin-2-yl and azetidin-3-yl, pyrrolidinyl including pyrrolidinyl-2-yl and pyrrolidinyl-3-yl, piperidinyl including piperidinyl-2-yl, piperidinyl-3-yl and piperidinyl-4-yl, azepanyl including azepan-2-yl, azepan-3-yl and azepan-4-yl, oxazolidinyl including oxazolidin-2-yl, oxazolidin-4-yl and oxazolidin-5-yl, thiazolidinyl including thiazolidin-2-yl, thiazolidin-4-yl and thiazolidin-5-yl, morpholinyl including morpholin-2-yl and morpholin-3-yl, thiomorpholinyl including thiomorpholin-2-yl and thiomorpholin-3-yl, which all are optionally substituted as specified with respect to Het.

A subject of the invention are all compounds of the formula I wherein one or more structural elements such as groups, substituents and numbers are defined as in any of the specified embodiments or definitions of the elements or have one or more of the specific meanings which are mentioned herein as examples of elements, wherein all combinations of one or more specified embodiments and/or definitions and/or specific meanings of the elements are a subject of the present invention. Also with respect to all such compounds of the formula I, all their stereoisomeric forms and mixtures of stereoisomeric forms in any ratio, and their physiologically acceptable salts, and the physiologically acceptable solvates of any of them, are a subject of the present invention.

An example of compounds of the invention which with respect to any structural elements are defined as in the specified embodiments of the invention or definitions of such elements, and which are a subject of the invention, are compounds of the formula I, wherein $R^3$ is chosen from $(C_1-C_6)$-alkyl, $(C_3-C_7)$-cycloalkyl-$C_uH_{2u}$— and Het-$C_vH_{2v}$—, wherein u and v are chosen from 1 and 2, or $R^3$ is a residue of a saturated or unsaturated, 3-membered to 10-membered, monocyclic or bicyclic ring which comprises 0, 1 or 2 identical or different ring heteroatoms chosen from N, O and S, wherein one or two of the ring nitrogen atoms can carry a hydrogen atom or a $(C_1-C_4)$-alkyl substituent and one of the ring sulfur atoms can carry one or two oxo groups, and wherein the residue of a ring is optionally substituted on one or more ring carbon atoms by identical or different substituents $R^{31}$, provided that $R^3$ cannot be $(C_1-C_6)$-alkyl if A is S;

Het is a residue of a saturated, 4-membered to 6-membered, monocyclic heterocycle which comprises 1 ring heteroatom chosen from N, O and S and which is bonded via a ring carbon atom, wherein the residue of a heterocycle is optionally substituted by one or more identical or different substituents chosen from fluorine and $(C_1-C_4)$-alkyl; and all other groups and numbers are defined as in the general definition of the compounds of the formula I or in any specified embodiments of the invention or definitions of structural elements.

Another such example are compounds of the formula I, in any of their stereoisomeric forms, or a mixture of stereoisomeric forms in any ratio, and the physiologically acceptable salts thereof, and the physiologically acceptable solvates of any of them,
wherein
A is chosen from O and S;
X is chosen from $(C_1-C_6)$-alkanediyl, $(C_2-C_6)$-alkanediyl and $(C_1-C_6)$-alkanediyl-oxy;
$R^1$ is chosen from $(C_1-C_6)$-alkyl, $(C_3-C_7)$-cycloalkyl-$C_tH_{2t}$— and Het-$C_tH_{2t}$—, wherein t is chosen from 0, 1 and 2;
$R^2$ is chosen from phenylene and pyridinediyl, wherein the phenylene and the pyridinediyl are optionally substituted on one or more ring nitrogen atoms by identical or different substituents $R^{22}$;
$R^3$ is chosen from $(C_1-C_6)$-alkyl, $(C_3-C_7)$-cycloalkyl-$C_uH_{2u}$— and Het-$C_vH_{2v}$—, wherein u and v are chosen from 1 and 2, or $R^3$ is a residue of a saturated or unsaturated, 3-membered to 10-membered, monocyclic or bicyclic ring which comprises 0, 1 or 2 identical or different ring heteroatoms chosen from N, O and S, wherein one or two of the ring nitrogen atoms can carry a hydrogen atom or a $(C_1-C_4)$-alkyl substituent and one of the ring sulfur atoms can carry one or two oxo groups, and wherein the residue of a ring is optionally substituted on one or more ring carbon atoms by identical or different substituents $R^{31}$, provided that $R^3$ cannot be $(C_1-C_6)$-alkyl if A is S;

Het is a residue of a saturated, 4-membered to 6-membered, monocyclic heterocycle which comprises 1 ring heteroatom chosen from N, O and S and which is bonded via a ring carbon atom, wherein the residue of a heterocycle is optionally substituted by one or more identical or different substituents chosen from fluorine and $(C_1-C_4)$-alkyl; and all other groups and numbers are defined as in the general definition of the compounds of the formula I or in any specified embodiments of the invention or definitions of structural elements.

Another such example are compounds of the formula I, in any of their stereoisomeric forms, or a mixture of stereoisomeric forms in any ratio, and the physiologically acceptable salts thereof, and the physiologically acceptable solvates of any of them,
wherein
A is O;
X is chosen from $(C_1-C_6)$-alkanediyl and $(C_1-C_6)$-alkanediyl-oxy;
$R^1$ is chosen from $(C_1-C_6)$-alkyl and $(C_3-C_6)$-cycloalkyl-$C_tH_{2t}$—, wherein t is chosen from 0 and 1;
$R^2$ is phenylene which is optionally substituted on one or more ring carbon atoms by identical or different substituents $R^{22}$;
$R^3$ is chosen from $(C_1-C_6)$-alkyl, $(C_3-C_7)$-cycloalkyl-$C_uH_{2u}$— and Het-$C_vH_{2v}$—, wherein u and v are chosen from 1 and 2, or $R^3$ is a residue of a saturated or unsaturated, 3-membered to 7-membered, monocyclic or bicyclic ring which comprises 0, 1 or 2 identical or different ring heteroatoms chosen from N, O and S, wherein one or two of the ring nitrogen atoms can carry a hydrogen atom or a $(C_1-C_4)$-alkyl substituent and one of the ring sulfur atoms can carry one or two oxo groups, and wherein the residue of a ring is optionally substituted on one or more ring carbon atoms by identical or different substituents $R^{31}$, provided that $R^3$ cannot be $(C_1$-$C_6)$-alkyl if A is S;

$R^4$ is chosen from hydrogen and $(C_1$-$C_4)$-alkyl;

$R^{22}$ is chosen from halogen, hydroxy, $(C_1$-$C_4)$-alkyl- and $(C_1$-$C_4)$-alkyloxy;

$R^{31}$ is chosen from halogen, $(C_1$-$C_4)$-alkyl, $(C_3$-$C_7)$-cycloalkyl, hydroxy and $(C_1$-$C_4)$-alkyloxy;

Het is a residue of a saturated, 4-membered to 6-membered, monocyclic heterocycle which comprises 1 ring heteroatom chosen from O and S and which is bonded via a ring carbon atom, wherein the residue of a heterocycle is optionally substituted by one or more identical or different substituents chosen from fluorine and $(C_1$-$C_4)$-alkyl; wherein all cycloalkyl groups, independently of each other and independently of any other substituents, are optionally substituted by one or more identical or different substituents chosen from fluorine and $(C_1$-$C_4)$-alkyl;

wherein all alkyl, alkanediyl, $C_tH_{2t}$, $C_uH_{2u}$ and $C_vH_{2v}$ groups, independently of each other and independently of any other substituents, are optionally substituted by one or more fluorine substituents.

Likewise, also with respect to all specific compounds disclosed herein, such as the example compounds which represent embodiments of the invention wherein the various groups and numbers in the general definition of the compounds of the formula I have the specific meanings present in the respective specific compound, it applies that they are a subject of the present invention in any of their stereoisomeric forms and or a mixture of stereoisomeric forms in any ratio, and in the form of their physiologically acceptable salts, and in the form of the physiologically acceptable solvates of any of them. Irrespective of whether a specific compound is disclosed herein as a free compound and/or as a specific salt, it is a subject of the invention both in the form of the free compound and in the form of all its physiologically acceptable salts, and if a specific salt is disclosed, additionally in the form of this specific salt, and in the form of the physiologically acceptable solvates of any of them. Thus, a subject of the invention also is a compound of the formula I which is chosen from one or more of the specific compounds of the formula I disclosed herein, including the example compounds specified below, and the physiologically acceptable salts thereof, and the physiologically acceptable solvates of any of them, wherein the compound of the formula I is a subject of the invention in any of its stereoisomeric forms or as a mixture of stereoisomeric forms in any ratio, insofar as applicable. As an example is mentioned a compound of the formula I, or a physiologically acceptable solvate of any of them, which is chosen from {4-[5-(2,5-difluoro-phenoxy)-7-propoxy-oxazolo[5,4-d]pyrimidin-2-yl]-2,6-dimethyl-phenoxy}-acetic acid,

[4-(5-cyclopentyloxy-7-propoxy-oxazolo[5,4-d]pyrimidin-2-yl)-2,6-dimethyl-phenoxy]-acetic acid, {4-[5-(trans-2-fluoro-cyclohexyloxy)-7-propoxy-oxazolo[5,4-d]pyrimidin-2-yl]-2,6-dimethyl-phenoxy}-acetic acid, {4-[5-(2-fluoro-phenoxy)-7-propoxy-oxazolo[5,4-d]pyrimidin-2-yl]-2,6-dimethyl-phenoxy}-acetic acid, {4-[5-(5-fluoro-2-methyl-phenoxy)-7-propoxy-oxazolo[5,4-d]pyrimidin-2-yl]-2,6-dimethyl-phenoxy}-acetic acid, {4-[5-(3-fluoro-4-methyl-phenoxy)-7-propoxy-oxazolo[5,4-d]pyrimidin-2-yl]-2,6-dimethyl-phenoxy}-acetic acid, {2,6-dimethyl-4-[7-propoxy-5-(pyridin-3-yloxy)-oxazolo[5,4-d]pyrimidin-2-yl]-phenoxy}-acetic acid, {4-[5-(2,4-difluoro-phenoxy)-7-propoxy-oxazolo[5,4-d]pyrimidin-2-yl]-2,6-dimethyl-phenoxy}-acetic acid,

[2,6-dimethyl-4-(5-phenoxy-7-propoxy-oxazolo[5,4-d]pyrimidin-2-yl)-phenoxy]-acetic acid, {4-[5-(3-chloro-phenoxy)-7-propoxy-oxazolo[5,4-d]pyrimidin-2-yl]-2,6-dimethyl-phenoxy}-acetic acid,

[4-(5-cyclohexylmethoxy-7-propoxy-oxazolo[5,4-d]pyrimidin-2-yl)-2,6-dimethyl-phenoxy]-acetic acid,

[4-(5-isobutoxy-7-propoxy-oxazolo[5,4-d]pyrimidin-2-yl)-2,6-dimethyl-phenoxy]-acetic acid,

[4-(5-cyclobutylmethoxy-7-propoxy-oxazolo[5,4-d]pyrimidin-2-yl)-2,6-dimethyl-phenoxy]-acetic acid,

[4-(5-cyclobutoxy-7-propoxy-oxazolo[5,4-d]pyrimidin-2-yl)-2,6-dimethyl-phenoxy]-acetic acid,

[4-(5,7-dipropoxy-oxazolo[5,4-d]pyrimidin-2-yl)-2,6-dimethyl-phenoxy]-acetic acid, {2,6-dimethyl-4-[7-propoxy-5-(3,3,3-trifluoro-propoxy)-oxazolo[5,4-d]pyrimidin-2-yl]-phenoxy}-acetic acid,

[4-(5-ethoxy-7-propoxy-oxazolo[5,4-d]pyrimidin-2-yl)-2,6-dimethyl-phenoxy]-acetic acid,

[4-(5-cyclopentylmethoxy-7-propoxy-oxazolo[5,4-d]pyrimidin-2-yl)-2,6-dimethyl-phenoxy]-acetic acid, {2,6-dimethyl-4-[7-propoxy-5-(tetrahydrofuran-2-yl-methoxy)-oxazolo[5,4-d]pyrimidin-2-yl]-phenoxy}-acetic acid,

[4-(5-sec-butoxy-7-propoxy-oxazolo[5,4-d]pyrimidin-2-yl)-2,6-dimethyl-phenoxy]-acetic acid, {2,6-dimethyl-4-[7-propoxy-5-(3,3,3-trifluoro-1-methyl-propoxy)-oxazolo[5,4-d]pyrimidin-2-yl]-phenoxy}-acetic acid, {2,6-dimethyl-4-[5-(3-methyl-butoxy)-7-propoxy-oxazolo[5,4-d]pyrimidin-2-yl]-phenoxy}-acetic acid, {4-[5-(2-cyclopropyl-ethoxy)-7-propoxy-oxazolo[5,4-d]pyrimidin-2-yl]-2,6-dimethyl-phenoxy}-acetic acid, {2,6-dimethyl-4-[7-propoxy-5-(2,2,2-trifluoro-1-methyl-ethoxy)-oxazolo[5,4-d]pyrimidin-2-yl]-phenoxy}-acetic acid, {4-[5-(3-fluoro-phenoxy)-7-propoxy-oxazolo[5,4-d]pyrimidin-2-yl]-2,6-dimethyl-phenoxy}-acetic acid, {2,6-dimethyl-4-[7-propoxy-5-(3-trifluoromethyl-phenoxy)-oxazolo[5,4-d]pyrimidin-2-yl]-phenoxy}-acetic acid,

[2,6-dimethyl-4-(7-propoxy-5-{3-methylphenoxy}-oxazolo[5,4-d]pyrimidin-2-yl)-phenoxy]-acetic acid, {4-[5-(3-ethyl-phenoxy)-7-propoxy-oxazolo[5,4-d]pyrimidin-2-yl]-2,6-dimethyl-phenoxy}-acetic acid, {4-[5-(3-chloro-4-fluoro-phenoxy)-7-propoxy-oxazolo[5,4-d]pyrimidin-2-yl]-2,6-dimethyl-phenoxy}-acetic acid, {4-[5-(3-chloro-4-methyl-phenoxy)-7-propoxy-oxazolo[5,4-d]pyrimidin-2-yl]-2,6-dimethyl-phenoxy}-acetic acid, {4-[5-(5-chloro-2-methyl-phenoxy)-7-propoxy-oxazolo[5,4-d]pyrimidin-2-yl]-2,6-dimethyl-phenoxy}-acetic acid, {4-[5-(3-chloro-2-methyl-phenoxy)-7-propoxy-oxazolo[5,4-d]pyrimidin-2-yl]-2,6-dimethyl-phenoxy}-acetic acid, {4-[5-(3-chloro-2-fluoro-phenoxy)-7-propoxy-oxazolo[5,4-d]pyrimidin-2-yl]-2,6-dimethyl-phenoxy}-acetic acid, {4-[5-(5-chloro-2-fluoro-phenoxy)-7-propoxy-oxazolo[5,4-d]pyrimidin-2-yl]-2,6-dimethyl-phenoxy}-acetic acid, {4-[5-(3,4-difluoro-phenoxy)-7-propoxy-oxazolo[5,4-d]pyrimidin-2-yl]-2,6-dimethyl-phenoxy}-acetic acid, {4-[5-(4-fluoro-3-methyl-phenoxy)-7-propoxy-oxazolo[5,4-d]pyrimidin-2-yl]-2,6-dimethyl-phenoxy}-acetic acid, {4-[5-(2,3-difluoro-phenoxy)-7-propoxy-oxazolo[5,4-d]pyrimidin-2-yl]-2,6-dimethyl-phenoxy}-acetic acid, {4-[5-(3,5-difluoro-phenoxy)-7-propoxy-oxazolo[5,4-d]pyrimidin-2-yl]-2,6-dimethyl-phenoxy}-acetic acid, {4-[5-(3-chloro-5-fluoro-phenoxy)-7-propoxy-oxazolo[5,4-d]pyrimidin-2-yl]-2,6-dimethyl-phenoxy}-acetic acid, {4-[5-(3-fluoro-5-trifluoromethyl-phenoxy)-7-propoxy-oxazolo[5,4-d]pyrimidin-2-yl]-2,6-dimethyl-phenoxy}-acetic acid,
{4-[5-(3-fluoro-5-methyl-phenoxy)-7-propoxy-oxazolo[5,4-d]pyrimidin-2-yl]-2,6-dimethyl-phenoxy}-acetic acid,
{4-[5-(4-fluoro-phenoxy)-7-propoxy-oxazolo[5,4-d]pyrimidin-2-yl]-2,6-dimethyl-phenoxy}-acetic acid,
{4-[5-(2-fluoro-5-methyl-phenoxy)-7-propoxy-oxazolo[5,4-d]pyrimidin-2-yl]-2,6-dimethyl-phenoxy}-acetic acid,
{4-[5-(2-chloro-5-fluoro-phenoxy)-7-propoxy-oxazolo[5,4-d]pyrimidin-2-yl]-2,6-dimethyl-phenoxy}-acetic acid,
{4-[5-(4-chloro-3-fluoro-phenoxy)-7-propoxy-oxazolo[5,4-d]pyrimidin-2-yl]-2,6-dimethyl-phenoxy}-acetic acid,
[2,6-dimethyl-4-(7-propoxy-5-{4-methylphenoxy}-oxazolo[5,4-d]pyrimidin-2-yl)-phenoxy]-acetic acid,
[2,6-dimethyl-4-(7-propoxy-5-{2-methylphenoxy}-oxazolo[5,4-d]pyrimidin-2-yl)-phenoxy]-acetic acid,
{4-[5-(2-chloro-phenoxy)-7-propoxy-oxazolo[5,4-d]pyrimidin-2-yl]-2,6-dimethyl-phenoxy}-acetic acid,
{4-[5-(2-chloro-3-trifluoromethyl-phenoxy)-7-propoxy-oxazolo[5,4-d]pyrimidin-2-yl]-2,6-dimethyl-phenoxy}-acetic acid,
{4-[5-(2-chloro-5-trifluoromethyl-phenoxy)-7-propoxy-oxazolo[5,4-d]pyrimidin-2-yl]-2,6-dimethyl-phenoxy}-acetic acid,
{4-[5-(4-chloro-3-trifluoromethyl-phenoxy)-7-propoxy-oxazolo[5,4-d]pyrimidin-2-yl]-2,6-dimethyl-phenoxy}-acetic acid,
{4-[5-(4-fluoro-3-trifluoromethyl-phenoxy)-7-propoxy-oxazolo[5,4-d]pyrimidin-2-yl]-2,6-dimethyl-phenoxy}-acetic acid,
{4-[5-(2-fluoro-5-trifluoromethyl-phenoxy)-7-propoxy-oxazolo[5,4-d]pyrimidin-2-yl]-2,6-dimethyl-phenoxy}-acetic acid,
{4-[5-(2-fluoro-3-trifluoromethyl-phenoxy)-7-propoxy-oxazolo[5,4-d]pyrimidin-2-yl]-2,6-dimethyl-phenoxy}-acetic acid,
{2,6-dimethyl-4-[7-propoxy-5-(2-trifluoromethyl-phenoxy)-oxazolo[5,4-d]pyrimidin-2-yl]-phenoxy}-acetic acid,
{2,6-dimethyl-4-[7-propoxy-5-(4-trifluoromethyl-phenoxy)-oxazolo[5,4-d]pyrimidin-2-yl]-phenoxy}-acetic acid,
{4-[5-(4-chloro-2-fluoro-phenoxy)-7-propoxy-oxazolo[5,4-d]pyrimidin-2-yl]-2,6-dimethyl-phenoxy}-acetic acid,
{4-[5-(2-chloro-4-fluoro-phenoxy)-7-propoxy-oxazolo[5,4-d]pyrimidin-2-yl]-2,6-dimethyl-phenoxy}-acetic acid,
{4-[5-(3-methoxy-phenoxy)-7-propoxy-oxazolo[5,4-d]pyrimidin-2-yl]-2,6-dimethyl-phenoxy}-acetic acid,
{2,6-dimethyl-4-[7-propoxy-5-(3-trifluoromethoxy-phenoxy)-oxazolo[5,4-d]pyrimidin-2-yl]-phenoxy}-acetic acid,
{2,6-dimethyl-4-[7-propoxy-5-(3-trifluoromethylsulfanyl-phenoxy)-oxazolo[5,4-d]pyrimidin-2-yl]-phenoxy}-acetic acid,
{4-[5-(indan-5-yloxy)-7-propoxy-oxazolo[5,4-d]pyrimidin-2-yl]-2,6-dimethyl-phenoxy}-acetic acid,
{4-[5-(indan-4-yloxy)-7-propoxy-oxazolo[5,4-d]pyrimidin-2-yl]-2,6-dimethyl-phenoxy}-acetic acid,
{2,6-dimethyl-4-[5-(naphthalen-2-yloxy)-7-propoxy-oxazolo[5,4-d]pyrimidin-2-yl]-phenoxy}-acetic acid,
{2,6-dimethyl-4-[5-(2-methyl-benzothiazol-5-yloxy)-7-propoxy-oxazolo[5,4-d]pyrimidin-2-yl]-phenoxy}-acetic acid,
{4-[5-(benzothiazol-6-yloxy)-7-propoxy-oxazolo[5,4-d]pyrimidin-2-yl]-2,6-dimethyl-phenoxy}-acetic acid,
{2,6-dimethyl-4-[5-(6-methyl-pyridin-3-yloxy)-7-propoxy-oxazolo[5,4-d]pyrimidin-2-yl]-phenoxy}-acetic acid,
{2,6-dimethyl-4-[5-(2-methyl-pyridin-3-yloxy)-7-propoxy-oxazolo[5,4-d]pyrimidin-2-yl]-phenoxy}-acetic acid,
{2,6-dimethyl-4-[5-(5-methyl-pyridin-3-yloxy)-7-propoxy-oxazolo[5,4-d]pyrimidin-2-yl]-phenoxy}-acetic acid,
{4-[5-(5-chloro-pyridin-3-yloxy)-7-propoxy-oxazolo[5,4-d]pyrimidin-2-yl]-2,6-dimethyl-phenoxy}-acetic acid,
{4-[5-(5-fluoro-pyridin-3-yloxy)-7-propoxy-oxazolo[5,4-d]pyrimidin-2-yl]-2,6-dimethyl-phenoxy}-acetic acid,
{2,6-dimethyl-4-[7-propoxy-5-([1,2,5]thiadiazol-3-yloxy)-oxazolo[5,4-d]pyrimidin-2-yl]-phenoxy}-acetic acid,
{4-[5-(isothiazol-3-yloxy)-7-propoxy-oxazolo[5,4-d]pyrimidin-2-yl]-2,6-dimethyl-phenoxy}-acetic acid,
{2,6-dimethyl-4-[7-propoxy-5-(5-trifluoromethyl-thiophen-3-yloxy)-oxazolo[5,4-d]pyrimidin-2-yl]-phenoxy}-acetic acid,
{2,6-dimethyl-4-[7-propoxy-5-(thiazol-2-ylsulfanyl)-oxazolo[5,4-d]pyrimidin-2-yl]-phenoxy}-acetic acid,
{2,6-dimethyl-4-[5-(4-methyl-thiazol-2-ylsulfanyl)-7-propoxy-oxazolo[5,4-d]pyrimidin-2-yl]-phenoxy}-acetic acid,
{4-[5-(1,1-dioxo-tetrahydro-thiophen-3-ylsulfanyl)-7-propoxy-oxazolo[5,4-d]pyrimidin-2-yl]-2,6-dimethyl-phenoxy}-acetic acid,
{4-[5-(2,5-dimethyl-furan-3-ylsulfanyl)-7-propoxy-oxazolo[5,4-d]pyrimidin-2-yl]-2,6-dimethyl-phenoxy}-acetic acid, wherein a compound such as {4-[5-(trans-2-fluoro-cyclohexyloxy)-7-propoxy-oxazolo[5,4-d]pyrimidin-2-yl]-2,6-dimethyl-phenoxy}-acetic acid, {2,6-dimethyl-4-[7-propoxy-5-(tetrahydrofuran-2-ylmethoxy)-oxazolo[5,4-d]pyrimidin-2-yl]-phenoxy}-acetic acid, [4-(5-sec-butoxy-7-propoxy-oxazolo[5,4-d]pyrimidin-2-yl)-2,6-dimethyl-phenoxy]-acetic acid, {2,6-dimethyl-4-[7-propoxy-5-(3,3,3-trifluoro-1-methyl-propoxy)-oxazolo[5,4-d]pyrimidin-2-yl]-phenoxy}-acetic acid or {2,6-dimethyl-4-[7-propoxy-5-(2,2,2-trifluoro-1-methyl-ethoxy)-oxazolo[5,4-d]pyrimidin-2-yl]-phenoxy}-acetic acid, which can be present in S configuration or R configuration, is a subject of the invention in S configuration or R configuration or a mixture of the enantiomeric forms in any ratio.

Another subject of the present invention are processes for the preparation of the compounds of the formula I and their salts and solvates, by which the compounds are obtainable and which are outlined in the following. In one process, a compound of the formula II is reacted with a compound of the formula III to give a compound of the formula I,

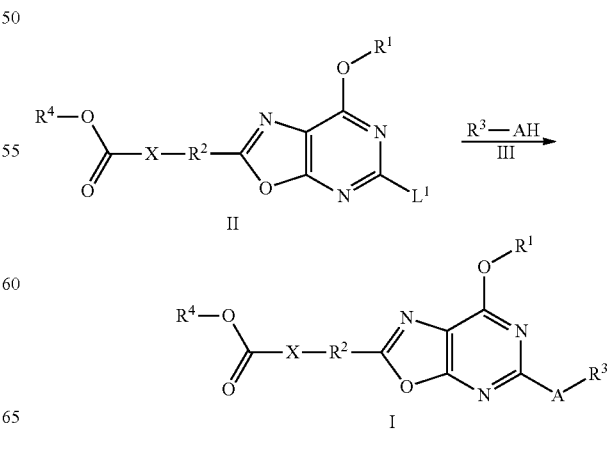

wherein the groups A, X, $R^1$, $R^2$, $R^3$ and $R^4$ in the compounds of the formulae II and III are defined as in the compounds of the formula I and additionally functional groups can be present in protected form or in the form of a precursor group which is later converted into the final group. The group $L^1$ in the compounds of the formula II is a leaving group which can be replaced in a nucleophilic aromatic substitution reaction, such as a halogen atom, for example chlorine or bromine, or a sulfoxide group or a sulfone group, for example a group of the formula —S(O)-Alk or —S(O)$_2$-Alk wherein Alk is a ($C_1$-$C_4$)-alkyl group, for example methyl or ethyl.

The reaction of the compounds of the formulae II and III is a nucleophilic aromatic substitution reaction at the carbon atom in the 5-position of the oxazolo[5,4-d]pyrimidine ring, i.e. in the pyrimidine moiety, and can be carried out under standard conditions for such reactions which are well known to a person skilled in the art.

Generally the reaction is carried out in an inert solvent, for example a hydrocarbon or chlorinated hydrocarbon such as benzene, toluene, xylene, chlorobenzene, dichloromethane, chloroform or dichloroethane, an ether such as tetrahydrofuran (THF), dioxane, dibutyl ether, diisopropyl ether or 1,2-dimethoxyethane (DME), a ketone such as acetone or butan-2-one, an ester such as ethyl acetate or butyl acetate, a nitrile such as acetonitrile, an amide such as N,N-dimethylformamide (DMF) or N-methylpyrrolidin-2-one (NMP), or a mixture of solvents, at temperatures from about 20° C. to about 160° C., for example at temperatures from about 40° C. to about 100° C., depending on the particulars of the specific case. Generally it is favorable for enhancing the nucleophilicity of the compound of the formula III to add a base, for example a tertiary amine, such as triethylamine, ethyldiisopropylamine or N-methylmorpholine, or an inorganic base such as an alkaline earth metal hydride, hydroxide, carbonate or hydrogencarbonate like sodium hydride, sodium hydroxide, potassium hydroxide, sodium carbonate, potassium carbonate, cesium carbonate or sodium hydrogencarbonate, or an alkoxide or amide such as sodium methoxide, sodium ethoxide, potassium methoxide, potassium tert-butoxide, sodium amide or lithium diisopropylamide. A compound of the formula III can also be treated with a base and converted into a salt separately before the reaction with the compound of the formula II.

The starting compounds of the formulae II and III can be obtained by procedures described in the literature or with reference to procedures described in the literature, and in many cases are commercially available. Compounds of the formula IIa, i.e. compounds of the formula II in which $L^1$ is a sulfoxide group of the formula Alk-S(O)— or a sulfone group of the formula Alk-S(O)$_2$—, for example, can be obtained by reacting an aminomalonic acid ester of the formula IV with an activated carboxylic acid derivative of the formula V to give a compound of the formula VI, reacting the latter compound with thiourea of the formula VII to give a compound of the formula VIII, alkylating the thiol with an alkylation reagent of the formula IX to give the thioether of the formula X, cyclizing the latter compound with formation of the oxazolo[5,4-d]pyrimidine ring system to give the compound of the formula XI, alkylating the latter compound at the oxygen atom of the keto group or the tautomeric hydroxy group, respectively, with an alkylation reagent of the formula XII, introducing the residue $R^4$O—C(O)—X— into the compound of the formula III by reaction of a compound of the formula XIV, and oxidizing the thioether moiety in the obtained compound of the formula XV to give the corresponding sulfoxide or sulfone of the formula IIa.

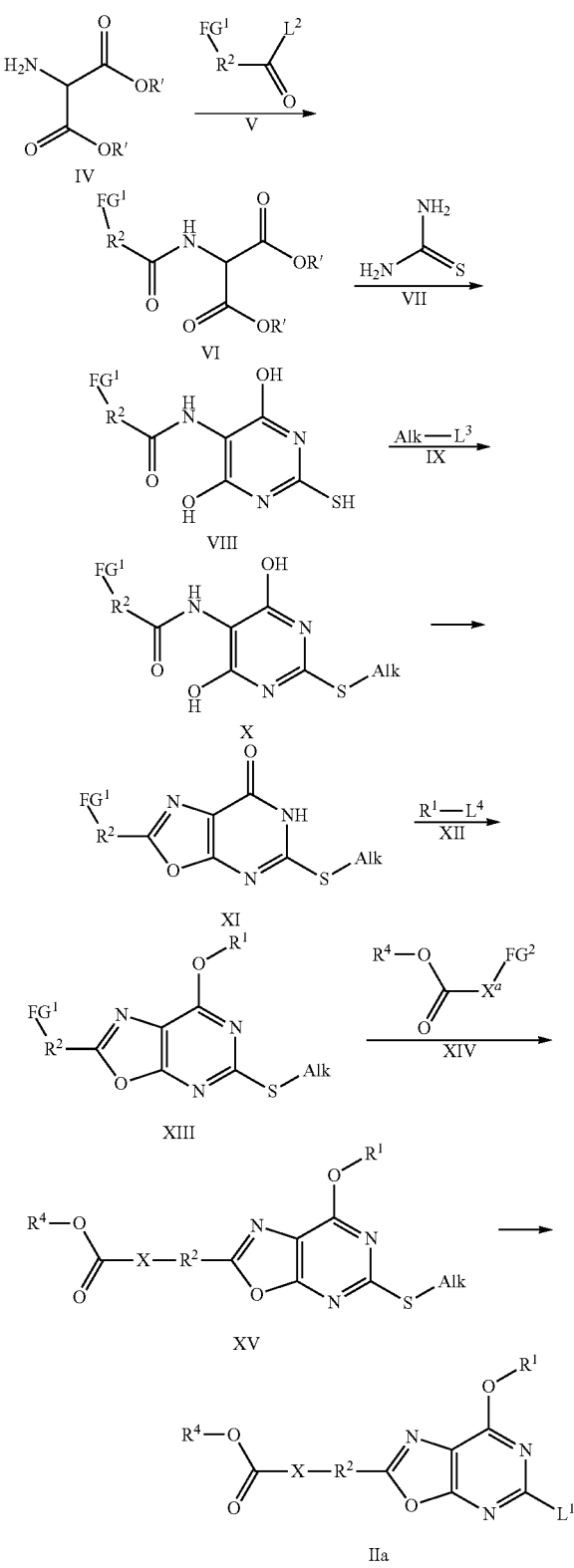

The groups X, $R^1$, $R^2$ and $R^4$ in the compounds of the formulae IIa, V, VI, VIII, X, XI, XII, XIII, XIV and XV are defined as in the compounds of the formula I and additionally functional groups can be present in protected form or in the form of a precursor group which is later converted into the final group. The group $X^a$ in the compounds of the formula XIV is defined as the group X in the compounds of the formula I, or comprises a part of the group X in the desired compound of the formula II, such that after the reaction of the compounds of the formulae XIII and XIV the group $X^a$ and any parts of the groups $FG^1$ and $FG^2$ remaining in the compound of the formula XV together form the desired group X. For example, in the case that the group X is an alkanediyl-oxy group, the group $X^a$ in the compound of the formula XIV can be the desired alkanediyl-oxy group and the group $FG^2$ can be a hydrogen atom attached to the oxygen atom, or the group $X^a$ can be the alkanediyl part, the group $FG^2$ is a leaving group, and the group $FG^1$ in the compound of the formula XIII is a hydroxy group, the oxygen atom of which together with the alkanediyl part then forms the desired alkanediyl-oxy group after alkylation of the compound of the formula XIII with the compound of the formula XIV.

The groups $FG^1$ and $FG^2$ in the compounds of the formulae V, VI, VIII, X, XI, XIII and XIV are functional groups suitable for the type of coupling used to form the desired group X from the group $X^a$ and any part of the groups $FG^1$ and $FG^2$ remaining in the compound of the formula XV. For example, if the group $X^a$ is attached to the group $R^2$ or to an atom in the group $FG^1$, such as an oxygen atom in a hydroxy group representing $FG^1$ as mentioned afore, via a nucleophilic substitution reaction, $FG^2$ can be a leaving group such as a halogen atom such as chlorine, bromine or iodine or a sulfonyloxy group like methanesulfonyloxy, trifluoromethanesulfonyloxy or toluenesulfonyloxy. If the group $X^a$ is attached to the group $R^2$ via a transition metal-catalyzed reaction, $FG^2$ can be a leaving group such as a boronic acid, boronic acid ester, dialkyl borane or stannane group, and in this case $FG^1$ can be halogen. $FG^2$ can also be a hydrogen atom or a carbon atom, part of a double bond in an alkenediyl group representing $X^a$ if a Heck reaction is used for attaching $X^a$ to $R^2$, and in this case $FG^1$ can be halogen. If a Wittig reaction or Wittig-Horner reaction is used for attaching $X^a$ to $R^2$, $FG^2$ can be a phosphonio group such as triphenylphosphonio or a phosphonyl group such as diethyl phosphonyl, and the compound of the formula XIV can be a phosphonium salt or a phosphonic acid ester, and in this case $FG^1$ can be an aldehyde group —C(O)—H or ketone group —C(O)-alkyl, and vice versa. Generally, the group $FG^1$ is present on the carbon atom in the phenylene group or heterocyclic group representing $R^2$ which in the compounds of the formulae XV, IIa and I carries the group X. The group $FG^1$ in the compounds of the formulae V, VI, VIII, X and XI can also be present in protected form or in the form of a precursor group which is later converted into the group which in the compound of the formula XIII reacts with the compound of the formula XIV. For example, a hydroxy group representing $FG^1$ in the compound of the formula XIII can be present in the compounds of the formulae V, VI, VIII, X and XI in protected form, for example in the form of an etherified hydroxy group such as a benzyl ether or an alkyl ether like a methyl ether. Such ethers can be cleaved by using methods well known to a person skilled in the art. A summary of methods for the removal of protecting groups can be found in the literature, for example in P. J. Kocienski, Protecting Groups (Thieme Verlag, 1994) or T. W. Greene and P. G. M. Wuts, Protective Groups in Organic Synthesis (John Wiley & Sons, 1999).

The group $L^1$ in the compounds of the formula IIa is defined as specified above. The group $L^2$ in the compounds of the formula V is a nucleophilically substitutable leaving group and can in particular be a halogen atom, such as chlorine or bromine, and the compound of the formula V can thus be a carboxylic acid halide. $L^2$ can also be a group of the formula $FG^1$-$R^2$—C(O)—O and the compound of the formula V can thus be a carboxylic acid anhydride, for example. The groups $L^3$ and $L^4$ are leaving groups which can be replaced in a nucleophilic substitution reaction, and can in particular be a halogen atom such as chlorine, bromine or iodine, or a sulfonyloxy group such as methanesulfonyloxy, trifluoromethanesulfonyloxy or toluenesulfonyloxy, i.e., the compounds of the formulae IX and XII can be organic halides or sulfonates, for example. The group R' in the compounds of the formulae IV and VI can be alkyl like $(C_1$-$C_3)$-alkyl, for example, such as methyl or ethyl. As mentioned, the compounds of the formula XI may also be present in another tautomeric form, for example in the form of the respective 7-hydroxy-oxazolo[5,4-d]pyrimidine derivatives in which the mobile hydrogen atom, which in formula XI is bonded to the ring nitrogen atom in the 6-position of the oxazolopyrimidine ring system, is bonded to the oxygen atom attached to the ring carbon atom in the 7-position. As far as applicable, it applies to all compounds occurring in the preparation of the compounds of the formula I that they can be present in any other tautomeric form than the one represented in their formulae. In the reactions of this process for the preparation of the compounds of the formula II, as in all other reactions carried out in the preparation of the compounds of the formula I, starting compounds can also be employed and/or products obtained in the form of a salt. For example, compounds of the formulae IV can be employed in the form of an acid addition salt such as the hydrochloride.

The reaction of the compounds of the formulae IV and V can be carried out under standard conditions for the acylation of an amine with an activated carboxylic acid derivative like an acid halide or acid anhydride. Generally the reaction is carried out in an inert solvent, for example a hydrocarbon or chlorinated hydrocarbon such as benzene, toluene, xylene, chlorobenzene, dichloromethane, chloroform or dichloroethane, an ether such as THF, dioxane, dibutyl ether, diisopropyl ether or DME, a ketone such as acetone or butan-2-one, an ester such as ethyl acetate or butyl acetate, or water, or a mixture of solvents, at temperatures from about −10° C. to about 40° C., for example at temperatures from about 0° C. to about 30° C. Generally the reaction is carried out with addition of a base, for example a tertiary amine, such as triethylamine, ethyldiisopropylamine or N-methylmorpholine, or an inorganic base such as an alkali metal hydroxide, carbonate or hydrogencarbonate like sodium hydroxide, potassium hydroxide, sodium carbonate, potassium carbonate or sodium hydrogencarbonate. The reaction of the compounds of the formulae VI and VII is generally carried out in an inert solvent, for example an alcohol such as methanol, ethanol or isopropanol, or an ether such as THF, dioxane or DME, or a mixture of solvents, at temperatures from about 20° C. to about 80° C., for example temperatures from about 40° C. to about 80° C., in the presence of a base, for example an alkoxide such as sodium methoxide, sodium ethoxide, potassium methoxide or potassium tert-butoxide.

The reaction of the compounds of the formulae VIII and IX is a nucleophilic substitution reaction at the carbon atom in the group Alk carrying the group $L^3$ and can be carried out under standard conditions for such reactions which are well known to a person skilled in the art. Generally the reaction is carried out in an inert solvent, for example a hydrocarbon or chlorinated hydrocarbon such as benzene, toluene, xylene, chlorobenzene, dichloromethane, chloroform or dichloroethane, an ether such as THF, dioxane, dibutyl ether, diisopropyl ether or DME, an alcohol such as methanol, ethanol or isopropanol, a ketone such as acetone or butan-2-one, an ester such as ethyl acetate or butyl acetate, a nitrile such as acetonitrile, an amide such as DMF or NMP, or a mixture of solvents, including two-phasic mixtures with aqueous solutions, at temperatures from about −20° C. to about 100° C., for example at temperatures from about −10° C. to about 30° C., depending on the particulars of the specific case. Generally it is favorable for enhancing the nucleophilicity of the compound of the formula VIII and/or binding an acid which is liberated during the reaction, to add a base, for example a tertiary amine, such as triethylamine, ethyldiisopropylamine or N-methylmorpholine, or an inorganic base such as an alkali metal hydride, hydroxide, carbonate or hydrogencarbonate like sodium hydride, sodium hydroxide, potassium hydroxide, sodium carbonate, potassium carbonate, cesium carbonate or sodium hydrogencarbonate, or an alkoxide or amide such as sodium methoxide, sodium ethoxide, potassium methoxide, potassium tert-butoxide, sodium amide or lithium diisopropylamide. A compound of the formula VIII can also be treated with a base and converted into a salt separately before the reaction with the compound of the formula IX.

The cyclization of the compound of the formula X to the compound of the formula XI can favorably be carried out in the presence of a phosphorus halide, such as phosphorus pentachloride or phosphorus oxychloride or a mixture thereof, in an inert solvent, for example a hydrocarbon or chlorinated hydrocarbon such as benzene, toluene, xylene, chlorobenzene, dichloromethane, chloroform or dichloroethane, at temperatures from about 20° C. to about 100° C., for example temperatures from about 50° C. to about 80° C.

The reaction of the compounds of the formulae XI and XII is another nucleophilic substitution reaction at the carbon atom in the group $R^1$ carrying the group $L^4$ and can be carried out under standard conditions for such reactions which are well known to a person skilled in the art. Generally the reaction is carried out in an inert solvent, for example a hydrocarbon or chlorinated hydrocarbon such as benzene, toluene, xylene, chlorobenzene, dichloromethane, chloroform or dichloroethane, an ether such as THF, dioxane, dibutyl ether, diisopropyl ether or DME, an alcohol such as methanol, ethanol or isopropanol, a ketone such as acetone or butan-2-one, an ester such as ethyl acetate or butyl acetate, a nitrile such as acetonitrile, an amide such as DMF or NMP, or a mixture of solvents, at temperatures from about 20° C. to about 100° C., for example at temperatures from about 40° C. to about 80° C., depending on the particulars of the specific case. Generally it is favorable for enhancing the nucleophilicity of the compound of the formula XI and/or binding an acid which is liberated during the reaction, to add a base, for example a tertiary amine, such as triethylamine, ethyldiisopropylamine or N-methylmorpholine, or an inorganic base such as an alkali metal hydride, hydroxide, carbonate or hydrogencarbonate like sodium hydride, sodium hydroxide, potassium hydroxide, sodium carbonate, potassium carbonate, cesium carbonate or sodium hydrogencarbonate, or an alkoxide or amide such as sodium methoxide, sodium ethoxide, potassium methoxide, potassium tert-butoxide, sodium amide or lithium diisopropylamide. A compound of the formula XI can still be treated with a base and converted into a salt separately before the reaction with the compound of the formula XII. Besides being prepared by reaction with a compound of the formula XII, a compound of the formula XI can also be converted into a compound of the formula XIII by reaction with the respective alcohol of the formula $R^1$—OH, wherein $R^1$ is defined as in the compounds of the formula I and additionally functional groups can be present in protected form or in the form of a precursor group, under the conditions of the Mitsunobu reaction in the presence of an azodicarboxylate such as diethyl azodicarboxylate or diisopropyl azodicarboxylate and a phosphine such as triphenylphosphine or tributylphosphine in an inert aprotic solvent, for example an ether such as THF or dioxane (cf. O. Mitsunobu, Synthesis (1981), 1-28).

The coupling of compounds of the formula XIII with compounds of the formula XIV can be carried out via reactions of various types as already indicated above, for example via an alkylation reaction. For example, if the group $R^2$ carries a hydroxy group representing $FG^1$, it can be alkylated using a compound of formula XIV in which $FG^2$ is a leaving group suitable for nucleophilic substitution reactions such as a halogen atom like chlorine, bromine or iodine, or a sulfonyloxy group like methanesulfonyloxy or toluenesulfonyloxy. The nucleophilic substitution reaction at the carbon atom in the group XIV carrying the group $FG^2$ can be carried out under standard conditions for such reactions which are well known to a person skilled in the art. Generally the reaction is carried out in an inert solvent, for example a hydrocarbon or chlorinated hydrocarbon such as benzene, toluene, xylene, chlorobenzene, dichloromethane, chloroform or dichloroethane, an ether such as THF, dioxane, dibutyl ether, diisopropyl ether or DME, an alcohol such as methanol, ethanol or isopropanol, a ketone such as acetone or butan-2-one, an ester such as ethyl acetate or butyl acetate, a nitrile such acetonitrile, an amide such as N,N-dimethylformamide or N-methylpyrrolidin-2-one, or a mixture of solvents, at temperatures from about 20° C. to about 100° C., for example at temperatures from about 40° C. to about 80° C., depending on the particulars of the specific case. Generally it is favorable for enhancing the nucleophilicity of the compound of the formula XIII and/or binding an acid which is liberated during the reaction, to add a base, for example a tertiary amine, such as triethylamine, ethyldiisopropylamine or N-methylmorpholine, or an inorganic base such as an alkaline metal hydride, hydroxide, carbonate or hydrogencarbonate like sodium hydride, sodium hydroxide, potassium hydroxide, sodium carbonate, potassium carbonate, cesium carbonate or sodium hydrogencarbonate, or an alkoxide or amide such as sodium methoxide, sodium ethoxide, potassium methoxide, potassium tert-butoxide, sodium amide or lithium diisopropylamide. A compound of the formula XIII in which $FG^1$ is hydroxy can also be treated with a base and converted into a salt separately before the reaction with the compound of the formula XIV. Besides by reaction with a compound of the formula XIV in which $FG^2$ is a leaving group as indicated, a compound of the formula XIII in which $FG^1$ is hydroxy can also be converted into a compound of the formula XV by reaction with the respective alcohol, i.e. with a compound of the formula XIV in which $FG^2$ is hydroxy, under the conditions of the Mitsunobu reaction specified above. The coupling of compounds of the formula XIII with compounds of the formula XIV via a transition metal-catalyzed reaction can also be performed under the conditions of palladium-catalyzed cross coupling reactions like the Heck, Stille or Suzuki coupling reaction (cf. A. de Meijere and F. Diederich (Eds.), Metal-Catalyzed Cross-Coupling Reactions (Wiley-VCH, 2004)).

The oxidation of the Alk-S— group in the compounds of the formula XV to the sulfoxide group or sulfone group in the compounds of the formula II can be carried out by means of hydrogen peroxide or a peracid such as 3-chloroperbenzoic acid or monoperoxyphthalic acid in an inert solvent, for example a chlorinated hydrocarbon such as dichloromethane or chloroform or an ester such as ethyl acetate or butyl acetate, at temperatures from about 0° C. to about 40° C., for example at about 20° C.

The sequence of steps in the preparation of the compounds of the formula X can also be changed and first an aminomalonic acid ester of the formula IV such as the diethyl ester can be reacted with thiourea in the presence of an alkali metal alkoxide such as sodium ethoxide, then the sulfur atom can be alkylated, for example methylated with iodomethane, and the obtained product acylated with a compound of the formula V (cf. M. H. Holschbach et al., Eur. J. Med. Chem. 41 (2006), 7-15).

Further compounds of the formula I can be obtained from suitable compounds prepared according to the above-described processes by functionalization or modification of functional groups contained therein according to standard procedures, for example by esterification, amidation, hydrolysis, etherification, alkylation, acylation, sulfonylation, reduction, oxidation, conversion into salts, and others. For example, a hydroxy group, which may be liberated from an ether group by ether cleavage, for example by means of boron tribromide, or from a protected hydroxy group by deprotection, can be esterified or etherified to give a carboxylic acid ester or a sulfonic acid ester. Etherifications of hydroxy groups can favorably be performed by alkylation with the respective halogen compound, for example a bromide or iodide, in the presence of a base, for example an alkali metal carbonate such as potassium carbonate or cesium carbonate in an inert solvent, for example an amide like DMF or NMP or a ketone like acetone or butan-2-one, or with the respective alcohol under the conditions of the Mitsunobu reaction referred to above. A hydroxy group can be converted into a halide by treatment with a halogenating agent. A halogen atom can be replaced with a variety of groups in a substitution reaction which may also be a transition-metal catalyzed reaction. A nitro group can be reduced to an amino group, for example by catalytic hydrogenation. An amino group can be modified under standard conditions for alkylation, for example by reaction with a halogen compound or by reductive amination of a carbonyl compound, or for acylation or sulfonylation, for example by reaction with a reactive carboxylic acid derivative, like an acid chloride or anhydride or a sulfonic acid chloride, or with an activated carboxylic acid which may be obtained from the carboxylic acid by treatment with a coupling agent like N,N'-carbonyldiimidazole (CDI), a carbodiimide such as 1,3-dicyclohexylcarbodiimide (DCC) or 1-(3-dimethylaminopropyl)-3-ethylcarbodiimide hydrochloride (EDC), O-(7-azabenzotriazol-1-yl)-N,N,N',N'-tetramethyluronium hexafluorophosphate (HATU), O-(cyano(ethoxycarbonyl)methyleneamino)-N,N,N',N'-tetramethyluronium tetrafluoroborate (TOTU), or [(benzotriazol-1-yloxy)-dimethylamino-methylene]-dimethyl-ammonium tetrafluoroborate (TBTU), for example. A carboxylic acid ester group can be hydrolyzed under acidic or basic conditions to give a carboxylic acid. A carboxylic acid group can be activated or converted into a reactive derivative as mentioned above and reacted with an alcohol or an amine or ammonia to give an ester or amide. A primary amide can be dehydrated to give a nitrile. A sulfur atom, for example in an alkyl-S— group or in a heterocyclic ring, can be oxidized with a peroxide like hydrogen peroxide or a peracid to give a sulfoxide moiety S(O) or a sulfone moiety $S(O)_2$. A carboxylic acid group, carboxylic acid ester group and a ketone group can be reduced to an alcohol, for example by means of a complex hydride such as lithium aluminium hydride, lithium borohydride or sodium borohydride. A compound of the formula I or an intermediate such as a compound of the formula II, which compound or intermediate contains a double bond or a triple bond in the group X, which can be readily obtained via a transition metal-catalyzed coupling reaction from a compound of the formula XIV containing a double or triple bond in the group $X^a$ and a compound of the formula XIII as outlined above, can be converted into a compound in which X is a saturated group, by hydrogenation in the presence of hydrogenation catalyst such as a palladium catalyst.

All reactions used in the above-described syntheses of the compounds of the formula I are per se well known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York. If desired, the obtained compounds of the formula I, as well as any intermediate compounds, can be purified by customary purification procedures, for example by recrystallization or chromatography. As already mentioned, all starting compounds and intermediates employed in the above-described syntheses which contain an acidic or basic group, can also be employed in the form of salts, and all intermediates and final target compounds can also be obtained in the form of salts. As likewise mentioned above, depending on the circumstances of the specific case, in order to avoid an unwanted course of a reaction or side reactions during the synthesis of a compound it can generally be necessary or advantageous to temporarily block functional groups by introducing protective groups and deprotect them again at a later stage of the synthesis, or to introduce functional groups in the form of precursor groups which later are converted into the desired functional groups. As examples of protecting groups, amino-protecting groups may be mentioned which can be acyl groups or alkyloxycarbonyl groups, for example a tert-butyloxycarbonyl group (=Boc) which can be removed by treatment with trifluoroacetic acid (=TFA), a benzyloxycarbonyl group which can be removed by catalytic hydrogenation, or a fluoren-9-ylmethoxycarbonyl group which can be removed by treatment with piperidine, and protecting groups of carboxylic acid groups which can be protected as ester groups, such as tert-butyl esters which can be deprotected by treatment with trifluoroacetic acid, or benzyl esters which can be deprotected by catalytic hydrogenation. As an example of a precursor group, the nitro group may be mentioned which can be converted into an amino group by reduction, for example by catalytic hydrogenation. Such synthesis strategies, and protective groups and precursor groups which are suitable in a specific case, are known to the skilled person.

Another subject of the present invention are the novel starting compounds and intermediates occurring in the synthesis of the compounds of the formula I, including the compounds of the formulae II, IIa, III, IV, V, VI, VIII, X, XI, XII, XIII, XIV and XV, wherein A, X, $X^a$, $R_1$, $R^2$, $R^3$, $R^4$, R', Alk, $FG^1$, $FG^2$, $L^1$, $L^2$ and $L^4$ are defined as above, in any of their stereoisomeric forms or a mixture of stereoisomeric forms in any ratio, and their salts, and solvates of any of them, and their use as intermediates. The invention also includes all tautomeric forms of the intermediates and starting compounds. All explanations and embodiments specified above with respect to the compounds of the formula I apply correspondingly also to the intermediates and starting compounds. A subject of the invention are in particular the novel specific starting compounds and intermediates disclosed herein. Irrespective of whether they are disclosed as a free compound and/or as a specific salt, they are a subject of the invention both in the form of the free compounds and in the form of their salts, and if a specific salt is disclosed, additionally in the form of this specific salt, and in the form of solvates of any of them.

The compounds of the formula I, optionally in combination with other pharmacologically active compounds, can be administered to animals, preferably to mammals including humans, as pharmaceuticals by themselves, in mixtures with one another, or in the form of pharmaceutical compositions. The administration can be carried out orally, for example in the form of tablets, film-coated tablets, sugar-coated tablets, granules, hard and soft gelatin capsules, solutions including aqueous, alcoholic and oily solutions, juices, drops, syrups, emulsions or suspensions, rectally, for example in the form of suppositories, or parenterally, for example in the form of solutions for subcutaneous, intramuscular or intravenous injection or infusion, in particular aqueous solutions. The compounds of the formula I can additionally be used in modes of local drug delivery, for example in coated stents for preventing or reducing in-stent restenosis or by applying them locally by means of a catheter. The appropriate administration form depends, among others, on the disease to be treated and on its severity.

The amount of a compound of the formula I and/or its physiologically acceptable salts and/or solvates present in the pharmaceutical compositions normally ranges from about 0.2 to about 800 mg, for example from about 0.5 to about 500 mg, for example from about 1 to about 200 mg, per unit dose, but depending on the type of the pharmaceutical composition it may also be higher. The pharmaceutical compositions usually comprise from about 0.5 to about 90 percent by weight of the compound of the formula I and/or its physiologically acceptable salts and/or solvates. The production of the pharmaceutical compositions can be carried out in a manner known per se. To this end, one or more compounds of the formula I and/or their physiologically acceptable salts and/or solvates together with one or more solid or liquid pharmaceutical carrier substances, or vehicles, and/or additives, or auxiliary substances, and, if a combination medicament is desired, other pharmacologically active compounds having therapeutic or prophylactic action are brought into a suitable form for administration and dosage which can then be used in human or veterinary medicine. As carrier substances and additives, suitable organic and inorganic substances can be used which do not react in an undesired manner with the compounds of the formula I or their physiologically acceptable salts or solvates. As examples of types of additives which can be contained in the pharmaceutical compositions and medicaments, lubricants, preservatives, thickeners, stabilizers, disintegrants, wetting agents, agents for achieving a depot effect, emulsifiers, salts, for example for influencing the osmotic pressure, buffer substances, colorants, flavorings and aromatic substances may be mentioned. Examples of carrier substances and additives are water, physiological sodium chloride solution, vegetable oils, waxes, alcohols such as ethanol, isopropanol, 1,2-propanediol, benzyl alcohols or glycerol, polyols, mannitol, polyethylene glycols, polypropylene glycols, glycerol triacetate, polyvinylpyrrolidone, gelatin, cellulose, carbohydrates such as lactose, glucose, saccharose or starch like corn starch, stearic acid and stearic acid salts such as magnesium stearate, talc, lanolin, petroleum jelly, or mixtures thereof, for example mixtures of water with one or more organic solvents such as mixtures of water with alcohols. The compounds of the formula I and their physiologically acceptable salts and solvates can also be lyophilized and the obtained lyophilisates used for the production of injectable compositions, for example.

The dosage of a compound of the formula I and/or a physiologically acceptable salt and/or solvate thereof to be administered depends on the specific case and, as is usual, has to be adapted by the physician according to the customary rules and procedures to the individual circumstances in order to achieve an optimum effect. It depends, for example, on the nature and the severity of the disorder to be treated, the sex, age, weight and individual responsiveness of the human or animal patient, on the efficacy and duration of action of the compound used, on whether the treatment is for the therapy of an acute or chronic disease or prophylactic, or on whether other active compounds are administered in addition to a compound of the formula I. In general, a daily dose from about 0.01 mg/kg to about 100 mg/kg, or from about 0.1 mg/kg to about 10 mg/kg, or from about 0.3 mg/kg to about 5 mg/kg (in each case mg per kg of bodyweight), for example, is appropriate for administration to an adult weighing 75 kg in order to obtain the desired results. The daily dose can be administered in a single dose or, in particular when larger amounts are administered, divided into several, for example two, three or four, individual doses. The administration can also be carried out continuously, for example by continuous infusion or injection. Depending on the individual behavior in a specific case, it may be necessary to deviate upward or downward from the indicated dosages.

The following examples illustrate the invention.

When example compounds containing a basic group were purified by preparative high pressure liquid chromatography (HPLC) on reversed phase (RP) column material and, as customary, the eluent was a gradient mixture of water and acetonitrile containing trifluoroacetic acid (TFA), they were in part obtained in the form of their acid addition salt with trifluoroacetic acid, depending on the details of the workup such as evaporation or lyophilization conditions. In the names of the example compounds and their structural formulae any such trifluoroacetic acid contained therein is not specified.

The prepared compounds were in general characterized by spectroscopic data and chromatographic data, in particular mass spectra (MS) and HPLC retention times (Rt; in min) which were obtained by combined analytical HPLC/MS characterization (LC/MS), and/or nuclear magnetic resonance (NMR) spectra. In the NMR characterization, the chemical shift δ (in ppm), the number of hydrogen atoms and the multiplicity (s=singlet, d=doublet, dd=double doublet, t=triplet, dt=double triplet, q=quartet, m=multiplet; br=broad) of the signals is given. In the MS characterization, in general the mass number (m/z) of the peak of the molecular ion M, e.g. $M^+$, or of a related ion such as the ion M+1, e.g. $[M+1]^+$, i.e. the protonated molecular ion $[M+H]^+$, which was formed depending on the ionization method used, is given. Generally, the ionization method was electrospray ionization (ESI). The LC/MS conditions used were as follows.

Method LC1

Column: UPLC BEH C18, 50×2.1 mm, 1.7 µm; flow: 0.9 ml/min; eluent A: acetonitrile+0.08% formic acid; eluent B: water+0.1% formic acid; gradient: from 5% A+95% B to 95% A+5% B in 1.1 min, then 95% A+5% B for 0.6 min; MS ionization method: ESI Method LC2

Column: UPLC BEH C18, 50×2.1 mm, 1.7 µm; flow: 0.9 ml/min; eluent A: acetonitrile+0.035% formic acid; eluent B: water+0.05% formic acid; gradient: from 5% A+95% B to 95% A+5% B in 1.1 min, then 95% A+5% B for 0.6 min; MS-ionization method: $ESI^+$ Method LC3

Column: Waters Xbridge C18, 50×4.6 mm, 2.5 µm; flow: 1.3 ml/min; eluent A: acetonitrile+0.1% formic acid; eluent B: water+0.1% formic acid; gradient: from 3% A+97% B to 60% A+40% B in 3.5 min, from 60% A+40% B to 98% A+2% B in 0.5 min, then to 98% A+2% B for 1 min; MS ionization method: $ESI^+$

EXAMPLE 1

{4-[5-(2,5-Difluoro-phenoxy)-7-propoxy-oxazolo[5,4-d]pyrimidin-2-yl]-2,6-dimethyl-phenoxy}-acetic acid

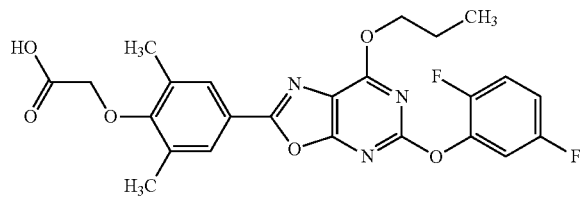 [SMILES: CCCOc1nc(Oc2cc(F)ccc2F)nc2oc(-c3cc(C)c(OCC(=O)O)c(C)c3)nc12]

(a) 2-(4-Methoxy-3,5-dimethyl-benzoylamino)-malonic acid diethyl ester 116.8 g of aminomalonic acid diethyl ester hydrochloride were dissolved in 700 ml of dichloromethane, and 231 ml of triethylamine were added with cooling in an ice bath. A solution of 109.6 g of 4-methoxy-3,5-dimethyl-benzoyl chloride in 400 ml of dichloromethane was slowly added dropwise. After 2 h at 0° C., 200 ml of water were added slowly. The phases were separated, and then the aqueous phase was extracted with 200 ml of dichloromethane twice. The combined organic phases were washed with 2 M hydrochloric acid and subsequently with water, dried with sodium sulfate, filtered and evaporated. The residue was treated with methyl tert-butyl ether, and then the resulting precipitate was isolated by filtration to give 178.7 g of the title compound.

(b) Sodium 4,6-dihydroxy-5-(4-methoxy-3,5-dimethyl-benzoylamino)-pyrimidine-2-thiolate 1.5 equivalents of sodium methoxide (30% solution in methanol) were added to 20.6 g of thiourea in 900 ml of absolute ethanol. 91 g of 2-(4-methoxy-3,5-dimethyl-benzoylamino)-malonic acid diethyl ester were added in small portions, and then the mixture was stirred at 60° C. for 3 h. Then the mixture was cooled to room temperature, and the precipitate was filtered off with suction, washed with 100 ml ethanol and 100 ml diethyl ether and dried in vacuo. 78.2 g of the crude title compound were obtained.

(c) N-(4,6-Dihydroxy-2-methylsulfanyl-pyrimidin-5-yl)-4-methoxy-3,5-dimethyl-benzamide 19.1 g of sodium 4,6-dihydroxy-5-(4-methoxy-3,5-dimethyl-benzoylamino)-pyrimidine-2-thiolate in 190 ml of water and 80 ml of N-methylpyrrolidin-2-one were cooled to 0° C. With cooling, 5.9 g of sodium hydroxide were added, and the mixture was then stirred at 0° C. for 30 min. Then a solution of 3.7 ml of iodomethane in 4.3 ml of N-methylpyrrolidin-2-one was added. After completion of the reaction (2 h), the mixture was acidified with concentrated hydrochloric acid. The resulting precipitate was isolated by suction, washed with water and dried in vacuo. 10.1 g of the title compound were obtained.

LC/MS (method LC1): Rt=1.03 min; m/z=336.1 [M+H]$^+$ (d) 2-(4-Methoxy-3,5-dimethyl-phenyl)-5-methylsulfanyl-oxazolo[5,4-d]pyrimidin-7-ol 10.1 g of N-(4,6-dihydroxy-2-methylsulfanyl-pyrimidin-5-yl)-4-methoxy-3,5-dimethyl-benzamide in 55 ml of phosphorus oxychloride were heated to 60° C. for 3 h. After cooling, the resulting solid was collected by filtration with suction and washed with methyl tert-butyl ether. The solid was then dissolved in a mixture of dichloromethane and tetrahydrofuran, washed with a saturated aqueous sodium hydrogencarbonate solution, dried and concentrated in vacuo. 5.9 g of the title compound were obtained.

LC/MS (method LC1): Rt=1.24 min; m/z=318.08 [M+H]$^+$ (e) 2-(4-Methoxy-3,5-dimethyl-phenyl)-5-methylsulfanyl-7-propoxy-oxazolo[5,4-d]pyrimidine 5.9 g of 2-(4-methoxy-3,5-dimethyl-phenyl)-5-methylsulfanyl-oxazolo[5,4-d]pyrimidin-7-ol were dissolved in 150 ml of N,N-dimethylformamide, and 7.7 g of potassium carbonate and then 2.7 g of 1-bromo-propane were added. The solution was stirred at 60° C. for 5 h and then, after cooling, poured onto 150 ml of water. The precipitate was filtered off with suction. The obtained mixture of regioisomers was purified by silica gel chromatography (50 g silica (solute cartridge, heptane/ethyl acetate 9/1). Besides 1.4 g of 2-(4-methoxy-3,5-dimethyl-phenyl)-5-methylsulfanyl-6-propyl-6H-oxazolo[5,4-d]pyrimidin-7-one (LC/MS (method LC1): Rt=1.43 min; m/z=360.13 [M+H]$^+$), 2.5 g of the title compound were obtained.

LC/MS (method LC1): Rt=1.51 min; m/z=360.13 [M+H]$^+$ (f) 2,6-Dimethyl-4-(5-methylsulfanyl-7-propoxy-oxazolo[5,4-d]pyrimidin-2-yl)-phenol To a solution of 2.5 g of 2-(4-methoxy-3,5-dimethyl-phenyl)-5-methylsulfanyl-7-propoxy-oxazolo[5,4-d]pyrimidine in 50 ml of dichloromethane 0.70 ml of boron tribromide were added slowly at −20° C. After 1 h at −20° C. and 2 h at room temperature, the mixture was quenched by addition of a saturated aqueous sodium hydrogencarbonate solution while maintaining a temperature below 5° C. The phases were separated, and then the aqueous phase was extracted twice with dichloromethane. The combined organic phases were dried and concentrated in vacuo. 2.0 g of the title compound were obtained.

LC/MS (method LC1): Rt=1.41 min; m/z=346.11 [M+H]$^+$ (g) [2,6-Dimethyl-4-(5-methylsulfanyl-7-propoxy-oxazolo[5,4-d]pyrimidin-2-yl)-phenoxy]-acetic acid tert-butyl ester To a solution of 2.00 g of 2,6-dimethyl-4-(5-methylsulfanyl-7-propoxy-oxazolo[5,4-d]pyrimidin-2-yl)-phenol in 20 ml of N,N-dimethylformamide was added 3.20 g of potassium carbonate, followed by 0.93 ml of tert-butyl bromoacetate. The mixture was reacted for 1 h at 60° C., then allowed to cool and poured onto water. The resulting precipitate was collected by filtration with suction and dried in vacuo. 2.45 g of the title compound were obtained.

LC/MS (method LC1): Rt=1.52 min; m/z=460.18 [M+H]$^+$ (h) [4-(5-Methanesulfonyl-7-propoxy-oxazolo[5,4-d]pyrimidin-2-yl)-2,6-dimethyl-phenoxy]-acetic acid tert-butyl ester 250 mg of [2,6-dimethyl-4-(5-methylsulfanyl-7-propoxy-oxazolo[5,4-d]pyrimidin-2-yl)-phenoxy]-acetic acid tert-butyl ester were dissolved in 5 ml of dichloromethane. At 0° C. then 268 mg of 3-chloroperbenzoic acid were added, and the mixture was then stirred at room temperature for 12 h. The mixture was treated with a 1 M aqueous solution of sodium hydroxide, then the layers were separated, after which the organic layer was extracted twice with dichloromethane. The combined organic phases were washed with a 10% aqueous solution of sodium hydrogensulfite, dried over sodium sulfate, filtered and evaporated in vacuo. 268 mg of the title compound were obtained.

LC/MS (method LC1): Rt=1.38 min; m z=492.17 [M+H]$^+$ (i) {4-[5-(2,5-Difluoro-phenoxy)-7-propoxy-oxazolo[5,4-d]pyrimidin-2-yl]-2,6-dimethyl-phenoxy}-acetic acid tert-butyl ester To a solution of 100 mg [4-(5-methanesulfonyl-7-propoxy-oxazolo[5,4-d]pyrimidin-2-yl)-2,6-dimethyl-phenoxy]-acetic acid tert-butyl ester in 1.5 ml of N,N-dimethylformamide were added 62 mg of potassium carbonate and 32 mg of 2,5-difluoro-phenol. The mixture was stirred at room temperature for 12 h. Then the mixture was poured onto water, neutralized by addition of a 10% aqueous solution of sodium hydrogensulfate, and extracted twice with ethyl acetate. The combined organic layers were dried and concentrated in vacuo. After filtration the solvent was distilled off in vacuo and the residue purified by preparative HPLC to yield 69 mg of the title compound.

LC/MS (method LC1): Rt=1.47 min; m/z=542.20 [M+H]$^+$ (j) {4-[5-(2,5-Difluoro-phenoxy)-7-propoxy-oxazolo[5,4-d]pyrimidin-2-yl]-2,6-dimethyl-phenoxy}-acetic acid 69 mg of {4-[5-(2,5-difluoro-phenoxy)-7-propoxy-oxazolo[5,4-d]pyrimidin-2-yl]-2,6-dimethyl-phenoxy}-acetic acid tert-butyl ester were dissolved in 1.6 ml of dichloromethane and treated with 0.8 ml of trifluoroacetic acid. After 16 h the mixture was concentrated and freeze-dried. 71 mg of the title compound were obtained.

LC/MS (method LC1): Rt=1.35 min; m/z=486.33 [M+H]$^+$

EXAMPLE 2

[4-(5-Cyclopentyloxy-7-propoxy-oxazolo[5,4-d]pyrimidin-2-yl)-2,6-dimethyl-phenoxy]-acetic acid

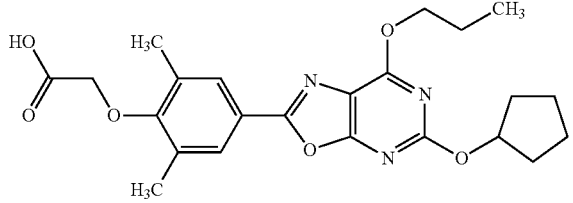 [SMILES: CCCOc1nc(OC2CCCC2)nc2oc(-c3cc(C)c(OCC(=O)O)c(C)c3)nc12]

(a) [4-(5-Cyclopentyloxy-7-propoxy-oxazolo[5,4-d]pyrimidin-2-yl)-2,6-dimethyl-phenoxy]-acetic acid tert-butyl ester A solution of 98 mg of [4-(5-methanesulfonyl-7-propoxy-oxazolo[5,4-d]pyrimidin-2-yl)-2,6-dimethyl-phenoxy]-acetic acid tert-butyl ester, 19 mg of cyclopentanol and 69 mg of (tert-butylimino)tris(pyrrolidino)phosphorane was reacted at room temperature for 16 h and subsequently heated in a microwave reactor to 100° C. for 10 min. The mixture was poured onto water and extracted twice with ethyl acetate. The combined organic layers were washed with a 10% aqueous solution of citric acid and brine, dried and evaporated. After purification by preparative HPLC, 27 mg of the title compound were obtained.

LC/MS (method LC1): Rt=1.56 min; m/z=498.25 [M+H]$^+$ (b) [4-(5-Cyclopentyloxy-7-propoxy-oxazolo[5,4-d]pyrimidin-2-yl)-2,6-dimethyl-phenoxy]-acetic acid 25 mg of [4-(5-cyclopentyloxy-7-propoxy-oxazolo[5,4-d]pyrimidin-2-yl)-2,6-dimethyl-phenoxy]-acetic acid tert-butyl ester were dissolved in 2 ml of dichloromethane and treated with 1 nil of trifluoroacetic acid. After 16 h the mixture was concentrated and freeze-dried. 24 mg of the title compound were obtained.

LC/MS (method LC1): Rt=1.31 min; m/z=442.1 [M+H]$^+$

EXAMPLE 3

{4-[5-(trans-2-Fluoro-cyclohexyloxy)-7-propoxy-oxazolo[5,4-d]pyrimidin-2-yl]-2,6-dimethyl-phenoxy}-acetic acid

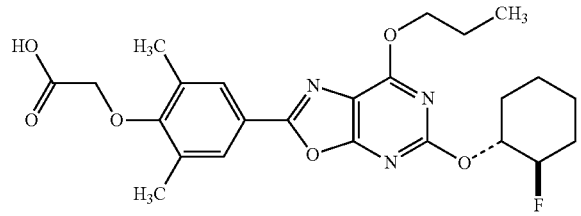

(a) {4-[5-(trans-2-Fluoro-cyclohexyloxy)-7-propoxy-oxazolo[5,4-d]pyrimidin-2-yl]-2,6-dimethyl-phenoxy}-acetic acid tert-butyl ester 26 mg of trans-2-fluoro-cyclohexanol were added under argon atmosphere at 0° C. to a suspension of 10 mg of sodium hydride (60% in mineral oil) in 2 ml of N,N-dimethylformamide. After 15 min a solution of 100 mg of [4-(5-methanesulfonyl-7-propoxy-oxazolo[5,4-d]pyrimidin-2-yl)-2,6-dimethyl-phenoxy]-acetic acid tert-butyl ester in 1 ml of N,N-dimethylformamide was slowly added. After 12 h at room temperature the mixture was quenched by the addition of water and extracted twice with ethyl acetate. The combined organic layers were dried and concentrated in vacuo. 101 mg of the title compound were obtained.

LC/MS (method LC1): Rt=1.49 min; m/z=530.26 [M+H]$^+$ and 552.26 [M+Na]$^+$ (b) {4-[5-(trans-2-Fluoro-cyclohexyloxy)-7-propoxy-oxazolo[5,4-d]pyrimidin-2-yl]-2,6-dimethyl-phenoxy}-acetic acid 98 mg of {4-[5-(trans-2-fluoro-cyclohexyloxy)-7-propoxy-oxazolo[5,4-d]pyrimidin-2-yl]-2,6-dimethyl-phenoxy}-acetic acid tert-butyl ester were dissolved in 3.5 ml of dichloromethane and treated with 1.5 ml of trifluoroacetic acid. After 16 h the mixture was concentrated and freeze-dried. 96 mg of the title compound were obtained.

LC/MS (method LC1): Rt=1.35 min; m/z=474.20 [M+H]$^+$

The compounds of the formula I listed in Table 1 were prepared analogously to the preparation of the example compounds described above. In part, they were obtained in the form of their trifluoroacetic acid salt.

TABLE 1

Example compounds of the formula I

| Example | Name | LC/MS | m/z [M + H]+ | Rt [min] |
|---|---|---|---|---|
| 4 | {4-[5-(2-fluoro-phenoxy)-7-propoxy-oxazolo[5,4-d]pyrimidin-2-yl]-2,6-dimethyl-phenoxy}-acetic acid | LC1 | 468.4 | 1.38 |
| 5 | {4-[5-(5-fluoro-2-methyl-phenoxy)-7-propoxy-oxazolo[5,4-d]pyrimidin-2-yl]-2,6-dimethyl-phenoxy}-acetic acid | LC1 | 482.26 | 1.36 |
| 6 | {4-[5-(3-fluoro-4-methyl-phenoxy)-7-propoxy-oxazolo[5,4-d]pyrimidin-2-yl]-2,6-dimethyl-phenoxy}-acetic acid | LC1 | 482.37 | 1.30 |
| 7 | {2,6-dimethyl-4-[7-propoxy-5-(pyridin-3-yloxy)-oxazolo[5,4-d]pyrimidin-2-yl]-phenoxy}-acetic acid | LC1 | 451.34 | 1.22 |
| 8 | {4-[5-(2,4-difluoro-phenoxy)-7-propoxy-oxazolo[5,4-d]pyrimidin-2-yl]-2,6-dimethyl-phenoxy}-acetic acid | LC1 | 486.32 | 1.35 |
| 9 | [2,6-dimethyl-4-(5-phenoxy-7-propoxy-oxazolo[5,4-d]pyrimidin-2-yl)-phenoxy]-acetic acid | LC1 | 450.32 | 1.35 |
| 10 | {4-[5-(3-chloro-phenoxy)-7-propoxy-oxazolo[5,4-d]pyrimidin-2-yl]-2,6-dimethyl-phenoxy}-acetic acid | LC1 | 483.86 | 1.30 |
| 11 | [4-(5-cyclohexylmethoxy-7-propoxy-oxazolo[5,4-d]pyrimidin-2-yl)-2,6-dimethyl-phenoxy]-acetic acid | LC1 | 470.44 | 1.38 |
| 12 | [4-(5-isobutoxy-7-propoxy-oxazolo[5,4-d]pyrimidin-2-yl)-2,6-dimethyl-phenoxy]-acetic acid | LC1 | 430.29 | 1.42 |
| 13 | [4-(5-cyclobutylmethoxy-7-propoxy-oxazolo[5,4-d]pyrimidin-2-yl)-2,6-dimethyl-phenoxy]-acetic acid | LC1 | 442.30 | 1.43 |
| 14 | [4-(5-cyclobutoxy-7-propoxy-oxazolo[5,4-d]pyrimidin-2-yl)-2,6-dimethyl-phenoxy]-acetic acid | LC1 | 428.27 | 1.40 |
| 15 | [4-(5,7-dipropoxy-oxazolo[5,4-d]pyrimidin-2-yl)-2,6-dimethyl-phenoxy]-acetic acid | LC1 | 416.28 | 1.38 |
| 16 | {2,6-dimethyl-4-[7-propoxy-5-(3,3,3-trifluoro-propoxy)-oxazolo[5,4-d]pyrimidin-2-yl]-phenoxy}-acetic acid | LC1 | 470.25 | 1.35 |
| 17 | [4-(5-ethoxy-7-propoxy-oxazolo[5,4-d]pyrimidin-2-yl)-2,6-dimethyl-phenoxy]-acetic acid | LC1 | 402.26 | 1.34 |
| 18 | [4-(5-cyclopentylmethoxy-7-propoxy-oxazolo[5,4-d]pyrimidin-2-yl)-2,6-dimethyl-phenoxy]-acetic acid | LC1 | 456.30 | 1.46 |
| 19 | {2,6-dimethyl-4-[7-propoxy-5-(tetrahydrofuran-2-ylmethoxy)-oxazolo[5,4-d]pyrimidin-2-yl]-phenoxy}-acetic acid | LC1 | 458.28 | 1.31 |
| 20 | [4-(5-sec-butoxy-7-propoxy-oxazolo[5,4-d]pyrimidin-2-yl)-2,6-dimethyl-phenoxy]-acetic acid | LC1 | 430.29 | 1.40 |
| 21 | {2,6-dimethyl-4-[7-propoxy-5-(3,3,3-trifluoro-1-methyl-propoxy)-oxazolo[5,4--d]pyrimidin-2-yl]-phenoxy}-acetic acid | LC1 | 484.28 | 1.37 |
| 22 | {2,6-dimethyl-4-[5-(3-methyl-butoxy)-7-propoxy-oxazolo[5,4-d]pyrimidin-2-yl]-phenoxy}-acetic acid | LC1 | 444.32 | 1.44 |
| 23 | {4-[5-(2-cyclopropyl-ethoxy)-7-propoxy-oxazolo[5,4-d]pyrimidin-2-yl]-2,6-dimethyl-phenoxy}-acetic acid | LC1 | 442.31 | 1.41 |
| 24 | {2,6-dimethyl-4-[7-propoxy-5-(2,2,2-trifluoro-1-methyl-ethoxy)-oxazolo[5,4-d]pyrimidin-2-yl]-phenoxy}-acetic acid | LC1 | 470.25 | 1.38 |
| 25 | {4-[7-ethoxy-5-(3-fluorophenoxy)-oxazolo[5,4-d]pyrimidin-2-yl]-2,6-dimethyl-phenoxy}-acetic acid | LC2 | 454.15 | 1.35 |
| 26 | {4-[7-ethoxy-5-(2-fluorophenoxy)-oxazolo[5,4-d]pyrimidin-2-yl]-2,6-dimethyl-phenoxy}-acetic acid | LC2 | 454.16 | 1.34 |
| 27 | {4-[5-(isothiazol-3-yloxy)-7-propoxy-oxazolo[5,4-d]pyrimidin-2-yl]-2,6-dimethylphenoxy}-acetic acid | LC2 | 457.11 | 1.31 |
| 28 | {2,6-dimethyl-4-[7-propoxy-5-([1,2,5]thiadiazol-3-yloxy)-oxazolo[5,4-d]pyrimidin-2-yl]-phenoxy}-acetic acid | LC2 | 458.09 | 1.34 |

TABLE 1-continued

Example compounds of the formula I

| Example | Name | LC/MS | m/z [M + H]+ | Rt [min] |
|---|---|---|---|---|
| 29 | [2,6-dimethyl-4-(7-propoxy-5-(3-methylphenoxy)-oxazolo[5,4-d]pyrimidin-2-yl)-phenoxy]-acetic acid | LC2 | 464.17 | 1.41 |
| 30 | [2,6-dimethyl-4-(7-propoxy-5-(2-methylphenoxy)-oxazolo[5,4-d]pyrimidin-2-yl)-phenoxy]-acetic acid | LC2 | 464.17 | 1.41 |
| 31 | [2,6-dimethyl-4-(7-propoxy-5-(4-methylphenoxy)-oxazolo[5,4-d]pyrimidin-2-yl)-phenoxy]-acetic acid | LC3 | 464.17 | 4.98 |
| 32 | {2,6-dimethyl-4-[5-(6-methylpyridin-3-yloxy)-7-propoxy-oxazolo[5,4-d]pyrimidin-2-yl]-phenoxy}-acetic acid | LC3 | 465.16 | 4.2 |
| 33 | {2,6-dimethyl-4-[5-(5-methylpyridin-3-yloxy)-7-propoxy-oxazolo[5,4-d]pyrimidin-2-yl]-phenoxy}-acetic acid | LC2 | 465.19 | 1.28 |
| 34 | {4-[5-(3-fluorophenoxy)-7-propoxy-oxazolo[5,4-d]pyrimidin-2-yl]-2,6-dimethyl-phenoxy}-acetic acid | LC2 | 468.15 | 1.39 |
| 35 | {4-[5-(4-fluorophenoxy)-7-propoxy-oxazolo[5,4-d]pyrimidin-2-yl]-2,6-dimethylphenoxy}-acetic acid | LC2 | 468.16 | 1.38 |
| 36 | {4-[7-ethoxy-5-(5-fluoro-2-methylphenoxy)-oxazolo[5,4-d]pyrimidin-2-yl]-2,6-dimethyl-phenoxy}-acetic acid | LC2 | 468.17 | 1.38 |
| 37 | {4-[5-(5-fluoropyridin-3-yloxy)-7-propoxy-oxazolo[5,4-d]pyrimidin-2-yl]-2,6-dimethyl-phenoxy}-acetic acid | LC2 | 469.14 | 1.31 |
| 38 | {4-[5-(3-chlorophenoxy)-7-ethoxy-oxazolo[5,4-d]pyrimidin-2-yl]-2,6-dimethyl-phenoxy}-acetic acid | LC2 | 470.13 | 1.39 |
| 39 | {4-[5-(2,5-difluorophenoxy)-7-ethoxy-oxazolo[5,4-d]pyrimidin-2-yl]-2,6-dimethyl-phenoxy}-acetic acid | LC2 | 472.14 | 1.35 |
| 40 | {4-[5-(3-ethylphenoxy)-7-propoxy-oxazolo[5,4-d]pyrimidin-2-yl]-2,6-dimethyl-phenoxy}-acetic acid | LC2 | 478.19 | 1.44 |
| 41 | {4-[5-(3-methoxyphenoxy)-7-propoxy-oxazolo[5,4-d]pyrimidin-2-yl]-2,6-dimethylphenoxy}-acetic acid | LC1 | 480.2 | 1.24 |
| 42 | {4-[5-(3-fluoro-5-methylphenoxy)-7-propoxy-oxazolo[5,4-d]pyrimidin-2-yl]-2,6-dimethyl-phenoxy}-acetic acid | LC2 | 482.15 | 1.42 |
| 43 | {4-[5-(4-fluoro-3-methylphenoxy)-7-propoxy-oxazolo[5,4-d]pyrimidin-2-yl]-2,6-dimethyl-phenoxy}-acetic acid | LC2 | 482.18 | 1.41 |
| 44 | {4-[5-(2-fluoro-4-methylphenoxy)-7-propoxy-oxazolo[5,4-d]pyrimidin-2-yl]-2,6-dimethylphenoxy}-acetic acid | LC1 | 482.2 | 1.41 |
| 45 | {4-[5-(2-fluoro-5-methylphenoxy)-7-propoxy-oxazolo[5,4-d]pyrimidin-2-yl]-2,6-dimethylphenoxy}-acetic acid | LC1 | 482.2 | 1.41 |
| 46 | {4-[5-(4-chlorophenoxy)-7-propoxy-oxazolo[5,4-d]pyrimidin-2-yl]-2,6-dimethylphenoxy}-acetic acid | LC2 | 484.14 | 1.42 |
| 47 | {4-[5-(2-chlorophenoxy)-7-propoxy-oxazolo[5,4-d]pyrimidin-2-yl]-2,6-dimethylphenoxy}-acetic acid | LC1 | 484.17 | 1.4 |
| 48 | {4-[5-(5-chloropyridin-3-yloxy)-7-propoxy-oxazolo[5,4-d]pyrimidin-2-yl]-2,6-dimethyl-phenoxy}-acetic acid | LC2 | 485.11 | 1.36 |
| 49 | {4-[5-(2,3-difluorophenoxy)-7-propoxy-oxazolo[5,4-d]pyrimidin-2-yl]-2,6-dimethylphenoxy}-acetic acid | LC2 | 486.14 | 1.39 |
| 50 | {4-[5-(3,5-difluorophenoxy)-7-propoxy-oxazolo[5,4-d]pyrimidin-2-yl]-2,6-dimethyl-phenoxy}-acetic acid | LC2 | 486.15 | 1.4 |
| 51 | {4-[5-(3,4-difluorophenoxy)-7-propoxy-oxazolo[5,4-d]pyrimidin-2-yl]-2,6-dimethylphenoxy}-acetic acid | LC2 | 486.16 | 1.39 |
| 52 | {4-[5-(indan-4-yloxy)-7-propoxy-oxazolo[5,4-d]pyrimidin-2-yl]-2,6-dimethylphenoxy}-acetic acid | LC2 | 490.2 | 1.45 |
| 53 | {4-[5-(indan-5-yloxy)-7-propoxy-oxazolo[5,4-d]pyrimidin-2-yl]-2,6-dimethylphenoxy}-acetic acid | LC1 | 490.26 | 1.45 |

TABLE 1-continued

Example compounds of the formula I

| Example | Name | LC/MS | m/z [M + H]⁺ | Rt [min] |
|---|---|---|---|---|
| 54 | {4-[5-(3-chloro-2-methylphenoxy)-7-propoxy-oxazolo[5,4-d]pyrimidin-2-yl]-2,6-dimethyl-phenoxy}-acetic acid | LC2 | 498.13 | 1.45 |
| 55 | {4-[5-(3-chloro-4-methylphenoxy)-7-propoxy-oxazolo[5,4-d]pyrimidin-2-yl]-2,6-dimethylphenoxy}-acetic acid | LC2 | 498.15 | 1.46 |
| 56 | {4-[5-(5-chloro-2-methylphenoxy)-7-propoxy-oxazolo[5,4-d]pyrimidin-2-yl]-2,6-dimethyl-phenoxy}-acetic acid | LC2 | 498.16 | 1.45 |
| 57 | {2,6-dimethyl-4-[5-(naphthalen-2-yloxy)-7-propoxy-oxazolo[5,4-d]pyrimidin-2-yl]-phenoxy}-acetic acid | LC2 | 500.18 | 1.43 |
| 58 | {2,6-dimethyl-4-[7-propoxy-5-(quinolin-3-yloxy)-oxazolo[5,4-d]pyrimidin-2-yl]-phenoxy}-acetic acid | LC2 | 501.19 | 1.35 |
| 59 | {4-[5-(4-chloro-2-fluorophenoxy)-7-propoxy-oxazolo[5,4-d]pyrimidin-2-yl]-2,6-dimethyl-phenoxy}-acetic acid | LC2 | 502.11 | 1.42 |
| 60 | {4-[5-(3-chloro-5-fluorophenoxy)-7-propoxy-oxazolo[5,4-d]pyrimidin-2-yl]-2,6-dimethyl-phenoxy}-acetic acid | LC2 | 502.12 | 1.44 |
| 61 | {4-[5-(2-chloro-4-fluorophenoxy)-7-propoxy-oxazolo[5,4-d]pyrimidin-2-yl]-2,6-dimethyl-phenoxy}-acetic acid | LC2 | 502.13 | 1.41 |
| 62 | {4-[5-(3-chloro-4-fluorophenoxy)-7-propoxy-oxazolo[5,4-d]pyrimidin-2-yl]-2,6-dimethylphenoxy}-acetic acid | LC2 | 502.13 | 1.42 |
| 63 | {4-[5-(3-chloro-2-fluorophenoxy)-7-propoxy-oxazolo[5,4-d]pyrimidin-2-yl]-2,6-dimethyl-phenoxy}-acetic acid | LC2 | 502.14 | 1.42 |
| 64 | {4-[5-(4-chloro-3-fluorophenoxy)-7-propoxy-oxazolo[5,4-d]pyrimidin-2-yl]-2,6-dimethylphenoxy}-acetic acid | LC2 | 502.14 | 1.43 |
| 65 | {4-[5-(2-chloro-5-fluorophenoxy)-7-propoxy-oxazolo[5,4-d]pyrimidin-2-yl]-2,6-dimethylphenoxy}-acetic acid | LC2 | 502.14 | 1.41 |
| 66 | {4-[5-(benzothiazol-6-yloxy)-7-propoxy-oxazolo[5,4-d]pyrimidin-2-yl]-2,6-dimethylphenoxy}-acetic acid | LC2 | 507.12 | 1.33 |
| 67 | {2,6-dimethyl-4-[7-propoxy-5-(3-trifluoromethylphenoxy)-oxazolo[5,4-d]pyrimidin-2-yl]-phenoxy}-acetic acid | LC2 | 518.18 | 1.42 |
| 68 | {2,6-dimethyl-4-[7-propoxy-5-(4-trifluoromethylphenoxy)-oxazolo[5,4-d]pyrimidin-2-yl]-phenoxy}-acetic acid | LC2 | 518.18 | 1.42 |
| 69 | {2,6-dimethyl-4-[7-propoxy-5-(2-trifluoromethylphenoxy)-oxazolo[5,4-d]pyrimidin-2-yl]-phenoxy}-acetic acid | LC1 | 518.22 | 1.4 |
| 70 | {2,6-dimethyl-4-[5-(2-methylbenzothiazol-5-yloxy)-7-propoxy-oxazolo[5,4-d]pyrimidin-2-yl]-phenoxy}-acetic acid | LC2 | 521.15 | 1.37 |
| 71 | {2,6-dimethyl-4-[7-propoxy-5-(2-trifluoromethoxyphenoxy)-oxazolo[5,4-d]pyrimidin-2-yl]-phenoxy}-acetic acid | LC2 | 534.16 | 1.41 |
| 72 | {4-[5-(2-fluoro-3-trifluoromethylphenoxy)-7-propoxy-oxazolo[5,4-d]pyrimidin-2-yl]-2,6-dimethyl-phenoxy}-acetic acid | LC2 | 536.13 | 1.42 |
| 73 | {4-[5-(2-fluoro-5-trifluoromethylphenoxy)-7-propoxy-oxazolo[5,4-d]pyrimidin-2-yl]-2,6-dimethylphenoxy}-acetic acid | LC2 | 536.14 | 1.42 |
| 74 | {4-[5-(4-fluoro-3-trifluoromethylphenoxy)-7-propoxy-oxazolo[5,4-d]pyrimidin-2-yl]-2,6-dimethyl-phenoxy}-acetic acid | LC2 | 536.15 | 1.42 |
| 75 | {4-[5-(3-fluoro-5-trifluoromethylphenoxy)-7-propoxy-oxazolo[5,4-d]pyrimidin-2-yl]-2,6-dimethyl-phenoxy}-acetic acid | LC2 | 536.16 | 1.44 |
| 76 | {2,6-dimethyl-4-[7-propoxy-5-(3-trifluoromethylsulfanyl-phenoxy)-oxazolo[5,4-d]pyrimidin-2-yl]-phenoxy}-acetic acid | LC2 | 550.11 | 1.46 |
| 77 | {4-[5-(2-chloro-5-trifluoromethylphenoxy)-7-propoxy-oxazolo[5,4-d]pyrimidin-2-yl]-2,6-dimethyl-phenoxy}-acetic acid | LC2 | 552.11 | 1.44 |
| 78 | {4-[5-(4-chloro-3-trifluoromethylphenoxy)-7-propoxy-oxazolo[5,4-d]pyrimidin-2-yl]-2,6-dimethylphenoxy}-acetic acid | LC2 | 552.11 | 1.45 |

TABLE 1-continued

Example compounds of the formula I

| Example | Name | LC/MS | m/z [M + H]+ | Rt [min] |
|---|---|---|---|---|
| 79 | {4-[5-(2-chloro-3-trifluoromethylphenoxy)-7-propoxy-oxazolo[5,4-d]pyrimidin-2-yl]-2,6-dimethylphenoxy}-acetic acid | LC2 | 552.11 | 1.43 |

Determination of the Pharmacological Activity

A) GTP-γ-S Assay Using Human Edg-1 Receptors

In order to determine the Edg-1 receptor activation by the compounds of the invention, a GTP-γ-S (guanosine 5'-[thio] triphosphate) assay for G-protein coupled receptor binding based on the scintillation proximity assay principle was used, employing a cell membrane preparation from a CHO Flp-In cell line which constitutively overexpresses the human Edg-1 receptor.

(a) Cell Line Generation

The Flp-In™ expression system (Invitrogen, cat. no. K6010-01) allows the generation of stable mammalian cell lines into which the gene of interest has been integrated through homologous recombination at a specific genomic location called Flp Recombination Target (FRT) site by means of a Flp recombinase encoded by the pOG44 expression plasmid. The integration of the pcDNA5/FRT expression construct into the Flp-In host cell line genome results in the transcription of the gene of interest. The stably transfected cells become hygromycin-resistant.

One day prior to transfection, 200 000 Flp-In-CHO cells were seeded in Ham F-12 medium (Invitrogen, cat. no. 31765) supplemented with 10% fetal calf serum (FCS; Perbio Science, cat. no. SH30068.03) in a 6-well plate and incubated at 37° C./5% $CO_2$ overnight. Using the FuGENE® 6 transfection reagent (Roche, cat. no. 11988387001), cells were cotransfected with the Flp recombinase expression plasmid pOG44 and a modified plasmid additionally containing the edg-1 gene (accession no. NM_001400) termed as pcDNA5-FRT-TO_nFLAG_DEST-EDG-1 with a 9:1 ratio. To obtain the modified pcDNA5-FRT-TO_nFLAG_DEST plasmid, the Invitrogen plasmid pcDNA5/FRT/TO (Invitrogen, cat. no. V6520-20) was adapted to the Gateway® (Invitrogen) cloning system by inserting a Gateway cassette containing attR recombination sites flanking a ccdB gene and a chloramphenicol-resistance gene (Gateway conversion system, Invitrogen, cat. no. 11828-029). In addition a FLAG tag epitope was added before the 5' att recombination site to allow recombinant expression of N-terminally FLAG-tagged proteins.

For the transfection of one well, 1.08 µg of pOG44 and 0.12 µg of pcDNA5-FRT-TO_nFLAG_DEST-EDG-1 were mixed to 100 µl of serum-free Ham F-12 medium containing 6 µl of FuGENE® 6 transfection reagent. After 20 min of incubation, the transfection reagent/DNA complex was distributed dropwise on the cells. The cells were incubated for 24 h at 37° C. Then the cells from 3 wells were transferred to a T75 flask (Greiner Cellstar®, cat. no. 658175) containing Ham F-12 medium supplemented with 10% of FCS but without antibiotic and were incubated another 24 h. 48 h after transfection, the medium was replaced by selection medium (Ham F-12 supplemented with 10% of FCS and 300 µg/ml of hygromycin B (Invitrogen, cat. no. 10687-010)). The medium was exchanged every 2 to 3 days until a resistant population of cells had grown. Cells were split several times and seeded into a new flask so that the cells did not reach more than 25% of confluency. After 2 weeks of selection, the cells were transferred into T175 flasks (Greiner Cellstar®, cat. no. 660175) and cultivated for batch production. Cells were harvested from the culture flasks by short treatment (2 to 5 min) with Accutase (PAA, cat. no. L11-007), resuspended in selection medium (see above) and centrifuged at 200×g for 5 min. The cells were resuspended in a mixture of 90% of FCS and 10% of dimethylsulfoxide and stored frozen in liquid nitrogen.

(b) Membrane Preparation

A membrane preparation was obtained by standard methods from the afore-described CHO Flp-In cell line constitutively overexpressing the human Edg-1 receptor. Briefly, the cryopreserved cells were taken in culture and grown until confluency in T175 cell culture flasks (Becton Dickinson, cat. no. 35 5001). The cell culture was stopped by washing with calcium-free phosphate-buffered saline (PBS; Gibco, cat. no. 14190), and the cells were harvested with a rubber-policeman in 4° C. cold and calcium-free PBS supplemented with a protease inhibitor cocktail (complete protease inhibitor; Roche, cat. no. 1697498; 1 tablet per 50 ml) and subsequently centrifuged at 4° C. for 15 min at 1100×g (Heraeus Minifuge T). For cell lysis, the pellet was resuspended in a 4° C. cold hypotonic buffer consisting of 5 mM HEPES (Sigma-Aldrich, cat. no. H-0981), 1 mM EDTA (disodium salt; Merck, cat. No. 8418) supplemented with protease inhibitor cocktail (as above) in which the cells were stored for another 15 min on ice. After lysis, the cells were centrifuged at 4° C. for 10 min at 400×g (Heraeus Minifuge T). The pellet was disrupted in a Dounce homogenizer, diluted with the supernatant of the previous centrifugation and subsequently centrifuged at 4° C. for 10 min at 500×g (Heraeus Minifuge T) in order to separate nuclei and still intact cells from the membranes mainly present in the supernatant. The supernatant was then diluted in hypotonic buffer and centrifuged (Beckmann, Avanti J251) at approximately 18600×g for 2 h at 4° C. After centrifugation, the membrane pellet was resuspended in a storing buffer consisting of 20 mM HEPES; 150 mM NaCl (Merck, cat. no. 6400), 1 mM EDTA (as above) supplemented with protease inhibitor cocktail (as above). The membrane preparation was aliquoted and stored at -80° C. The protein concentration of the membrane preparation was determined in a sample by means of a commercial protein assay (Bio-Rad, DC Protein Assay, cat. nos. 500-0113, 500-0114, 500-0115).

(c) GTP-γ-S Assay

The Edg-1 membrane preparation obtained in (b) was employed in a commercially available scintillation proximity assay (SPA) kit for G-protein coupled receptor binding from Amersham Biosciences/GE Healthcare (code RPNQ0210), in which ligand-induced binding of $^{35}$S-radiolabeled GTP-γ-S to the receptor-containing membrane, which is bound to scintillation beads, stimulates the emission of light and allows quantification of the in vitro activity of the Edg-1 agonistic compound. The assay was performed on a 96-well plate substantially according to the manufacturer's instructions. Before start of the experiments, scintillation beads were suspended in a reconstitution buffer consisting of Tris-HCl (pH 7.4) supplemented with 0.1% (w/v) sodium azide and subsequently diluted on ice with assay buffer (consisting of 20 mM HEPES, 100 mM NaCl, 1 mM EDTA (as above), 1 mM dithiothreitol (DTT), adjusted to pH 7.4) to a final bead concentration of 30 mg/ml.

The wells were charged with 10 µl of the specified assay buffer, 10 µl of a 100 µM guanosine diphosphate (GDP) solution, and 10 µl of a solution of the test compound in assay buffer/dimethylsulfoxide resulting in a final concentration of the test compound of 10 µM. For the high controls, 10 µl of a solution of sphingosine-1-phosphate (S1P; Sigma, cat. no. S-9666), resulting in a final S1P concentration of 10 µM, and for the low controls 10 µl of assay buffer, were added into the respective wells instead of the solution of the test compound. All wells contained equivalent amounts of dimethylsulfoxide. Then 10 µl of a [$^{35}$S]GTP-γ-S solution (4 nM) and the Edg-1 membrane preparation obtained in (b) (15 µg membrane protein in 100 µl of assay buffer) were added to each well. After incubation of the plates at room temperature for 5 min, 50 µl of the specified scintillation bead suspension (30 mg/ml) was added. After a further incubation period of 45 min at room temperature, plates were centrifuged for 10 min at 500×g. Quantification of [$^{35}$S]GTP-γ-S binding and thus receptor activation was measured by means of a beta counter (MicroBeta, Wallac) over 1 min. The values were background-corrected by subtraction of the respective low control. All measurements were made in triplicate. The receptor activation by the test compound is expressed in percent of the respective high control (10 µM S1P; regarded as 100% activation). In Table 2 activations observed with example compounds at 10 µM are listed.

TABLE 2

Edg-1 receptor activation by example compounds at 10 µM in percent of the activation by 10 µM S1P

| Example | % Activation |
|---|---|
| 1 | 100 |
| 2 | 90 |
| 3 | 65 |
| 4 | 76 |
| 5 | 91 |
| 6 | 73 |
| 7 | 87 |
| 8 | 84 |
| 9 | 84 |
| 10 | 86 |
| 11 | 76 |
| 12 | 97 |
| 13 | 99 |
| 14 | 88 |
| 15 | 98 |
| 16 | 107 |
| 17 | 70 |
| 18 | 83 |
| 19 | 84 |
| 20 | 80 |
| 21 | 81 |
| 22 | 92 |
| 23 | 98 |
| 24 | 85 |
| 25 | 84 |
| 26 | 127 |
| 27 | 109 |
| 28 | 83 |
| 29 | 75 |
| 30 | 97 |
| 31 | 72 |
| 32 | 114 |
| 33 | 110 |
| 34 | 48 |
| 35 | 79 |
| 36 | 116 |
| 37 | 117 |
| 38 | 55 |
| 39 | 121 |
| 40 | 95 |
| 41 | 73 |
| 42 | 66 |
| 43 | 60 |
| 44 | 43 |
| 45 | 67 |
| 46 | 59 |
| 47 | 86 |
| 48 | 115 |
| 49 | 103 |
| 50 | 86 |
| 51 | 49 |
| 52 | 54 |
| 53 | 55 |
| 54 | 107 |
| 55 | 66 |
| 56 | 78 |
| 57 | 58 |
| 58 | 75 |
| 59 | 72 |
| 60 | 59 |
| 61 | 97 |
| 62 | 56 |
| 63 | 67 |
| 64 | 65 |
| 65 | 105 |
| 66 | 102 |
| 67 | 82 |
| 68 | 69 |
| 69 | 67 |
| 70 | 89 |
| 71 | 62 |
| 72 | 48 |
| 73 | 59 |
| 74 | 61 |
| 75 | 48 |
| 76 | 81 |
| 77 | 77 |
| 78 | 72 |
| 79 | 82 |

It is evident from the measurement data that the compounds are highly suited to wound healing and in particular for treating wound healing disorders in diabetic patients.

The invention claimed is:

1. A compound of formula I, in any of its stereoisomeric forms, or a mixture of stereoisomeric forms in any ratio, or a physiologically acceptable salt thereof, or a physiologically acceptable solvate of any of them,

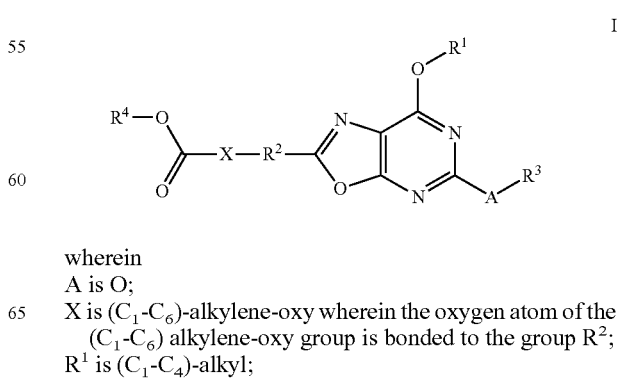

wherein
A is O;
X is ($C_1$-$C_6$)-alkylene-oxy wherein the oxygen atom of the ($C_1$-$C_6$) alkylene-oxy group is bonded to the group $R^2$;
$R^1$ is ($C_1$-$C_4$)-alkyl;

$R^2$ is phenylene substituted with $(R_5)m$, wherein $R_5$ is $(C_1-C_4)$-alkyl and m is selected from the group consisting of 1 and 2;

$R^3$ is selected from the group consisting of $(C_1-C_6)$-alkyl, $(C_3-C_7)$-cycloalkyl-$C_uH_{2u}$—, $(C_3-C_7)$-heterocycle, $(C_5-C_9)$-aryl, and $(C_5-C_9)$-heteroaryl, wherein the $(C_1-C_6)$-alkyl, $(C_3-C_7)$-cycloalkyl-$C_uH_{2u}$—, $C_3-C_7)$-heterocycle, $(C_5-C_9)$-aryl, and $(C_5-C_9)$-heteroaryl may each independently be substituted with one, two, or three substituents selected from the group consisting of halo, $(C_1-C_4)$-alkyl, trifluoromethyl, and trifluoromethylsulfonyl, and further wherein u is selected from the group consisting of 1 and 2; and $R^4$ is selected from the group consisting of hydrogen and $(C_1-C_4)$-alkyl.

2. The compound of formula I, in any of its stereoisomeric forms, or a mixture of stereoisoersric forms in any ratio, or a physiologically acceptable salt thereof, or a physiologically acceptable solvate of any of them, as claimed in claim 1,
wherein $R^3$ is selected from the group consisting of $(C_1-C_6)$-alkyl and $(C_3-C_7)$-cycloalkyl-$C_uH_{2u}$—.

3. The compound of formula I, in any of its stereoisomeric forms, or a mixture of stereoisomeric forms in any ratio, or a physiologically acceptable salt thereof, or a physiologically acceptable solvate of any of them, as claimed in claim 1, wherein
$R^3$ is $(C_3-C_7)$-cycloalkyl-$C_uH_{2u}$—.

4. The compound of formula I, in any of its stereoisomeric forms, or a mixture of stereoisomeric forms in any ratio, or a physiologically acceptable salt thereof, or a physiologically acceptable solvate of any of them, as claimed in claim 1,
wherein m is 2.

5. The compound of formula I, or a physiologically acceptable salt thereof, or a physiologically acceptable solvate of any of them, as claimed in claim 1, selected from the group consisting of
{4-[5-(2,5-difluoro-phenoxy)-7-propoxy-oxazolo[5,4-d]pyrimidin-2-yl]-2,6-dimethyl-phenoxy}-acetic acid,
[4-(5-cyclopentyloxy-7-propoxy-oxazolo[5,4-d]pyrimidin-2-yl)-2,6-dimethyl-phenoxy]-acetic acid,
{4-[5-(trans-2-fluoro-cyclohexyloxy)-7-propoxy-oxazolo[5,4-d]pyrimidin-2-yl]-2,6-dimethyl-phenoxy}-acetic acid,
{4-[5-(2-fluoro-phenoxy)-7-propoxy-oxazolo[5,4-d]pyrimidin-2-yl]-2,6-dimethyl-phenoxy}-acetic acid,
{4-[5-(5-fluoro-2-methyl-phenoxy)-7-propoxy-oxazolo[5,4-d]pyrimidin-2-yl]-2,6-dimethyl-phenoxy}-acetic acid,
{4-[5-(3-fluoro-4-methyl-phenoxy)-7-propoxy-oxazolo[5,4-d]pyrimidin-2-yl]-2,6-dimethyl-phenoxy}-acetic acid,
{2,6-dimethyl-4-[7-propoxy-5-(pyridin-3-yloxy)-oxazolo[5,4-d]pyrimidin-2-yl]-phenoxy}-acetic acid,
{4-[5-(2,4-difluoro-phenoxy)-7-propoxy-oxazolo[5,4-d]pyrimidin-2-yl]-2,6-dimethyl-phenoxy}-acetic acid,
[2,6-dimethyl-4-(5-phenoxy-7-propoxy-oxazolo[5,4-d]pyrimidin-2-yl)-phenoxy]-acetic acid,
{4-[5-(3-chloro-phenoxy)-7-propoxy-oxazolo[5,4-d]pyrimidin-2-yl]-2,6-dimethyl-phenoxy}-acetic acid,
[4-(5-cyclohexylmethoxy-7-propoxy-oxazolo[5,4-d]pyrimidin-2-yl)-2,6-dimethyl-phenoxy]-acetic acid,
[4-(5-isobutoxy-7-propoxy-oxazolo[5,4-d]pyrimidin-2-yl)-2,6-dimethyl-phenoxy]-acetic acid,
[4-(5-cyclobutylmethoxy-7-propoxy-oxazolo[5,4-d]pyrimidin-2-yl)-2,6-dimethyl-phenoxy]-acetic acid,
[4-(5-cyclobutoxy-7-propoxy-oxazolo[5,4-d]pyrimidin-2-yl)-2,6-dimethyl-phenoxy]-acetic acid,
[4-(5,7-dipropoxy-oxazolo[5,4-d]pyrimidin-2-yl)-2,6-dimethyl-phenoxy]-acetic acid,
{2,6-dimethyl-4-[7-propoxy-5-(3,3,3-trifluoro-propoxy)-oxazolo[5,4-d]pyrimidin-2-yl]-phenoxy}-acetic acid,
[4-(5-ethoxy-7-propoxy-oxazolo[5,4-d]pyrimidin-2-yl)-2,6-dimethyl-phenoxy]-acetic acid,
[4-(5-cyclopentylmethoxy-7-propoxy-oxazolo[5,4-d]pyrimidin-2-yl)-2,6-dimethyl-phenoxy]-acetic acid,
{2,6-dimethyl-4-[7-propoxy-5-(tetrahydrofuran-2-ylmethoxy)-oxazolo[5,4-d]pyrimidin-2-yl]-phenoxy}-acetic acid,
[4-(5-sec-butoxy-7-propoxy-oxazolo[5,4-d]pyrimidin-2-yl)-2,6-dimethyl-phenoxy]-acetic acid,
{2,6-dimethyl-4-[7-propoxy-5-(3,3,3-trifluoro-1-methyl-propoxy)-oxazolo[5,4-d]pyrimidin-2-yl]-phenoxy}-acetic acid,
{2,6-dimethyl-4-[5-(3-methyl-butoxy)-7-propoxy-oxazolo[5,4-d]pyrimidin-2-yl]-phenoxy}-acetic acid,
{4-[5-(2-cyclopropyl-ethoxy)-7-propoxy-oxazolo[5,4-d]pyrimidin-2-yl]-2,6-dimethyl-phenoxy}-acetic acid, and
{2,6-dimethyl-4-[7-propoxy-5-(2,2,2-trifluoro-1-methyl-ethoxy)-oxazolo[5,4-d]pyrimidin-2-yl]-phenoxy}-acetic acid.

6. A process for the preparation of a compound of formula I as claimed in claim 1, comprising reacting a compound of formula II with a compound of formula III,

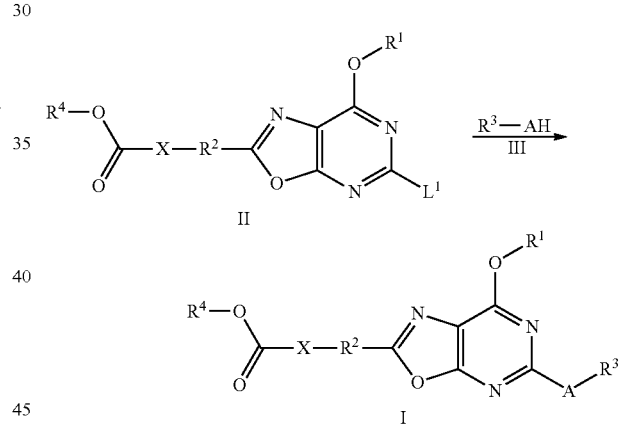

wherein the groups A, X, $R^1$, $R^2$, $R^3$ and $R^4$ in the compounds of the formulae II and III are defined as in the compounds of the formula I and additionally functional groups can be present in protected form or in the form of a precursor group, and the group $L^1$ is a halogen atom or a group of the formula —S(O)-Alk or —S(O)$_2$-Alk wherein Alk is $(C_1-C_4)$-alkyl.

7. A pharmaceutical composition, comprising at least one compound of formula I as claimed in claim 1 or a physiologically acceptable salt thereof, or a physiologically acceptable solvate of any of them, and a pharmaceutically acceptable carrier.

8. A method of treating wound healing disorders in a patient in need thereof comprising administering to said patient a therapeutically effective amount of the pharmaceutical composition of claim 7.

9. A method of wound healing in a patient in need thereof comprising administering to said patient a therapeutically effective amount of the pharmaceutical composition of claim 7.

10. A method of wound healing in a diabetic patient in need thereof comprising administering to said patient a therapeutically effective amount of the pharmaceutical composition of claim 7.

11. A method of treating diabetic foot syndrome in a patient in need thereof comprising administering to said patient a therapeutically effective amount of the pharmaceutical composition of claim 7.

12. The compound of formula I, or a physiologically acceptable salt thereof, or a physiologically acceptable solvate of any of them, as claimed in claim 1, selected from the group consisting of:

{4-[7-ethoxy-5-(3-fluorophenoxy)-oxazolo[5,4-d]pyrimidin-2-yl]-2,6-dimethyl-phenoxy}-acetic acid,
{4-[7-ethoxy-5-(2-fluorophenoxy)-oxazolo[5,4-d]pyrimidin-2-yl]-2,6-dimethyl-phenoxy}-acetic acid,
{4-[5-(isothiazol-3-yloxy)-7-propoxyoxazolo[5,4-d]pyrimidin-2-yl]-2,6-dimethylphenoxy}-acetic acid,
{2,6-dimethyl-4-[7-propoxy-5-([1,2,5]thiadiazol-3-yloxy)-oxazolo[5,4-d]pyrimidin-2-yl]-phenoxy}-acetic acid,
[2,6-dimethyl-4-(7-propoxy-5-(3-methylphenoxy)-oxazolo[5,4-d]pyrimidin-2-yl)-phenoxy]-acetic acid,
[2,6-dimethyl-4-(7-propoxy-5-(2-methylphenoxy)-oxazolo[5,4-d]pyrimidin-2-yl)-phenoxy]-acetic acid,
[2,6-dimethyl-4-(7-propoxy-5-(4-methylphenoxy)-oxazolo[5,4-d]pyrimidin-2-yl)-phenoxy]-acetic acid,
{2,6-dimethyl-4-[5-(6-methylpyridin-3-yloxy)-7-propoxy-oxazolo[5,4-d]pyrimidin-2-yl]-phenoxy}-acetic acid,
{2,6-dimethyl-4-[5-(5-methylpyridin-3-yloxy)-7-propoxy-oxazolo[5,4-d]pyrimidin-2-yl]-phenoxy}-acetic acid,
{4-[5-(3-fluorophenoxy)-7-propoxy-oxazolo[5,4-d]pyrimidin-2-yl]-2,6-dimethyl-phenoxy}-acetic acid,
{4-[5-(4-fluorophenoxy)-7-propoxy-oxazolo[5,4-d]pyrimidin-2-yl]-2,6-dimethylphenoxy}-acetic acid,
{4-[7-ethoxy-5-(5-fluoro-2-methylphenoxy)-oxazolo[5,4-d]pyrimidin-2-yl]-2,6-dimethyl-phenoxy}-acetic acid,
{4-[5-(5-fluoropyridin-3-yloxy)-7-propoxy-oxazolo[5,4-d]pyrimidin-2-yl]-2,6-dimethyl-phenoxy}-acetic acid,
{4-[5-(3-chlorophenoxy)-7-ethoxy-oxazolo[5,4-d]pyrimidin-2-yl]-2,6-dimethyl-phenoxy}-acetic acid,
{4-[5-(2,5-difluorophenoxy)-7-ethoxy-oxazolo[5,4-d]pyrimidin-2-yl]-2,6-dimethyl-phenoxy}-acetic acid,
{4-[5-(3-ethylphenoxy)-7-propoxy-oxazolo[5,4-d]pyrimidin-2-yl]-2,6-dimethyl-phenoxy}-acetic acid,
{4-[5-(3-methoxyphenoxy)-7-propoxy-oxazolo[5,4-d]pyrimidin-2-yl]-2,6-dimethylphenoxy}-acetic acid,
{4-[5-(3-fluoro-5-methylphenoxy)-7-propoxy-oxazolo[5,4-d]pyrimidin-2-yl]-2,6-dimethyl-phenoxy}-acetic acid,
{4-[5-(4-fluoro-3-methylphenoxy)-7-propoxy-oxazolo[5,4-d]pyrimidin-2-yl]-2,6-dimethyl-phenoxy}-acetic acid,
{4-[5-(2-fluoro-4-methylphenoxy)-7-propoxy-oxazolo[5,4-d]pyrimidin-2-yl]-2,6-dimethylphenoxy}-acetic acid,
{4-[5-(2-fluoro-5-methylphenoxy)-7-propoxy-oxazolo[5,4-d]pyrimidin-2-yl]-2,6-dimethylphenoxy}-acetic acid,
{4-[5-(4-chlorophenoxy)-7-propoxy-oxazolo[5,4-d]pyrimidin-2-yl]-2,6-dimethylphenoxy}-acetic acid,
{4-[5-(2-chlorophenoxy)-7-propoxy-oxazolo[5,4-d]pyrimidin-2-yl]-2,6-dimethylphenoxy}-acetic acid,
{4-[5-(5-chloropyridin-3-yloxy)-7-propoxy-oxazolo[5,4-d]pyrimidin-2-yl]-2,6-dimethyl-phenoxy}-acetic acid,
{4-[5-(2,3-difluorophenoxy)-7-propoxy-oxazolo[5,4-d]pyrimidin-2-yl]-2,6-dimethylphenoxy}-acetic acid,
{4-[5-(3,5-difluorophenoxy)-7-propoxy-oxazolo[5,4-d]pyrimidin-2-yl]-2,6-dimethyl-phenoxy}-acetic acid,
{4-[5-(3,4-difluorophenoxy)-7-propoxy-oxazolo[5,4-d]pyrimidin-2-yl]-2,6-dimethylphenoxy}-acetic acid,
{4-[5-(indan-4-yloxy)-7-propoxy-oxazolo[5,4-d]pyrimidin-2-yl]-2,6-dimethylphenoxy}-acetic acid,
{4-[5-(indan-5-yloxy)-7-propoxy-oxazolo[5,4-d]pyrimidin-2-yl]-2,6-dimethylphenoxy}-acetic acid,
{4-[5-(3-chloro-2-methylphenoxy)-7-propoxy-oxazolo[5,4-d]pyrimidin-2-yl]-2,6-dimethyl-phenoxy}-acetic acid,
{4-[5-(3-chloro-4-methylphenoxy)-7-propoxy-oxazolo[5,4-d]pyrimidin-2-yl]-2,6-dimethylphenoxy}-acetic acid,
{4-[5-(5-chloro-2-methylphenoxy)-7-propoxy-oxazolo[5,4-d]pyrimidin-2-yl]-2,6-dimethyl-phenoxy}-acetic acid,
{2,6-dimethyl-4-[5-(naphthalen-2-yloxy)-7-propoxy-oxazolo[5,4-d]pyrimidin-2-yl]-phenoxy}-acetic acid,
{2,6-dimethyl-4-[7-propoxy-5-(quinolin-3-yloxy)-oxazolo[5,4-d]pyrimidin-2-yl]-phenoxy}-acetic acid,
{4-[5-(4-chloro-2-fluorophenoxy)-7-propoxy-oxazolo[5,4-d]pyrimidin-2-yl]-2,6-dimethyl-phenoxy}-acetic acid,
{4-[5-(3-chloro-5-fluorophenoxy)-7-propoxy-oxazolo[5,4-d]pyrimidin-2-yl]-2,6-dimethyl-phenoxy}-acetic acid,
{4-[5-(2-chloro-4-fluorophenoxy)-7-propoxy-oxazolo[5,4-d]pyrimidin-2-yl]-2,6-dimethyl-phenoxy}-acetic acid,
{4-[5-(3-chloro-4-fluorophenoxy)-7-propoxy-oxazolo[5,4-d]pyrimidin-2-yl]-2,6-dimethylphenoxy}-acetic acid,
{4-[5-(3-chloro-2-fluorophenoxy)-7-propoxy-oxazolo[5,4-d]pyrimidin-2-yl]-2,6-dimethyl-phenoxy}-acetic acid,
{4-[5-(4-chloro-3-fluorophenoxy)-7-propoxy-oxazolo[5,4-d]pyrimidin-2-yl]-2,6-dimethylphenoxy}-acetic acid,
{4-[5-(2-chloro-5-fluorophenoxy)-7-propoxy-oxazolo[5,4-d]pyrimidin-2-yl]-2,6-dimethylphenoxy}-acetic acid,
{4-[5-(benzothiazol-6-yloxy)-7-propoxy-oxazolo[5,4-d]pyrimidin-2-yl]-2,6-dimethylphenoxy}-acetic acid,
{2,6-dimethyl-4-[7-propoxy-5-(3-trifluoromethylphenoxy)-oxazolo[5,4-d]pyrimidin-2-yl]-phenoxy}-acetic acid,
{2,6-dimethyl-4-[7-propoxy-5-(4-trifluoromethylphenoxy)-oxazolo[5,4-d]pyrimidin-2-yl]-phenoxy}-acetic acid,
{2,6-dimethyl-4-[7-propoxy-5-(2-trifluoromethylphenoxy)-oxazolo[5,4-d]pyrimidin-2-yl]-phenoxy}-acetic acid,
{2,6-dimethyl-4-[5-(2-methylbenzothiazol-5-yloxy)-7-propoxy-oxazolo[5,4-d]pyrimidin-2-yl]-phenoxy}-acetic acid,
{2,6-dimethyl-4-[7-propoxy-5-(2-trifluoromethoxyphenoxy)-oxazolo[5,4-d]pyrimidin-2-yl]-phenoxy}-acetic acid,
{4-[5-(2-fluoro-3-trifluoromethylphenoxy)-7-propoxy-oxazolo[5,4-d]pyrimidin-2-yl]-2,6-dimethyl-phenoxy}-acetic acid,
{4-[5-(2-fluoro-5-trifluoromethylphenoxy)-7-propoxy-oxazolo[5,4-d]pyrimidin-2-yl]-2,6-dimethylphenoxy}-acetic acid,
{4-[5-(4-fluoro-3-trifluoromethylphenoxy)-7-propoxy-oxazolo[5,4-d]pyrimidin-2-yl]-2,6-dimethyl-phenoxy}-acetic acid, {4-[5-(3-fluoro-5-trifluoromethylphenoxy)-7-propoxy-oxazolo[5,4-d]pyrimidin-2-yl]-2,6-dimethyl-phenoxy}-acetic acid,
{2,6-dimethyl-4-[7-propoxy-5-(3-trifluoromethylsulfanyl-phenoxy)-oxazolo[5,4-d]pyrimidin-2-yl]-phenoxy}-acetic acid,
{4-[5-(2-chloro-5-trifluoromethylphenoxy)-7-propoxy-oxazolo[5,4-d]pyrimidin-2-yl]-2,6-dimethyl-phenoxy}-acetic acid,
{4-[5-(4-chloro-3-trifluoromethylphenoxy)-7-propoxy-oxazolo[5,4-d]pyrimidin-2-yl]-2,6-dimethylphenoxy}-acetic acid, and
{4-[5-(2-chloro-3-trifluoromethylphenoxy)-7-propoxy-oxazolo[5,4-d]pyrimidin-2-yl]-2,6-dimethylphenoxy}-acetic acid.

* * * * *